United States Patent
Vara Salazar et al.

(10) Patent No.: US 12,202,823 B2
(45) Date of Patent: Jan. 21, 2025

(54) 1,3,4-OXADIAZOLE DERIVATIVES AS HISTONE DEACETYLASE INHIBITORS

(71) Applicants: QUIMATRYX, S.L., Guipuzcoa (ES); FUNDACIÓN KERTOR, Santiago de Compostela (ES)

(72) Inventors: Yosu Ion Vara Salazar, Guipuzcoa (ES); Eneko Aldaba Arévalo, Guipuzcoa (ES); Tamara Bello Iglesias, Guipuzcoa (ES); Richard Spurring Roberts, Santiago de Compostela (ES); Laureano Simón Buela, Guipuzcoa (ES); José Manuel Brea, Santiago de Compostela (ES); Ángel Carracedo, Santiago de Compostela (ES); María Isabel Loza García, Santiago de Compostela (ES)

(73) Assignees: QUIMATRYX, S.L., Guipuzcoa (ES); FUNDACIÓN KERTOR, Santiago de Compostela (ES)

( * ) Notice: Subject to any disclaimer, the term of this patent is extended or adjusted under 35 U.S.C. 154(b) by 694 days.

(21) Appl. No.: 17/604,017

(22) PCT Filed: Apr. 16, 2020

(86) PCT No.: PCT/EP2020/060695
§ 371 (c)(1),
(2) Date: Oct. 15, 2021

(87) PCT Pub. No.: WO2020/212479
PCT Pub. Date: Oct. 22, 2020

(65) Prior Publication Data
US 2022/0213084 A1      Jul. 7, 2022

(30) Foreign Application Priority Data

Apr. 17, 2019 (EP) .................... 19382306

(51) Int. Cl.
| | | |
|---|---|---|
| C07D 413/14 | (2006.01) | |
| C07D 413/10 | (2006.01) | |
| C07D 471/04 | (2006.01) | |
| C07D 491/107 | (2006.01) | |

(52) U.S. Cl.
CPC ......... *C07D 413/14* (2013.01); *C07D 413/10* (2013.01); *C07D 471/04* (2013.01); *C07D 491/107* (2013.01)

(58) Field of Classification Search
CPC .. C07D 413/10; C07D 413/14; C07D 471/04; C07D 491/107
See application file for complete search history.

(56) References Cited

U.S. PATENT DOCUMENTS

2018/0256572 A1    9/2018  Yates

FOREIGN PATENT DOCUMENTS

| EP | 2483242 A1 | 4/2011 |
|---|---|---|
| EP | 3330259 A1 | 6/2018 |
| WO | 2017/018803 A1 | 2/2017 |
| WO | 2017/018805 A1 | 2/2017 |
| WO | 2017/023133 A2 | 2/2017 |
| WO | 2017/222951 A1 | 12/2017 |
| WO | 2018/087082 A1 | 5/2018 |
| WO | 2018/165520 A1 | 9/2018 |

OTHER PUBLICATIONS

Zhang, Cell Death and Disease, 2018, vol. 9(460), 1-14. (Year: 2018).*
Kazantsev, Nature Reviews, Oct. 2008, vol. 7, 854-868. (Year: 2008).*
Han, E J Med Chem, vol. 258, 2023, 115613, 1-12. (Year: 2023).*
Graff, Annu Rev Pharmacol Toxicol, 2013, vol. 53, 311-330. (Year: 2013).*
Faraco, Mol Med, vol. 17(5-6), 442-447, 2011. (Year: 2011).*
Seidel et al., Histone deacetylase 6 in health and disease, Epigenomics, 2015, 7(1), 103-118.
Hubbert et al. HDAC6 is a microtubule-associated deacetylase. Nature 2002, vol. 417, 455-458.
Magiera, et al. Tubulin Posttranslational Modifications and Emerging Links to Human Disease. Cell 2018, 173, 1323-1327.
Perdiz et al. The ins and outs of tubulin acetylation: More than just a post-translational modification? Cellular Signalling 2011, 23, 763-771.
Zhang et al. Mice Lacking Histone Deacetylase 6 Have Hyperacetylated Tubulin but Are Viable and Develop Normally. Mol. Cell. Biol. 2008, vol. 28, 1688-1701.
Third Party Observations, corresponding to European Patent Application 20717897.1, dated Jun. 17, 2022.

* cited by examiner

*Primary Examiner* — D Margaret M Seaman
(74) *Attorney, Agent, or Firm* — Tristan A. Fuierer; Casimir Jones, SC

(57) ABSTRACT

The present invention refers to oxadiazole compounds suitable as HDAC6 inhibitors. Processes for their preparation and their medical uses in treating HDAC6-related diseases or disorders are also disclosed.

15 Claims, No Drawings

1,3,4-OXADIAZOLE DERIVATIVES AS HISTONE DEACETYLASE INHIBITORS

CROSS-REFERENCE TO RELATED APPLICATIONS

This application is filed under the provisions of 35 U.S.C. § 371 and claims the priority of International Patent Application No. PCT/EP2020/060695 filed on 16 Apr. 2020 entitled "1,3,4-OXADIAZOLE DERIVATIVES AS HISTONE DEACETYLASE INHIBITORS" in the name of Yosu Ion VARA SALAZAR, et al., which claims priority to European Patent Application No. 19382306.9, filed on 17 Apr. 2019, both of which are hereby incorporated by reference herein in their entirety.

FIELD OF THE INVENTION

The present invention relates to the field of medicinal chemistry, and more particularly to the field of histone deacetylases (HDACs). Small organic compounds suitable as HDAC inhibitors are herein disclosed, as are methods for their synthesis as well as their use for treating HDAC-related diseases or disorders.

BACKGROUND OF THE INVENTION

Histone deacetylases (HDACs) are epigenetic regulators that modulate chromatin structure and gene expression, and are also increasingly being associated to the control of non-epigenetic biological pathways. When the level of activity of these metalloenzymes is altered, such as when they are overexpressed, dysregulation of natural gene expression and biological processes can occur, ultimately leading to pathogenesis. It is in fact well known that HDACs play an important role in different diseases and disorders, such as neurological disorders or cancer. Therefore, controlling HDAC activity, in particular by inhibition thereof, has represented a therapeutic strategy of interest over the last decades. HDAC inhibitors of different drug classes are either already on the market—e.g. Vorinostat for use in treatment of lymphoma or valproic acid as antiepileptic—or are in development or in preclinical and clinical trials for a number of other disorders such as neurodegenerative disorders.

HDACs can be grouped into classes I to IV depending on their precise mode of action. Classes I, II and IV are defined by a zinc dependent mechanism, whereas class III HDACs require $NAD^+$ as a cofactor. Class II HDACs can be further subdivided into class IIa (HDAC4, -5, -7, -9) and IIb (HDAC6, -10). Although some overlap in function might occur, these isoforms are generally each involved in different biological pathways.

So-called pan- or broad spectrum-HDAC inhibitors, such as Vorinostat mentioned above, target the different HDACs almost indiscreetly. Unsurprisingly, considerable toxicity arises from the use of these inhibitors. In recent years, more attention has been paid to HDAC inhibitors which selectively target HDAC isoforms and lead to less off-target side-effects. Amongst said selective inhibitors are inhibitors of HDAC6. HDAC6 dysregulation has been related to a number of pathologies and the inhibition of this isoform has been reported as useful for targeting cancer, autoimmune and neurodegenerative disorders, inflammation, and a number of other diseases (Seidel et al., Epigenomics, 2015, 7(1):103-118). European patent EP2483242B1 discloses a series of HDAC6-selective inhibitors for treating cancer; whereas international patent application WO2018/087082 reports their usefulness in treating autoimmune diseases. International patent applications WO 2017/018805, WO 2017/018803 and WO 2017/023133, as well as European patent application EP 3330259, further disclose HDAC6 inhibitors based on an oxadiazole moiety.

In view of this great therapeutic potential, a constant need exists for the development of potent and selective HDAC6 inhibitors, which should ideally also possess good pharmacokinetic properties. Furthermore, straightforward syntheses of said compounds are desirable from an industrial point of view.

SUMMARY OF THE INVENTION

The present inventors have surprisingly found a series of compounds which meet the above criteria.

Thus, in a first aspect, the invention relates to a compound of formula (I)

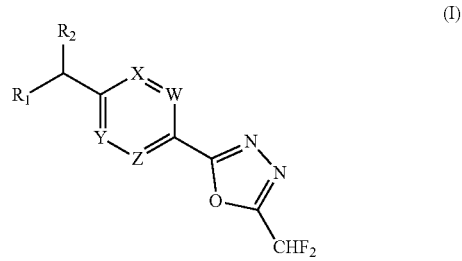

or a salt, solvate, stereoisomer or prodrug thereof, wherein one or two of W, X, Y or Z is N, and the remainder of W, X, Y and Z are each CH; or each of W, X, Y and Z is CH;

$R_1$ is H; unsubstituted or substituted alkyl; or halogen; and $R_2$ is an unsubstituted or substituted, aromatic or non-aromatic heterocyclic ring, wherein the ring comprises from 1 to 4 nitrogen atoms, and wherein it is one of these ring nitrogen atoms of the $R_2$ group that forms the bond to the rest of formula (I).

The present inventors have also developed processes through which the compounds of the invention can be easily synthesized. Thus, in a second aspect, the invention provides processes for the preparation of the compounds of the first aspect of the invention.

The invention is directed in a further aspect to a pharmaceutical composition comprising a compound of the first aspect of the invention, or a salt, solvate, stereoisomer or prodrug thereof, and at least one pharmaceutically acceptable excipient.

Another aspect of the present invention relates to a compound of general formula (I), or a salt, solvate, stereoisomer or prodrug thereof, for use as a medicament. The medicament is preferably for use in the prevention or treatment of an HDAC6-related disease or disorder.

DETAILED DESCRIPTION OF THE INVENTION

The first aspect of the invention refers to a compound of formula (I)

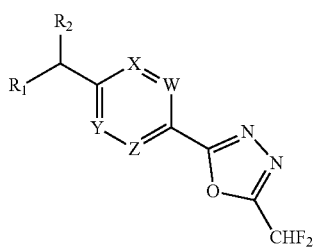

(I)

or a salt, solvate, stereoisomer or prodrug thereof, wherein one or two of W, X, Y or Z is N, and the remainder of W, X, Y and Z are each CH; or each of W, X, Y and Z is CH;

$R_1$ is H; unsubstituted or substituted alkyl; or halogen; and $R_2$ is an unsubstituted or substituted, aromatic or non-aromatic heterocyclic ring, wherein the ring comprises from 1 to 4 nitrogen atoms, and wherein it is one of these ring nitrogen atoms of the $R_2$ group that forms the bond to the rest of formula (I).

The skilled artisan understands that, when it is stated that W, X, Y or Z is CH, it is the carbon atom, and not the hydrogen atom, of said CH group that is one of the ring members of the six membered ring which comprises said W, X, Y or Z.

In an embodiment, two of W, X, Y or Z are N, and the remainder of W, X, Y and Z are each CH, in other words, the six membered ring which comprises said W, X, Y and Z is a diazine, and in particular it is a pyridazine, a pyrimidine or a pyrazine. A preferred diazine is a pyrimidine, and more preferably a pyrimidine wherein X and Y are N and Z and W are CH.

In a preferred embodiment, one of W, X, Y or Z is N, and the remainder of W, X, Y and Z are each CH, in other words, the six membered ring which comprises said W, X, Y and Z is a pyridine. In a particular embodiment, it is a pyridine wherein Z or W is N, and the remainder of W, X, Y and Z are each CH. In a more preferred particular embodiment, it is a pyridine wherein X or Y is N, and the remainder of W, X, Y and Z are each CH.

In another preferred embodiment, all of W, X, Y and Z are CH.

$R_1$ is H; unsubstituted or substituted alkyl; or halogen.

In the context of the present invention, the term "alkyl" refers to a linear, branched or cyclic hydrocarbon chain consisting of carbon and hydrogen atoms, containing no unsaturation, having from 1 to 6 carbon atoms ($C_1$-$C_6$ alkyl), preferably from 1 to 3 carbon atoms ($C_1$-$C_3$ alkyl), and being attached to the rest of the molecule through a single bond. Non-limiting examples of alkyl are methyl, ethyl, n-propyl, propyl, cyclopropyl, n-butyl, t-butyl, n-pentyl or cyclohexyl. Preferred particular alkyl groups are methyl or ethyl. The methyl group is particularly preferred.

References herein to substitution indicates that the specified group may be substituted in one or more available positions with one or more substituents.

When $R_1$ is substituted alkyl, the substituent may be a halogen. A preferred halogen is Cl or F. In a particular embodiment, the halogen is Cl. In another particular embodiment, the halogen is F.

When $R_1$ is halogen, a preferred halogen is Cl or F. In a particular embodiment, the halogen is Cl. In another particular embodiment, the halogen is F.

The term "halogen" used throughout the present disclosure refers to bromine, chlorine, iodine or fluorine.

In a preferred embodiment, $R_1$ is H.

In an embodiment, any of the above $R_1$ embodiments is combined with any of the above W, X, Y or Z embodiments.

In a preferred particular embodiment, the six membered ring which comprises W, X, Y and Z is a pyridine wherein X or Y is N, and the remainder of W, X, Y and Z are each CH; and $R_1$ is H.

In another preferred particular embodiment, all of W, X, Y and Z are CH; and $R_1$ is H.

$R_2$ is an unsubstituted or substituted, aromatic or non-aromatic heterocyclic ring, wherein the ring comprises from 1 to 4 nitrogen atoms, and wherein it is one of these ring nitrogen atoms of the $R_2$ group that forms the bond to the rest of formula (I).

In the context of the present invention, the terms "heterocycle" and "heterocyclic ring" are used interchangeably and refer to a 3 to 14 membered-, preferably 5 to 10 membered-ring comprising or made up of carbon and nitrogen atoms. The heterocyclic ring may be aromatic (also herein referred to as a heteroaryl ring or heteroaryl); or non-aromatic, including both saturated or partially unsaturated rings, as well as polycyclic rings comprising at least a cycle which is aromatic and at least another cycle which is not aromatic. The heterocyclic ring may be monocyclic or polycyclic, such as monocyclic, bicyclic or tricyclic, or preferably monocyclic or bicyclic. Polycyclic rings are also referred to in the art as polycyclic ring systems. In an embodiment, the polycyclic ring is fused, spirocyclic or bridged or presents more than one of these types of cycle junction. In an embodiment, the polycyclic ring is a fused or bridged polycyclic ring, and more preferably it is a fused polycyclic ring. The bicyclic ring is preferably a fused bicyclic ring.

In a preferred embodiment, the heterocyclic ring is a heteroaryl ring.

In a preferred embodiment, the heteroaryl ring is a 5-membered monocyclic heteroaryl ring, e.g. pyrrolyl; diazolyl, such as imidazolyl or pyrazolyl; triazolyl, such as 1,2,3-triazolyl or 1,2,4-triazolyl; or tetrazolyl. More preferably, the heteroaryl ring is an imidazolyl or a 1,2,3-triazolyl ring, and more preferably it is a 1,2,3-triazolyl ring.

In a preferred particular embodiment, the six membered ring which comprises W, X, Y and Z is a pyridine wherein X or Y is N, and the remainder of W, X, Y and Z are each CH; $R_1$ is H; and $R_2$ is imidazolyl.

In another preferred particular embodiment, all of W, X, Y and Z are CH; $R_1$ is H; and $R_2$ is imidazolyl.

In a preferred particular embodiment, the six membered ring which comprises W, X, Y and Z is a pyridine wherein X or Y is N, and the remainder of W, X, Y and Z are each CH; $R_1$ is H; and $R_2$ is 1,2,3-triazolyl.

In another preferred particular embodiment, all of W, X, Y and Z are CH; $R_1$ is H; and $R_2$ is 1,2,3-triazolyl.

A preferred 1,2,3-triazolyl is the 1H-1,2,3-triazolyl.

In an embodiment, the heteroaryl ring is a 6-membered monocyclic heteroaryl ring, such as pyridyl, diazinyl, triazinyl or tetrazinyl.

In a particular embodiment, the six membered ring which comprises W, X, Y and Z is a pyridine wherein X or Y is N, and the remainder of W, X, Y and Z are each CH; $R_1$ is H; and $R_2$ is a 6-membered monocyclic heteroaryl ring.

In a particular embodiment, all of W, X, Y and Z are CH; $R_1$ is H; and $R_2$ is a 6-membered monocyclic heteroaryl ring.

In a preferred embodiment, the heteroaryl ring is a 9-membered bicyclic heteroaryl ring. Preferably, the 9-membered bicyclic heteroaryl ring is formed by a 6-membered cycle fused to a 5-membered cycle. More preferably, it is a nitrogen atom of the 5-membered cycle that forms the bond to the rest of formula (I).

In a preferred embodiment, in the fused cycles, the fusion bond comprises no nitrogen atom, i.e. it is a carbon-carbon bond. This means that, when it is a nitrogen atom of the 5-membered cycle that forms the bond to the rest of formula (I), the 6-membered cycle can comprise from none to three nitrogen atoms (in its cycle structure, i.e. not including any nitrogen atoms comprised by any substituent of the cycle).

In a preferred embodiment, the 6-membered cycle comprises no nitrogen atoms (including the fusion bond) and therefore the from 1 to 4 nitrogen ring atoms of $R_2$ must be from 1 to 3 nitrogen ring atoms and must all be comprised in the 5-membered cycle, (excluding the fusion bond). Examples of such heteroaryl rings are the indolyl, benzoimidazolyl, indazolyl and benzotriazolyl rings. Most preferably, the heteroaryl ring ring is a benzoimidazolyl or benzotriazolyl ring.

In any of these embodiments, the 5-membered cycle is an imidazolyl or a 1,2,3-triazolyl ring, and it is more preferably a 1,2,3-triazolyl ring.

In a preferred particular embodiment, the six membered ring which comprises W, X, Y and Z is a pyridine wherein X or Y is N, and the remainder of W, X, Y and Z are each CH; $R_1$ is H; and $R_2$ is a benzimidazolyl or benzotriazolyl ring.

In a particular embodiment, all of W, X, Y and Z are CH; $R_1$ is H; and $R_2$ is a benzimidazolyl or benzotriazolyl ring.

In an embodiment, the heteroaryl ring is a 10-membered bicyclic heteroaryl ring. Preferably, this 10-membered bicyclic heteroaryl ring is formed by a 6-membered cycle fused to a 6-membered cycle, and more preferably one of the 6-membered cycles comprises no nitrogen ring atoms (including the fusion bond).

In a particular embodiment, the six membered ring which comprises W, X, Y and Z is a pyridine wherein X or Y is N, and the remainder of W, X, Y and Z are each CH; $R_1$ is H; and $R_2$ is a 10-membered bicyclic heteroaryl ring as defined above.

In a particular embodiment, all of W, X, Y and Z are CH; $R_1$ is H; and $R_2$ is a 10-membered bicyclic heteroaryl ring as defined above.

In any of the above embodiments, the $R_2$ heterocyclic ring may be unsubstituted, or it may be substituted at one or more available positions with a substituent or, where available, with more than one substituent.

Suitable $R_2$ substituent groups include:
alkyl, alkoxy, thioalkoxy, and halogenated derivatives thereof;
halogen;
phenyl and phenyl substituted with alkyl, alkoxy, thioalkoxy or halogenated derivatives thereof, or halogen;
=O, —C(=O)R, or —C(=O)OR$_a$, wherein R$_a$ is an alkyl group as defined above, or a halogenated derivative thereof; and
pyridyl and pyridyl substituted with alkyl, alkoxy, thioalkoxy or halogenated derivatives thereof, or halogen;
thiophenyl, furan or pyrrole and thiophenyl, furan or pyrrole substituted with alkyl, alkoxy, thioalkoxy or halogenated derivatives thereof, or halogen.

The $R_2$ substituent is preferably a relatively apolar group. Therefore, in an embodiment, the $R_2$ substituent group is selected from:
alkyl, alkoxy, thioalkoxy, and halogenated derivatives thereof;
halogen;
phenyl and phenyl substituted with alkyl, alkoxy, thioalkoxy or halogenated derivatives thereof, or halogen;

The term "alkyl" has the meaning defined above. A preferred alkyl group is ethyl or methyl, and even more preferably it is methyl.

In the context of the present invention, the term "alkoxy" refers to a group of formula —OR$_a$ wherein R$_a$ is an alkyl group as defined above. A preferred alkoxy group is ethoxy or methoxy, and even more preferably it is methoxy. In a different embodiment, the alkoxy group refers to an alkyl group wherein one of the nonterminal hydrocarbon units of the alkyl chain is replaced by an oxygen atom.

In the context of the present invention, the term "thioalkoxy" refers to a group of formula —SR$_a$ wherein R$_a$ is an alkyl group as defined above. A preferred thioalkoxy group is thioethoxy (-SEt) or thiomethoxy (-SMe), and even more preferably it is thiomethoxy. In a different embodiment, the thioalkoxy group refers to an alkyl group wherein one of the nonterminal hydrocarbon units of the alkyl chain is replaced by a sulfur atom.

In the context of the present invention, the term "halogenated" refers to halogen substitution, in other words, any of the above alkyl, alkoxy, thioalkoxy groups may be fully or partially substituted with a halogen atom. Preferably, the halogen atom is F or Cl, and more preferably it is F. A preferred particular halogenated substituent is the trifluoromethyl (—CF$_3$) group.

The term "halogen" has the meaning defined further above. Preferred halogens are Cl and F, both when halogen is the $R_2$ substituent, and when it is the substituent of phenyl or pyridyl when phenyl or pyridyl is the $R_2$ substituent. In an embodiment, the $R_2$ group, or the phenyl or pyridyl when it is the $R_2$ substituent, is mono-halogenated, di-halogenated or tri-halogenated, such as mono-chlorinated, di-chlorinated or tri-chlorinated or mono-fluorinated, di-fluorinated or tri-fluorinated.

In a particularly preferred embodiment, the $R_2$ substituent is halogen or phenyl substituted with halogen as defined above.

In a preferred embodiment, $R_2$ is a 5-membered monocyclic heteroaryl ring as defined in any embodiment above, and it is substituted with at least one relatively apolar group as defined in any embodiment above, preferably with phenyl or phenyl substituted with alkyl, alkoxy, thioalkoxy or halogenated derivatives thereof. In a very preferred embodiment, $R_2$ is a 5-membered monocyclic heteroaryl ring as defined in any embodiment above, and it is substituted with at least one phenyl group, such as one or two phenyl groups, wherein each of these phenyl groups may be halogenated, such as mono-halogenated, di-halogenated or tri-halogenated, e.g. mono-chlorinated, di-chlorinated or tri-chlorinated, or mono-fluorinated, di-fluorinated or tri-fluorinated. Optionally, in this very preferred embodiment, the 5-membered monocyclic heteroaryl ring is also substituted with halogen as defined in any embodiment above.

In a preferred embodiment, $R_2$ is a 9-membered bicyclic heteroaryl ring as defined in any embodiment above, and it is substituted with at least one relatively apolar group selected from alkyl, alkoxy, thioalkoxy, and halogenated derivatives thereof; and halogen, as defined in any embodiment above. In a very preferred embodiment, $R_2$ is a 9-membered monocyclic heteroaryl ring as defined in any embodiment above, and it is substituted with halogen, such as mono-halogenated, di-halogenated or tri-halogenated, e.g. mono-chlorinated, di-chlorinated or tri-chlorinated, or mono-fluorinated, di-fluorinated or tri-fluorinated.

In a preferred embodiment, the compound of formula (I) is a compound of formula (Ia)

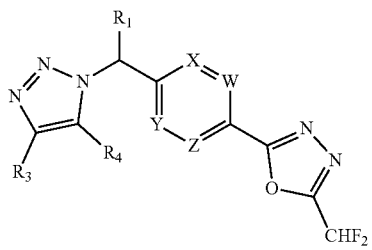

(Ia)

wherein
$R_1$, W, X, Y and Z are as defined in any embodiment above; and
$R_3$ and $R_4$ are each independently selected from a relatively apolar group as defined in any embodiment above, or $R_3$ and $R_4$, together with the triazole 4 and 5 positions, form a 6-membered cycle as defined in any of the above embodiments. In a particularly preferred embodiment, $R_4$ is H. The relatively apolar group is preferably a phenyl or phenyl substituted with alkyl, alkoxy, thioalkoxy or halogenated derivatives thereof, or halogen, most preferably substituted with halogen.

In a preferred particular embodiment, the compound of formula (I) is a compound of formula (Ia1)

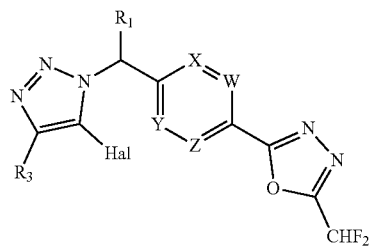

(Ia1)

wherein
$R_1$, W, X, Y and Z are as defined in any embodiment above;
$R_3$ is selected from a relatively apolar group as defined in any embodiment above, and is preferably a phenyl or phenyl substituted with alkyl, alkoxy, thioalkoxy or halogenated derivatives thereof, or halogen, most preferably substituted with halogen; and
Hal is halogen as defined in any embodiment above.

In an embodiment, the compound of formula (I) is selected from the following list:

| No. | Name | Structure |
|---|---|---|
| [1] | 2-(4-((1H-indol-1-yl)methyl)phenyl)-5-(difluoromethyl)-1,3,4-oxadiazole | 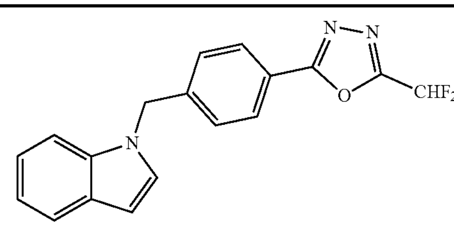 |
| [2] | 2-(4-((1H-pyrrolo[3,2-b]pyridin-1-yl)methyl)phenyl)-5-(difluoromethyl)-1,3,4-oxadiazole | 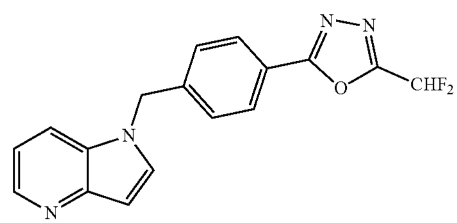 [SMILES: FC(F)c1nnc(-c2ccc(Cn3ccc4ncccc43)cc2)o1] |
| [3] | 2-(4-((1H-pyrrolo[3,2-c]pyridin-1-yl)methyl)phenyl)-5-(difluoromethyl)-1,3,4-oxadiazole | 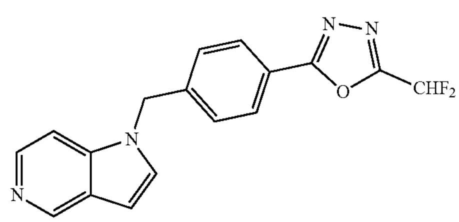 [SMILES: FC(F)c1nnc(-c2ccc(Cn3ccc4cnccc43)cc2)o1] |
| [4] | 2-(4-((1H-pyrrolo[2,3-b]pyridin-1-yl)methyl)phenyl)-5-(difluoromethyl)-1,3,4-oxadiazole | 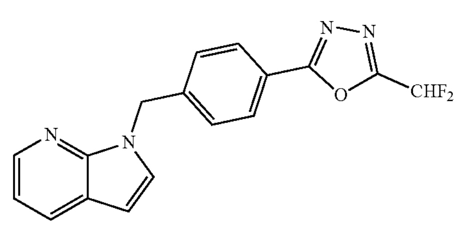 |

-continued

| No. | Name | Structure |
|---|---|---|
| [5] | 1-(1-(4-(5-(difluoromethyl)-1,3,4-oxadiazol-2-yl)benzyl)-1H-indol-3-yl)-2,2-difluoroethanone | 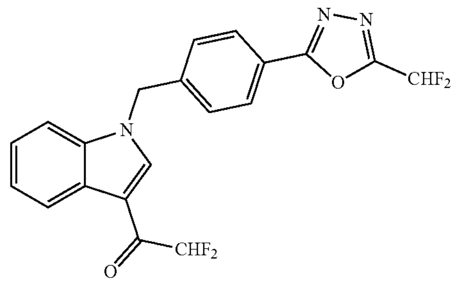 [SMILES: O=C(c1cn(Cc2ccc(-c3nnc(C(F)F)o3)cc2)c2ccccc12)C(F)F] |
| [6] | 2-(4-((1H-indazol-1-yl)methyl)phenyl)-5-(difluoromethyl)-1,3,4-oxadiazole | 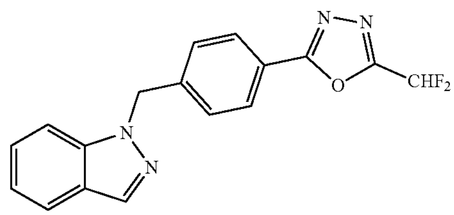 [SMILES: FC(F)c1nnc(-c2ccc(Cn3ncc4ccccc43)cc2)o1] |
| [7] | 2-(4-((2H-indazol-2-yl)methyl)phenyl)-5-(difluoromethyl)-1,3,4-oxadiazole | 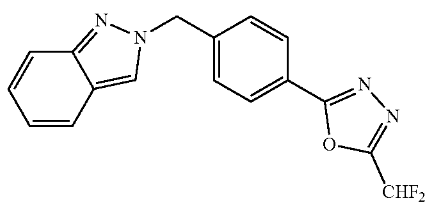 [SMILES: FC(F)c1nnc(-c2ccc(Cn3cc4ccccc4n3)cc2)o1] |
| [8] | 2-(4-((1H-benzo[d]imidazol-1-yl)methyl)phenyl)-5-(difluoromethyl)-1,3,4-oxadiazole | 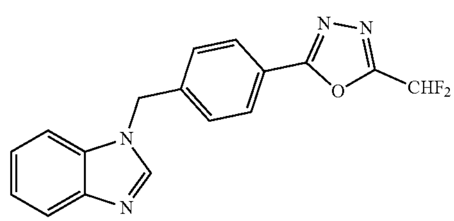 [SMILES: FC(F)c1nnc(-c2ccc(Cn3cnc4ccccc43)cc2)o1] |
| [9] | 1-(5,6-dichloro-1-(4-(5-(difluoromethyl)-1,3,4-oxadiazol-2-yl)benzyl)-1H-benzo[d]imidazol-2-yl)-2,2-difluoroethanone | 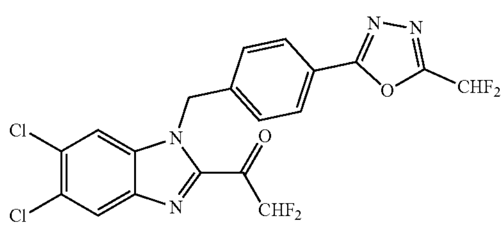 [SMILES: O=C(c1nc2cc(Cl)c(Cl)cc2n1Cc1ccc(-c2nnc(C(F)F)o2)cc1)C(F)F] |
| [10] | 2-(4-((5,6-dichloro-1H-benzo[d]imidazol-1-yl)methyl)phenyl)-5-(difluoromethyl)-1,3,4-oxadiazole | 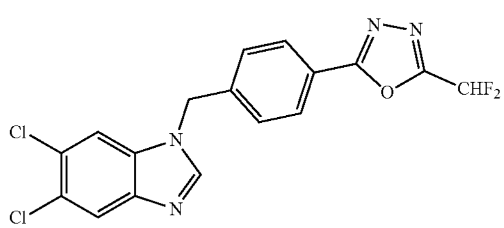 [SMILES: FC(F)c1nnc(-c2ccc(Cn3cnc4cc(Cl)c(Cl)cc43)cc2)o1] |
| [11] | 2-(4-((1H-benzo[d][1,2,3]triazol-1-yl)methyl)phenyl)-5-(difluoromethyl)-1,3,4-oxadiazole | 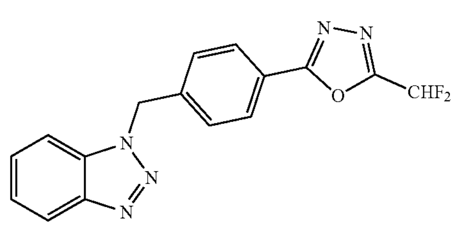 [SMILES: FC(F)c1nnc(-c2ccc(Cn3nnc4ccccc43)cc2)o1] |

-continued

| No. | Name | Structure |
|---|---|---|
| [12] | Mixture of three triazolic regioisomers | 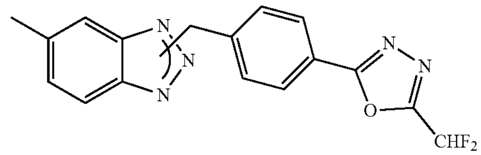 |
| [13] | 2-(4-((6-chloro-1H-benzo[d][1,2,3]triazol-1-yl)methyl)phenyl)-5-(difluoromethyl)-1,3,4-oxadiazole | 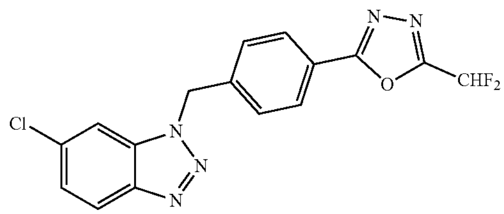 [SMILES: FC(F)c1nnc(-c2ccc(Cn3nnc4ccc(Cl)cc43)cc2)o1] |
| [14] | 1-(4-(5-(difluoromethyl)-1,3,4-oxadiazol-2-yl)benzyl)quinol-2(1H)-one | 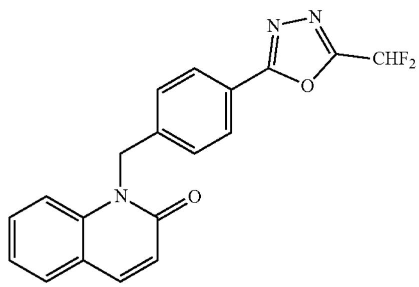 [SMILES: O=c1ccc2ccccc2n1Cc1ccc(-c2nnc(C(F)F)o2)cc1] |
| [15] | 1-(4-(5-(difluoromethyl)-1,3,4-oxadiazol-2-yl)benzyl)-3,3-dimethylindolin-2-one | 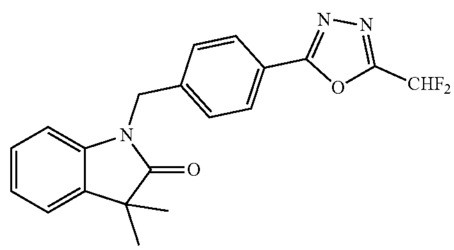 [SMILES: CC1(C)C(=O)N(Cc2ccc(-c3nnc(C(F)F)o3)cc2)c2ccccc21] |
| [16] | 2-(4-(5-(difluoromethyl)-1,3,4-oxadiazol-2-yl)benzyl)isoindoline-1,3-dione | 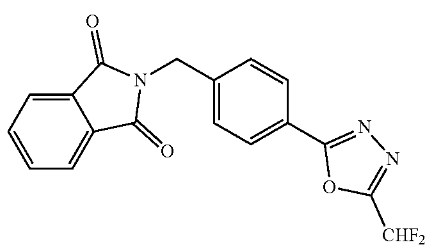 [SMILES: O=C1c2ccccc2C(=O)N1Cc1ccc(-c2nnc(C(F)F)o2)cc1] |
| [17] | 2-(difluoromethyl)-5-(4-((5-phenyl-1H-tetrazol-1-yl)methyl)phenyl)-1,3,4-oxadiazole | 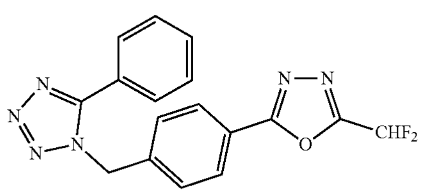 [SMILES: FC(F)c1nnc(-c2ccc(Cn3nnnc3-c3ccccc3)cc2)o1] |
| [18] | 1-(4-(5-(difluoromethyl)-1,3,4-oxadiazol-2-yl)benzyl)-4-phenyl-1H-1,2,4-triazol-5(4H)-one | 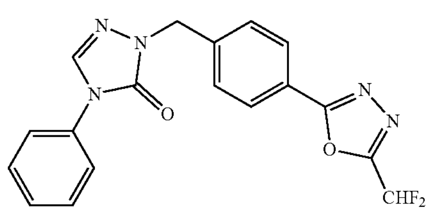 [SMILES: O=c1n(-c2ccccc2)cnn1Cc1ccc(-c2nnc(C(F)F)o2)cc1] |

-continued

| No. | Name | Structure |
|---|---|---|
| [19] | 1'-(4-(5-(difluoromethyl)-1,3,4-oxadiazol-2-yl)benzyl)spiro[cyclohexane-1,3'-indolin]-2'-one | 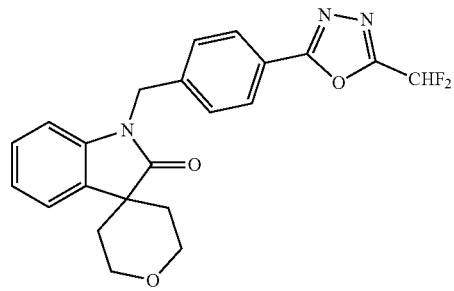 [SMILES: O=C1N(Cc2ccc(-c3nnc(C(F)F)o3)cc2)c2ccccc2C12CCOCC2] |
| [20] | 2-(4-(1-(1H-benzo[d]imidazol-1-yl)ethyl)phenyl)-5-(difluoromethyl)-1,3,4-oxadiazole | 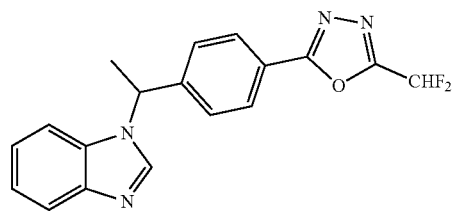 [SMILES: CC(c1ccc(-c2nnc(C(F)F)o2)cc1)n1cnc2ccccc21] |
| [21] | 2-(6-((1H-benzo[d][1,2,3]triazol-1-yl)methyl)pyridin-3-yl)-5-(difluoromethyl)-1,3,4-oxadiazole | 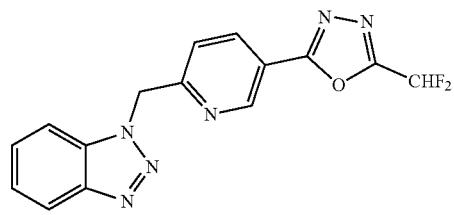 [SMILES: FC(F)c1nnc(-c2ccc(Cn3nnc4ccccc43)nc2)o1] |
| [22] | 2-(6-((5,6-dichloro-1H-benzo[d]imidazol-1-yl)methyl)pyridin-3-yl)-5-(difluoromethyl)-1,3,4-oxadiazole | 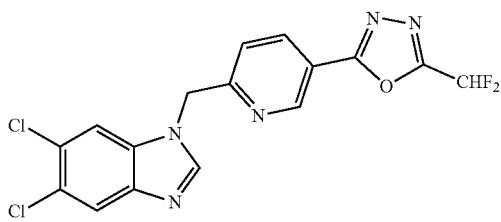 [SMILES: FC(F)c1nnc(-c2ccc(Cn3cnc4cc(Cl)c(Cl)cc43)nc2)o1] |
| [23] | 2-(6-((3H-[1,2,3]triazolo[4,5-b]pyridin-3-yl)methyl)pyridin-3-yl)-5-(difluoromethyl)-1,3,4-oxadiazole | 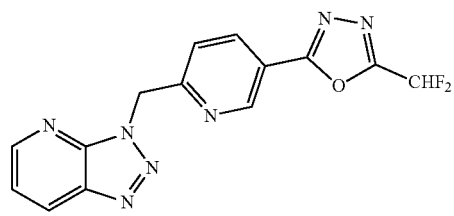 [SMILES: FC(F)c1nnc(-c2ccc(Cn3nnc4cccnc43)nc2)o1] |
| [24] | 2-(6-((5,6-dichloro-1H-benzo[d][1,2,3]triazol-1-yl)methyl)pyridin-3-yl)-5-(difluoromethyl)-1,3,4-oxadiazole | 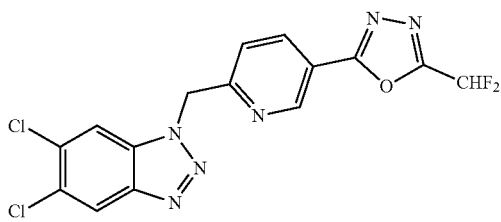 [SMILES: FC(F)c1nnc(-c2ccc(Cn3nnc4cc(Cl)c(Cl)cc43)nc2)o1] |

| No. | Name | Structure |
|---|---|---|
| [25] | 2-(6-((5,6-dichloro-2H-benzo[d][1,2,3]triazol-2-yl)methyl)pyridin-3-yl)-5-(difluoromethyl)-1,3,4-oxadiazole | 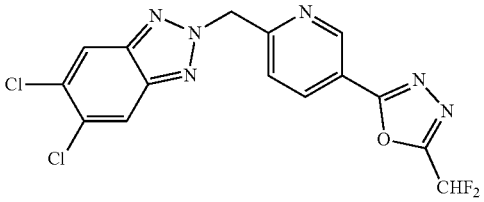 [SMILES: FC(F)c1nnc(-c2ccc(Cn3nc4cc(Cl)c(Cl)cc4n3)nc2)o1] |
| [26] | 2-(difluoromethyl)-5-(6-((4-phenyl-1H-imidazol-1-yl)methyl)pyridin-3-yl)-1,3,4-oxadiazole | 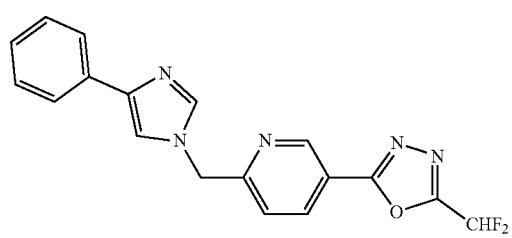 [SMILES: FC(F)c1nnc(-c2ccc(Cn3cnc(-c4ccccc4)c3)nc2)o1] |
| [27] | 2-(difluoromethyl)-5-(4-((4-phenyl-1H-1,2,3-triazol-1-yl)methyl)phenyl)-1,3,4-oxadiazole | 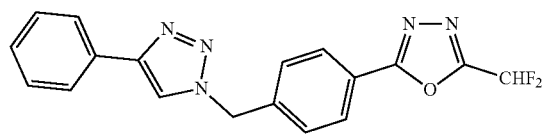 [SMILES: FC(F)c1nnc(-c2ccc(Cn3cc(-c4ccccc4)nn3)cc2)o1] |
| [28] | Methyl 1-(4-(5-(difluoromethyl)-1,3,4-oxadiazol-2-yl)benzyl)-1H-1,2,3-triazole-4-carboxylate | 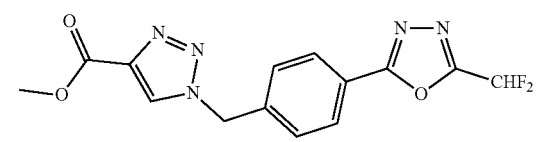 [SMILES: COC(=O)c1cn(Cc2ccc(-c3nnc(C(F)F)o3)cc2)nn1] |
| [29] | 2-(4-((4-(4-chlorophenyl)-1H-1,2,3-triazol-1-yl)methyl)phenyl)-5-(difluoromethyl)-1,3,4-oxadiazole | 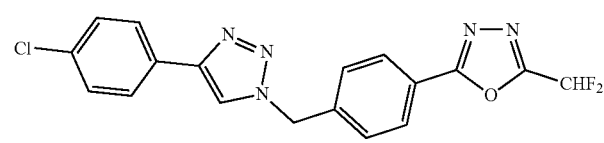 [SMILES: FC(F)c1nnc(-c2ccc(Cn3cc(-c4ccc(Cl)cc4)nn3)cc2)o1] |
| [30] | 2-(difluoromethyl)-5-(4-((4-(4-(trifluoromethyl)phenyl)-1H-1,2,3-triazol-1-yl)methyl)phenyl)-1,3,4-oxadiazole | 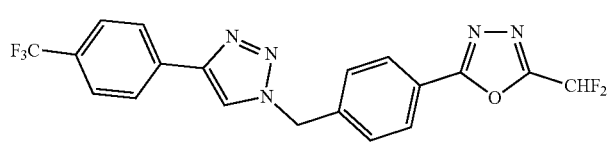 [SMILES: FC(F)c1nnc(-c2ccc(Cn3cc(-c4ccc(C(F)(F)F)cc4)nn3)cc2)o1] |
| [31] | 2-(4-((4-(tert-butyl)-1H-1,2,3-triazol-1-yl)methyl)phenyl)-5-(difluoromethyl)-1,3,4-oxadiazole | 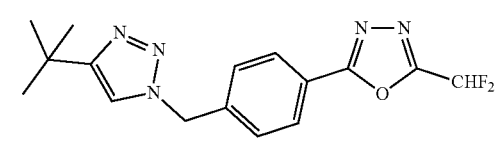 [SMILES: CC(C)(C)c1cn(Cc2ccc(-c3nnc(C(F)F)o3)cc2)nn1] |
| [32] | 2-(4-((4-cyclohexyl-1H-1,2,3-triazol-1-yl)methyl)phenyl)-5-(difluoromethyl)-1,3,4-oxadiazole | 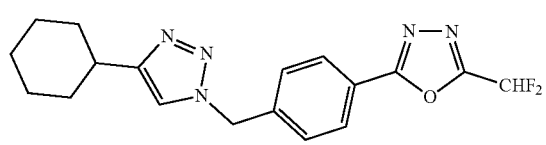 [SMILES: FC(F)c1nnc(-c2ccc(Cn3cc(C4CCCCC4)nn3)cc2)o1] |
| [33] | 2-(difluoromethyl)-5-(4-((4-(pyridin-4-yl)-1H-1,2,3-triazol-1-yl)methyl)phenyl)-1,3,4-oxadiazole | 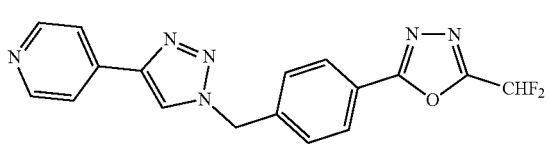 [SMILES: FC(F)c1nnc(-c2ccc(Cn3cc(-c4ccncc4)nn3)cc2)o1] |
| [34] | 2-(difluoromethyl)-5-(4-((4-(pyridin-3-yl)-1H-1,2,3-triazol-1-yl)methyl)phenyl)-1,3,4-oxadiazole | 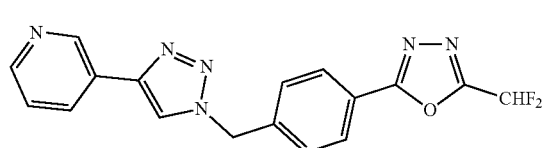 |

-continued

| No. | Name | Structure |
|---|---|---|
| [35] | 2-(difluoromethyl)-5-(4-((4-(thiophen-3-yl)-1H-1,2,3-triazol-1-yl)methyl)phenyl)-1,3,4-oxadiazole | 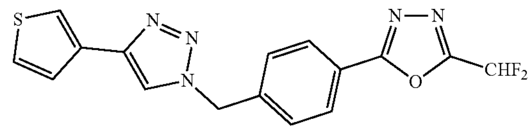 [SMILES: FC(F)c1nnc(-c2ccc(Cn3cc(-c4ccsc4)nn3)cc2)o1] |
| [36] | 2-(difluoromethyl)-5-(4-((4-(thiophen-2-yl)-1H-1,2,3-triazol-1-yl)methyl)phenyl)-1,3,4-oxadiazole | 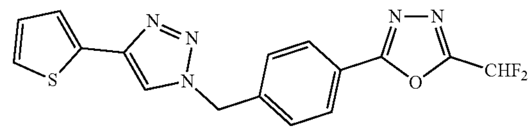 [SMILES: FC(F)c1nnc(-c2ccc(Cn3cc(-c4cccs4)nn3)cc2)o1] |
| [37] | 2-(difluoromethyl)-5-(4-(1-(4-phenyl-1H-1,2,3-triazol-1-yl)ethyl)phenyl)-1,3,4-oxadiazole | 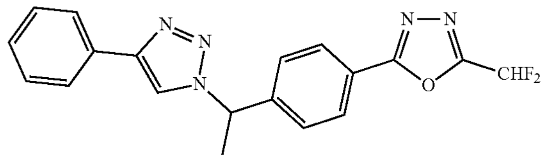 [SMILES: CC(c1ccc(-c2nnc(C(F)F)o2)cc1)n1cc(-c2ccccc2)nn1] |
| [38] | 2-(difluoromethyl)-5-(4-((4,5-diphenyl-1H-1,2,3-triazol-1-yl)methyl)phenyl)-1,3,4-oxadiazole | 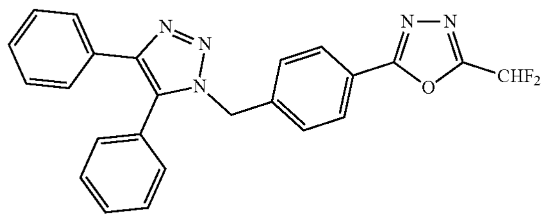 [SMILES: FC(F)c1nnc(-c2ccc(Cn3nnc(-c4ccccc4)c3-c3ccccc3)cc2)o1] |
| [39] | 2-(difluoromethyl)-5-(4-((5-methyl-4-phenyl-1H-1,2,3-triazol-1-yl)methyl)phenyl)-1,3,4-oxadiazole | 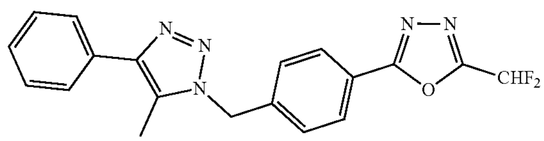 [SMILES: Cc1c(-c2ccccc2)nnn1Cc1ccc(-c2nnc(C(F)F)o2)cc1] |
| [40] | 2-(difluoromethyl)-5-(4-((4-methyl-5-phenyl-1H-1,2,3-triazol-1-yl)methyl)phenyl)-1,3,4-oxadiazole | 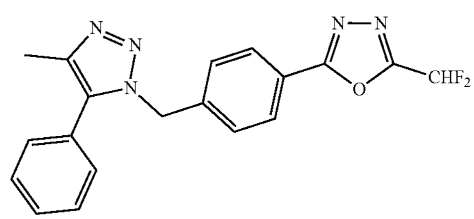 [SMILES: Cc1nnn(Cc2ccc(-c3nnc(C(F)F)o3)cc2)c1-c1ccccc1] |
| [41] | 2-(difluoromethyl)-5-(6-((4-phenyl-1H-1,2,3-triazol-1-yl)methyl)pyridin-3-yl)-1,3,4-oxadiazole | 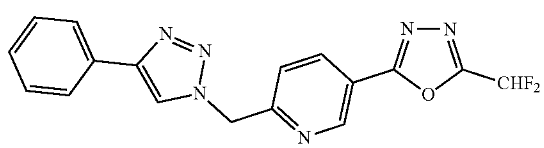 [SMILES: FC(F)c1nnc(-c2ccc(Cn3cc(-c4ccccc4)nn3)nc2)o1] |
| [42] | 2-(difluoromethyl)-5-(5-((4-phenyl-1H-1,2,3-triazol-1-yl)methyl)pyridin-2-yl)-1,3,4-oxadiazole | 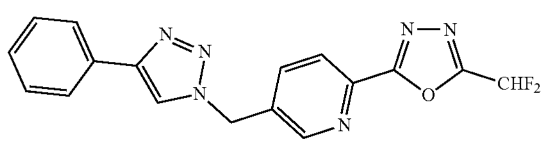 [SMILES: FC(F)c1nnc(-c2ccc(Cn3cc(-c4ccccc4)nn3)cn2)o1] |
| [43] | 2-(6-((4-(4-chlorophenyl)-1H-1,2,3-triazol-1-yl)methyl)pyridin-3-yl)-5-(difluoromethyl)-1,3,4-oxadiazole | 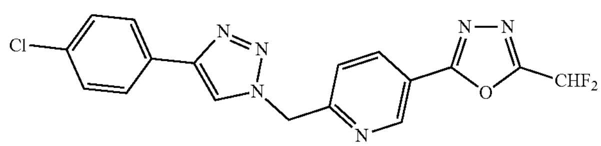 [SMILES: FC(F)c1nnc(-c2ccc(Cn3cc(-c4ccc(Cl)cc4)nn3)nc2)o1] |

-continued

| No. | Name | Structure |
|---|---|---|
| [44] | 2-(6-((4-(2-chlorophenyl)-1H-1,2,3-triazol-1-yl)methyl)pyridin-3-yl)-5-(difluoromethyl)-1,3,4-oxadiazole | 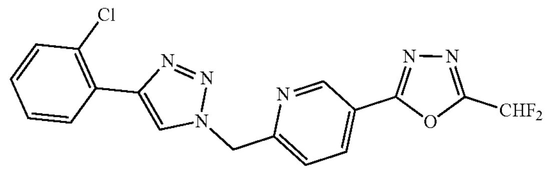 |
| [45] | 2-(6-((4-(3-chlorophenyl)-1H-1,2,3-triazol-1-yl)methyl)pyridin-3-yl)-5-(difluoromethyl)-1,3,4-oxadiazole | 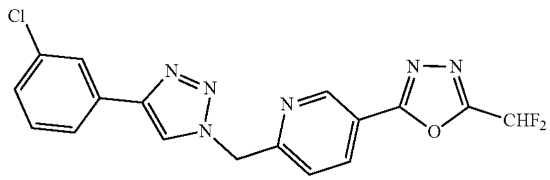 [SMILES: FC(F)c1nnc(-c2ccc(Cn3cc(-c4cccc(Cl)c4)nn3)nc2)o1] |
| [46] | 2-(6-((4-(3,4-dichlorophenyl)-1H-1,2,3-triazol-1-yl)methyl)pyridin-3-yl)-5-(difluoromethyl)-1,3,4-oxadiazole | 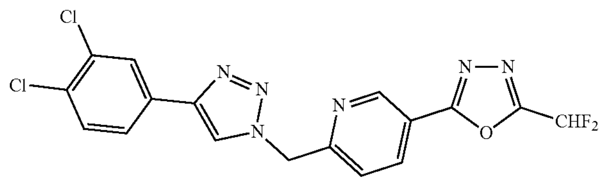 [SMILES: FC(F)c1nnc(-c2ccc(Cn3cc(-c4ccc(Cl)c(Cl)c4)nn3)nc2)o1] |
| [47] | 2-(6-((4-(3,5-dichlorophenyl)-1H-1,2,3-triazol-1-yl)methyl)pyridin-3-yl)-5-(difluoromethyl)-1,3,4-oxadiazole | 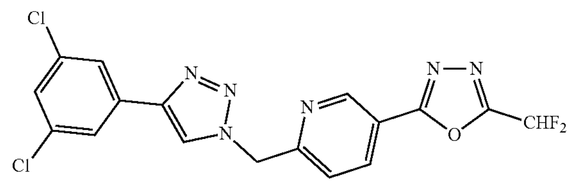 [SMILES: FC(F)c1nnc(-c2ccc(Cn3cc(-c4cc(Cl)cc(Cl)c4)nn3)nc2)o1] |
| [48] | 2-(difluoromethyl)-5-(6-((4-(2-fluorophenyl)-1H-1,2,3-triazol-1-yl)methyl)pyridin-3-yl)-1,3,4-oxadiazole | 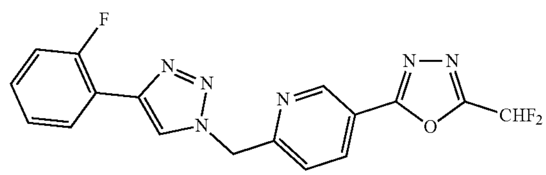 [SMILES: Fc1ccccc1-c1cn(Cc2ccc(-c3nnc(C(F)F)o3)cn2)nn1] |
| [49] | 2-(difluoromethyl)-5-(6-((4-(2,6-difluorophenyl)-1H-1,2,3-triazol-1-yl)methyl)pyridin-3-yl)-1,3,4-oxadiazole | 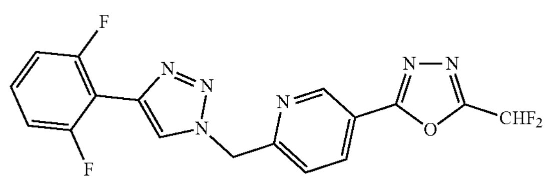 [SMILES: Fc1cccc(F)c1-c1cn(Cc2ccc(-c3nnc(C(F)F)o3)cn2)nn1] |
| [50] | 2-(6-((4-(3-chlorophenyl)-1H-1,2,3-triazol-1-yl)methyl)pyridin-3-yl)-5-(difluoromethyl)-1,3,4-oxadiazole | 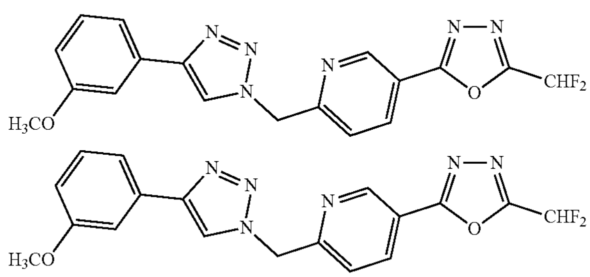 |
| [51] | 2-(4-((5-chloro-4-phenyl-1H-1,2,3-triazol-1-yl)methyl)phenyl)-5-(difluoromethyl)-1,3,4-oxadiazole | 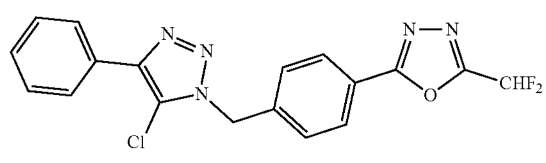 [SMILES: FC(F)c1nnc(-c2ccc(Cn3nnc(-c4ccccc4)c3Cl)cc2)o1] |

-continued

| No. | Name | Structure |
|---|---|---|
| [52] | 2-(6-((5-chloro-4-phenyl-1H-1,2,3-triazol-1-yl)methyl)pyridin-3-yl)-5-(difluoromethyl)-1,3,4-oxadiazole | 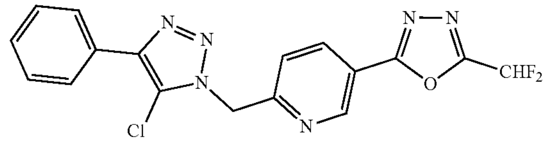 |
| [53] | 2-(6-((5-chloro-4-(2-chlorophenyl)-1H-1,2,3-triazol-1-yl)methyl)pyridin-3-yl)-5-(difluoromethyl)-1,3,4-oxadiazole | 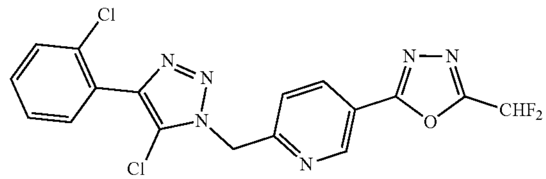 |
| [54] | 2-(6-((5-chloro-4-(3-chlorophenyl)-1H-1,2,3-triazol-1-yl)methyl)pyridin-3-yl)-5-(difluoromethyl)-1,3,4-oxadiazole | 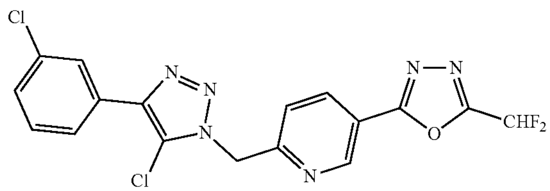 [SMILES: FC(F)c1nnc(-c2ccc(Cn3nnc(-c4cccc(Cl)c4)c3Cl)nc2)o1] |
| [55] | 2-(6-(chloro(4-phenyl-1H-1,2,3-triazol-1-yl)methyl)pyridin-3-yl)-5-(difluoromethyl)-1,3,4-oxadiazole | 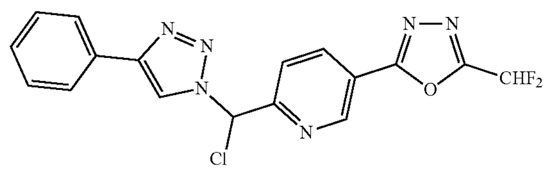 [SMILES: FC(F)c1nnc(-c2ccc(C(Cl)n3cc(-c4ccccc4)nn3)nc2)o1] |
| [56] | 2-(difluoromethyl)-5-(6-((4-(3,5-difluorophenyl)-1H-1,2,3-triazol-1-yl)methyl)pyridin-3-yl)-1,3,4-oxadiazole | 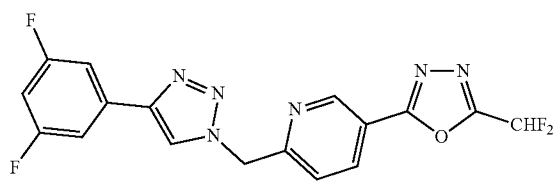 [SMILES: Fc1cc(F)cc(-c2cn(Cc3ccc(-c4nnc(C(F)F)o4)cn3)nn2)c1] |
| [57] | 2-(difluoromethyl)-5-(6-((4-(3,4,5-trifluorophenyl)-1H-1,2,3-triazol-1-yl)methyl)pyridin-3-yl)-1,3,4-oxadiazole | 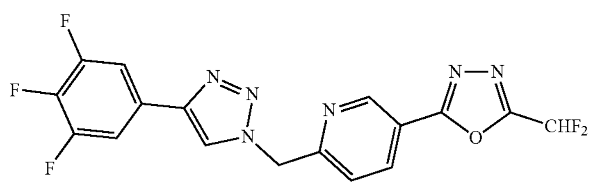 [SMILES: Fc1cc(-c2cn(Cc3ccc(-c4nnc(C(F)F)o4)cn3)nn2)cc(F)c1F] |
| [58] | 2-(6-((5,6-dichloro-2-(trifluoromethyl)-1H-benzo[d]imidazol-1-yl)methyl)pyridin-3-yl)-5-(difluoromethyl)-1,3,4-oxadiazole | 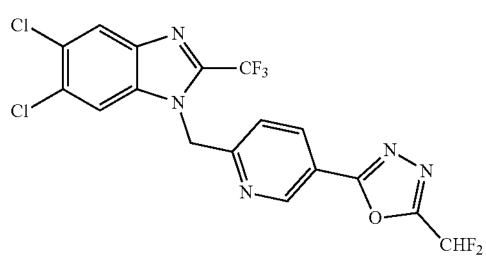 [SMILES: FC(F)c1nnc(-c2ccc(Cn3c(C(F)(F)F)nc4cc(Cl)c(Cl)cc43)nc2)o1] |
| [59] | 2-(difluoromethyl)-5-(6-((5,6-dimethyl-1H-benzo[d][1,2,3]triazol-1-yl)methyl)pyridin-3-yl)-1,3,4-oxadiazole | 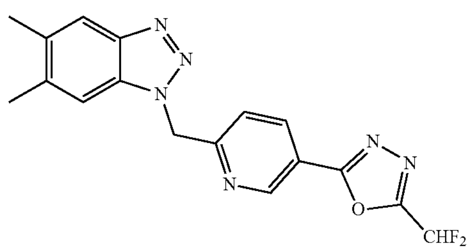 [SMILES: Cc1cc2nnn(Cc3ccc(-c4nnc(C(F)F)o4)cn3)c2cc1C] |

| No. | Name | Structure |
|---|---|---|
| [60] | 2-(6-((5,6-dichloro-2-methyl-1H-benzo[d]imidazol-1-yl)methyl)pyridin-3-yl)-5-(difluoromethyl)-1,3,4-oxadiazole | 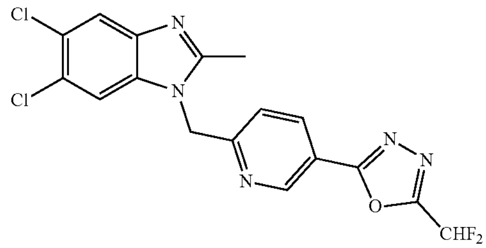 [SMILES: Cc1nc2cc(Cl)c(Cl)cc2n1Cc1ccc(-c2nnc(C(F)F)o2)cn1] |
| [61] | 2-(difluoromethyl)-5-(6-((5,6-dimethyl-1H-benzo[d]imidazol-1-yl)methyl)pyridin-3-yl)-1,3,4-oxadiazole | 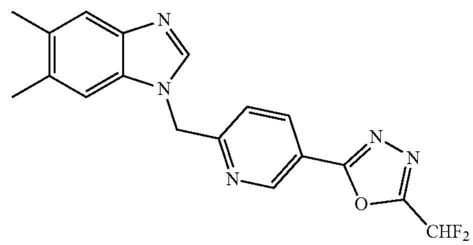 [SMILES: Cc1cc2ncn(Cc3ccc(-c4nnc(C(F)F)o4)cn3)c2cc1C] |
| [62] | 2-(6-((6-bromo-1H-benzo[d]imidazol-1-yl)methyl)pyridin-3-yl)-5-(difluoromethyl)-1,3,4-oxadiazole (enriched over Example 58) | 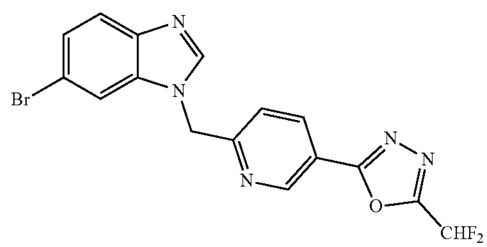 [SMILES: FC(F)c1nnc(-c2ccc(Cn3cnc4ccc(Br)cc43)nc2)o1] |
| [63] | 2-(6-((5-bromo-1H-benzo[d]imidazol-1-yl)methyl)pyridin-3-yl)-5-(difluoromethyl)-1,3,4-oxadiazole (enriched over Example 57) | 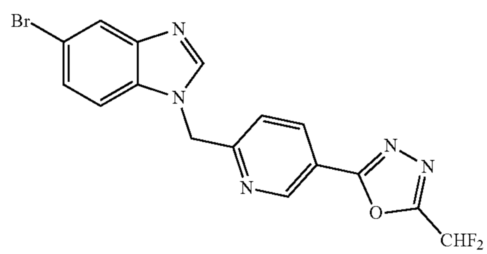 [SMILES: FC(F)c1nnc(-c2ccc(Cn3cnc4cc(Br)ccc43)nc2)o1] |
| [64] | 2-(6-((5-bromo-1H-benzo[d][1,2,3]triazol-1-yl)methyl)pyridin-3-yl)-5-(difluoromethyl)-1,3,4-oxadiazole | 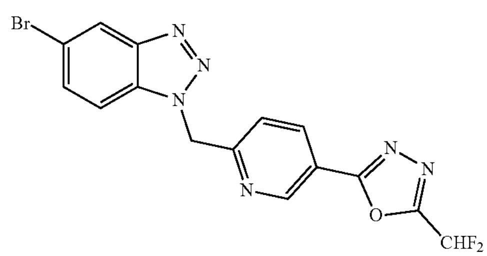 [SMILES: FC(F)c1nnc(-c2ccc(Cn3nnc4cc(Br)ccc43)nc2)o1] |
| [65] | 2-(6-((6-bromo-1H-benzo[d][1,2,3]triazol-1-yl)methyl)pyridin-3-yl)-5-(difluoromethyl)-1,3,4-oxadiazole | 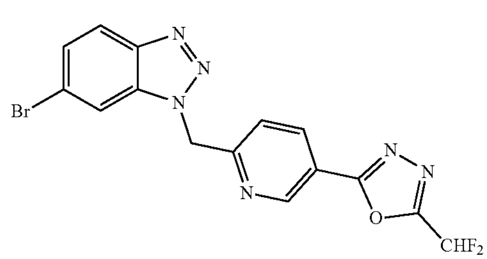 |

| No. | Name | Structure |
|---|---|---|
| [66] | 2-(6-((5-bromo-2H-benzo[d][1,2,3]triazol-2-yl)methyl)pyridin-3-yl)-5-(difluoromethyl)-1,3,4-oxadiazole | 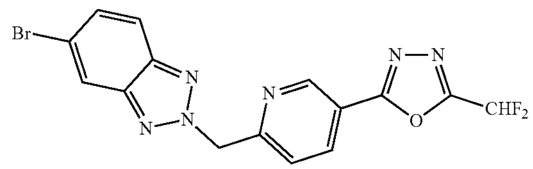 [SMILES: FC(F)c1nnc(-c2ccc(Cn3nc4ccc(Br)cc4n3)nc2)o1] |
| [67] | 2-(6-((5-chloro-4-(2-fluorophenyl)-1H-1,2,3-triazol-1-yl)methyl)pyridin-3-yl)-5-(difluoromethyl)-1,3,4-oxadiazole | 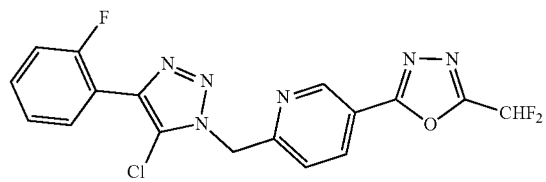 [SMILES: Fc1ccccc1-c1nnn(Cc2ccc(-c3nnc(C(F)F)o3)cn2)c1Cl] |

The compounds of formula (I) may be in the form of salts, solvates, stereoisomers or prodrugs.

The term "salt" must be understood as any form of a compound of formula (I) according to the present invention in which said compound is in ionic form, or is in ionic form and coupled to a counter-ion (a cation or anion). Preferably, the salt is a pharmaceutically acceptable salt, i.e. a salt that is tolerated physiologically, meaning that it is not toxic, particularly, as a result of the counter-ion, when used in an appropriate manner (i.e. in reasonable medical doses) for a treatment according to the present invention.

The preparation of salts can be accomplished by methods known in the art. Generally, such salts are prepared by reacting the free base forms of the compounds of the invention with the appropriate base or acid in water or in an organic solvent or in a mixture of both. In general, non-aqueous media like ether, ethyl acetate, ethanol, isopropanol or acetonitrile are preferred.

The term "solvate" in accordance with this invention should be understood as meaning any compound of formula (I) according to the present invention in which said compound is bonded by a non-covalent bond to another molecule (normally a polar solvent), including especially hydrates and alcoholates such as methanolate. A preferred solvate is the hydrate. Preferably, the solvate is a pharmaceutically acceptable solvate, i.e. a solvate that is tolerated physiologically, meaning that it is not toxic, particularly, as a result of the solvating molecule when used in an appropriate manner (i.e. in reasonable medical doses) for a treatment according to the present invention.

As used herein, the term "stereoisomer" refers to enantiomers, diastereomers, or mixtures thereof, such as a racemates, of the compounds of formula (I) according to the present invention. Likewise, the term also encompasses geometric isomers about any double bonds present in the compound of formula (I), i.e. (E)-isomers and (Z)-isomers (trans and cis isomers). Furthermore, the term also embraces rotamers of the compounds of formula (I).

Any compound of formula (I) according to the present invention may exist in different tautomeric forms. Specifically, the term "tautomer" refers to one of two or more structural isomers of a compound of formula (I) that exist in equilibrium and are readily converted from one isomeric form to the other. Common tautomeric pairs are amine-imine, amide-imidic acid, or keto-enol.

The term "prodrug" refers to derivatives of the compounds of formula (I) that are converted in vivo into the compounds of formula (I), such as by enzymatic hydrolysis.

Another aspect of the invention refers to different processes for the preparation of compounds of formula (I) as defined above. All references to W, X, Y, Z, $R_1$, $R_2$, $R_3$, $R_4$, Hal and any other variable position are as defined hereinabove for the compounds of the present invention.

The processes of the present invention comprise transforming a tetrazole of formula (II) into an oxadiazole of formula (I) in the presence of difluoroacetic anhydride (DFAA). The reaction represents a one-pot acylation and thermolysis with loss of $N_2$. The DFAA is added in molar excess with respect to the tetrazole, such as from a 5 to a 30 fold molar excess.

The reaction is typically carried out at a temperature range of from 40 to 120° C. In an embodiment, when one or two of W, X, Y or Z is N, and the remainder of W, X, Y and Z are each CH, the temperature range lies in the lower end of the range, such as from 40 to 80° C. In another embodiment, when each of W, X, Y and Z is CH, the temperature range lies in the higher end of the range, such as from 80 to 120° C.

Examples of suitable solvents for the reaction are aromatic hydrocarbons such as benzene, toluene or xylene; chlorinated hydrocarbons such as dichloromethane or chloroform; or acetone. However, in a preferred embodiment, the reaction is carried out in the absence of these solvents, as DFAA serves both as solvent and acylating agent. Once the reaction is completed, the oxadiazole of formula (I) is isolated by standard methods in the art such as organic extraction and silica column chromatography.

DFAA is readily commercially available, such as from Fluorochem Ltd. (#034690).

The tetrazole of formula (II) can be obtained in several manners.

Scheme I.

Method A.

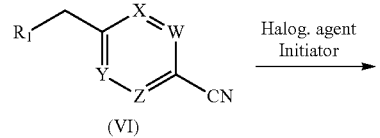

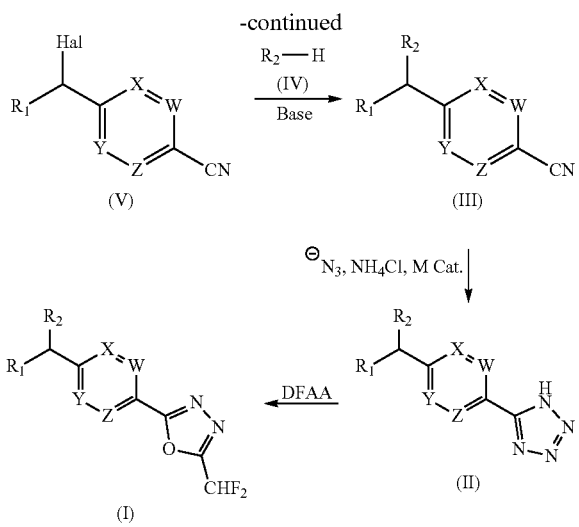

In an embodiment, the tetrazole of formula (II) is obtained as described in Scheme I above (also herein referred to as Method A). This involves reacting nitrile (III) with an azide ion in the presence of an acid addition salt of ammonia or of an amine.

Representative sources of azide ions are metal azides, especially alkali metal azides, such as sodium azide, or trialkylsilyl azides having from one to four carbon atoms in each of the alkyl groups, such as trimethylsilyl azide and triethylsilyl azide. Sodium azide is particularly preferred. The molar ratio of azide to nitrile of formula (III) is generally held in the range of from about 1:1 to about 6:1.

Examples of suitable acid addition salts are the salts with mineral acids, especially hydrochloric acid, and with organic acids such as alkane sulfonic acids e.g. methane and ethane sulfonic acids, p-toluenesulfonic acid or benzene-sulfonic acid. Examples of suitable amines for forming acid addition salts are tertiary amines such as trimethylamine, N,N-dimethylaniline, N-methylpiperdine or N-methyl-morpholine. Ammonium chloride is particularly preferred. The molar ratio of this salt to nitrile of formula (III) is generally held in the range of from about 1:1 to about 6:1, and is typically at least equimolar to the azide.

A metallic Lewis acid can be employed as a reaction catalyst. The metal coordinates the nitrile and azide groups and lowers the barrier for nucleophilic attack by the azide. A variety of catalysts have been reported in the art and include halide salts of lithium or copper, such as lithium chloride, or oxides of copper iodide or zinc. The catalyst is preferably lithium chloride. The molar ratio of catalyst to nitrile of formula (III) is generally held in the range of from about 1:2 to about 2:1.

The reaction typically proceeds in a reaction-inert solvent. Examples of suitable reaction-inert solvents for this process are N,N-dimethyl formamide (DMF), halogenated hydrocarbons such as dichloromethane (DMC) or chloroform; ethers such as dioxane, tetrahydrofuran (THF); benzene or pyridine. DMF is particularly preferred.

The reaction is generally conducted at a temperature range of from 50 to 120° C.

Acid addition salts of ammonia or amines, as well as azides and metallic catalysts are readily commercially available, e.g. from Sigma-Aldrich (ammonium chloride, #254134; sodium azide, #S2002; lithium chloride, #L4408).

In an embodiment, the nitrile of formula (III) is obtained by reacting an alkyl halide of formula (V) with a heterocyclic amine of formula (IV) in the presence of a base.

Different bases may be employed for this alkylation, such as alkali metal hydrides, e.g. NaH; alkali metal hexamethyldisilazanes (HMDSs), e,g, LiHMDS; Lithium diisopropylamide (LDA); or alkali metal carbonates, such as $Na_2CO_3$. Preferred bases are NaH and $Na_2CO_3$. From 1 to 3 molar equivalents of base are generally employed.

The reaction is preferably carried out in aprotic solvents such as THF, dioxane, DMF or Dimethyl sulfoxide (DMSO). A preferred solvent is DMF.

Preferably, the heterocyclic amine of formula (IV) is firstly treated with the base in order to deprotonate the heterocyclic amine, and the halide of formula (V) is then added.

The reaction can be carried out at temperatures ranging from −78° C. to the reflux temperature of the solvent employed. Once the reaction is completed, the nitrile of formula (III) is isolated by standard methods in the art such as organic extraction and silica column chromatography.

The halide of formula (V) is generally a bromide, iodide or chloride, and more preferably it is a bromide.

Halides of formula (V) are commercially available, such as from Sigma Aldrich (4-(Bromomethyl)benzonitrile; #144061) or Matrix Scientific (6-Bromomethyl-nicotinonitrile; #058787).

Heterocyclic amines of formula (IV) can also be easily purchased on the market, such as from Sigma Aldrich (imidazole, #56750; tetrazole, #88185; indole, #13408).

Bases are also readily commercially available, such as from Sigma Aldrich (sodium hydride; #223441).

However, in an embodiment, halides of formula (V) may be prepared by halogenation of the corresponding alkyl compound of formula (VI), this is, reaction of the alkyl compound of formula (VI) with a halogenating agent.

The halogenating agent may be any conventional halogenating agent. Examples of such halogenating agents are brominating agents such as bromine, hydrogen bromide, N-bromosuccinimide (NBS), cupric bromide, tetramethylammonium tribromide, trifluoroacetyl hypobromite, dibromoisocyanuric acid; iodinating agents such as iodine, iodine chloride, trifluoroacetyl hypoiodite, and N-iodosuccinimide; or chlorinating agents such as chlorine, thionylchloride, N-chlorosuccinimide or cupric chloride. Amongst these, N-bromosuccinimide, N-iodosuccinimide and N-chlorosuccinimide are preferred. The amount of the halogenating agent is preferably from 1 to 4 molar equivalents with respect to the alkyl compound of formula (VI).

Examples of solvents that can be used in the halogenation reaction include hydrocarbons such as heptane, hexane, cyclohexane, pentane, toluene, and xylene; ethers such as diethyl ether, THF or dioxane; halogenated hydrocarbons such as, chloroform or DCM; DMF, ethyl acetate, DMSO, or MeCN. The solvent is preferably DMF.

The aforementioned halogenation reaction is preferably performed in the presence of a radical initiator. Examples of the radical initiator include 2,2'-azobisisobutyronitrile (AIBN), 1,1'-azobis(cyclohexane-1-carbonitrile) (V-40), benzoyl peroxide or $(PhCOO)_2$. A preferred radical initiator is AIBN. The amount of the radical initiator is preferably 0.01 to 0.5 molar equivalents with respect to the alkyl compound of formula (VI).

The reaction is typically carried out at a temperature of from 0 to 100° C. Once the reaction is completed, the halide of formula (V) is isolated by standard methods in the art such as organic extraction and silica column chromatography.

Alkyl compounds of formula (VI) are readily commercially available, such as from Sigma Aldrich (p-tolunitrile; #132330) or Acros Organics (5-Cyano-2-methylpyridine; Ser. No. 15/259,816); as are halogenating agents and radical initiators, such as from Sigma-Aldrich (N-Chlorosuccinimide, #109681; AIBN, #441090).

In a different embodiment, the tetrazole of formula (II) is obtained as described in Scheme II below (also herein referred to as Method B).

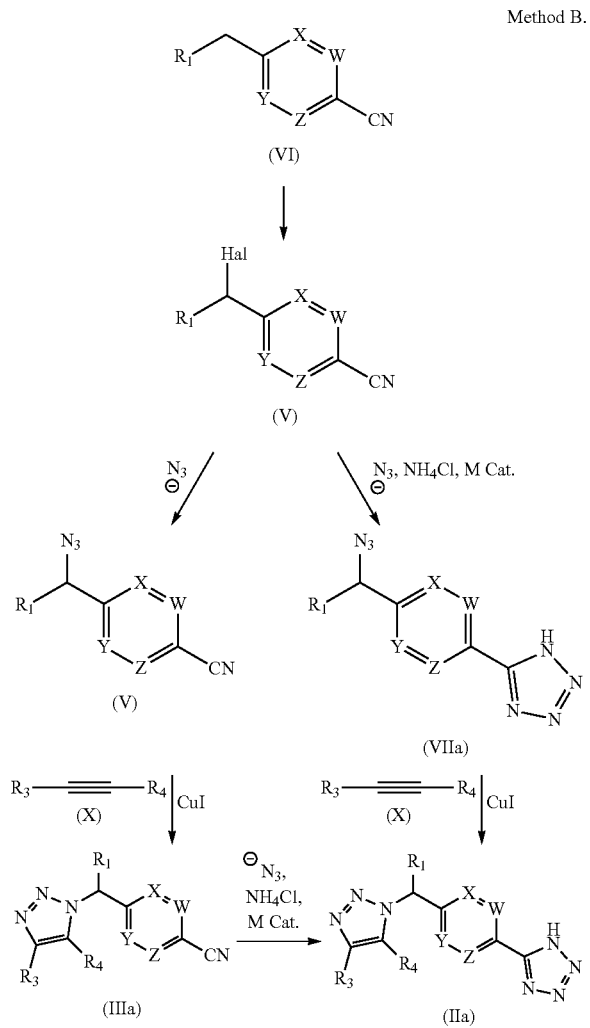

Method B specifically applies to compounds of formula (Ia) described above.

Tetrazole of formula (IIa) can be obtained from nitrile (IIIa) in the same manner as was described above for the transformation of nitrile (III) into tetrazole (II).

Nitrile (IIIa) can be prepared from azido compound (IVa) by reacting the latter with and alkyne of formula (X). The reaction represents an 1,3-cycloaddition between the azide and alkyne functional groups.

The reaction typically employs a copper(I) catalyst. A Cu(I) catalyst such as copper iodide, copper chloride or copper bromide, preferably copper iodide, can be directly employed, or, alternatively, a Cu(II) species, e.g. copper sulfate or copper acetate, along with a reducing agent such as an ascorbic acid salt, e.g. sodium ascorbate, can also be used, and these two species will react to generate the Cu(I) catalytic species in situ. When copper(I) species are directly employed, ultrasonication and/or a base are usually resorted to in order to enhance the rate of reaction.

Examples of suitable bases are amine bases such as trimethylamine, 1,8-Diazabicyclo[5.4.0]undec-7-ene (DBU) or N,N-Diisopropylethylamine (DIPEA). A preferred initiator is DIPEA.

The cycloaddition can be carried out in a variety of solvents such as protic solvents, e.g. alcohols or water; or aprotic solvents, e.g. THF, DMSO, DMF, toluene or acetone. The solvent is preferably DMF.

The reaction is usually carried out with equimolar amounts of azide (IVa) and alkyne (X), and when a copper catalyst is employed it is generally added in in catalytic amounts. When a base is resorted to, this is usually used in molar excess.

The cycloaddition can be run under mild conditions, such as at room temperature (20-25° C.), but may also be carried out at higher temperatures or under microwave irradiation. Once the reaction is completed, the nitrile of formula (IIIa) can be isolated by standard methods in the art such as organic extraction and silica column chromatography.

Copper catalysts and bases are readily available in the market, such as from Celtic Chemicals (cuprous iodide, #P400) or Sigma-Aldrich (DIPEA, #387649).

Azido compounds of formula (IVa) can be prepared by reacting a halide of formula (V) with an azide. Conditions are carefully selected so that no cycloaddition between the azide and the nitrile group of the azido compound of formula (IVa) takes place. This is achieved by carrying out the transformation in a system similar to that employed for the transformation of (V) into (VIIa), only that much milder conditions are employed. Specifically, the reaction is carried out at room temperature and no acid addition salt of ammonia or of an amine, or catalyst are employed.

Halides of formula (V) and alkyl compounds of formula (VI) can be prepared as was described above.

In an alternative pathway according to Method B, tetrazoles of formula (IIa) are prepared from azido compounds of formula (VIIa) and alkynes of formula (X) employing the same reaction as was described above for the transformation of azido compounds of formula (IVa) into nitriles of formula (IIIa).

As opposed to the pathway proceeding through intermediates (IVa) and (IIIa), according to which three independent reactions are carried out, namely a nucleophilic substitution introducing the $N_3$ group, and the nitrile and alkyne cycloadditions, the pathway proceeding through intermediate (VIIa) provides a one-step $N_3$ nucleophilic substitution and nitrile cycloaddition. This one-step double transformation can be achieved by employing the same reaction as was described above for the transformation of nitriles of formula (IIIa) into tetrazoles of formula (IIa), only ensuring that at least two molar equivalents of azide are employed with respect to the halide of formula (V). It has surprisingly been found that the pathway proceeding through intermediates (IVa) and (IIIa) is particularly suitable for compounds wherein one or two of W, X, Y or Z is N, and the remainder of W, X, Y and Z are each CH, as better overall yields are obtained than when proceeding through intermediate (VIIa).

In a different embodiment, the tetrazole of formula (II) is obtained as described in Scheme III below (also herein referred to as Method C).

Scheme III.

Method C.

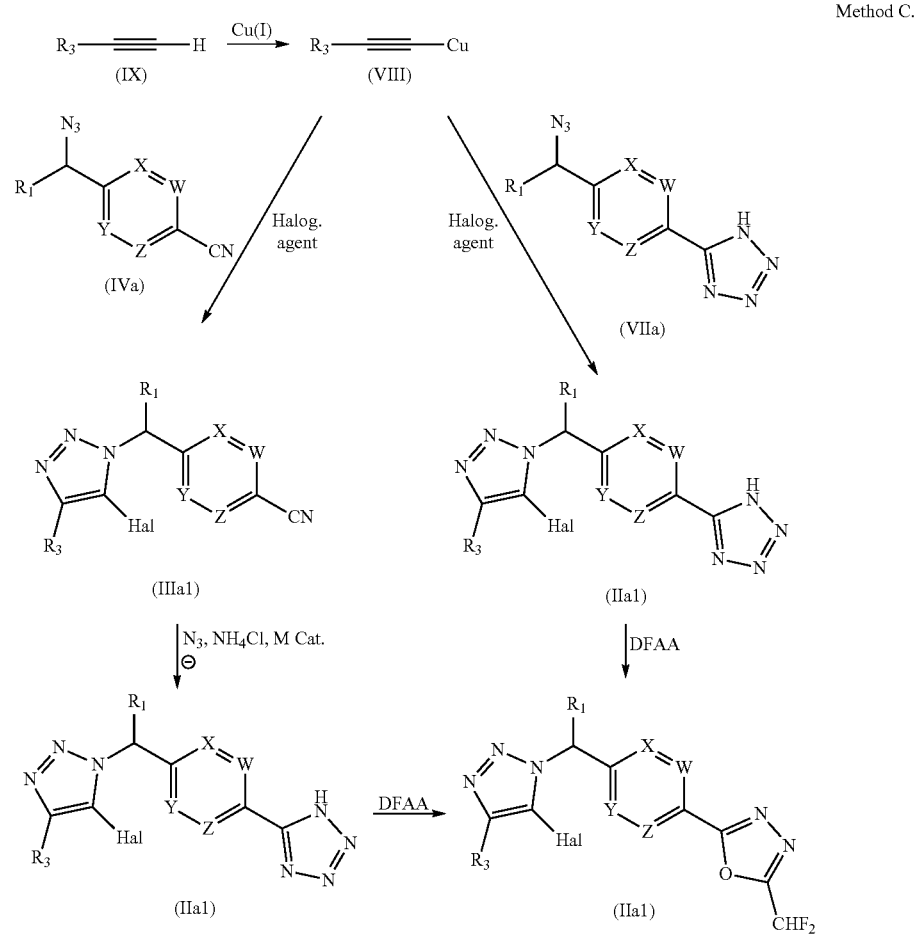

Method C specifically applies to compounds of formula (Ia1) described above.

Halogenated tetrazole of formula (IIa1) can be obtained from halogenated nitrile (IIIa1) in the same manner as was described above for the transformation of nitrile (IIIa) into tetrazole (IIa).

Halogenated nitriles of formula (IIIa1) can be prepared from cuprous acetylides of formula (VIII) by reacting the latter with an azido compound of formula (IVa) in the presence of a halogenating agent.

Halogenating agents may be for instance those described above for the transformation of alkyl compounds of formula (VI) into halides of formula (V), however the halogenating agent is preferably an N-halosuccinimide.

The azido compound, cuprous acetylide and halogenating agent can be added to the reaction mixture at the same time, however better yields of the halogenated nitriles of formula (IIIa1) are obtained if the azido compound is first reacted with the cuprous acetylide, thus forming an intermediate cuprous 1,2,3-triazolic intermediate, and the halogenating agent is then added.

The azido compound, cuprous acetylide and halogenating agent can be employed in equimolar amounts, however the azido compound and halogenating agent are usually used in a very slight excess, such as in 1.1 to 2 fold molar amounts with respect to the azido compound.

Solvents typically employed for the transformation are chlorinated hydrocarbons such as DCM, dichloroethane or chloroform.

The reaction can proceed at room temperature or higher, such as from 20° C. to the reflux temperature of the solvent. If no halogenation of other positions is desired, such as of the $R_1$ position, conditions can be tuned to avoid this, such as by employing mild reactions conditions, e.g. by running the reaction at room temperature instead of at reflux temperature, or by reducing reaction time.

Once the reaction is completed, the halogenated nitrile of formula (IIIa1) can be isolated by standard methods in the art such as organic extraction and silica column chromatography.

Cuprous acetylides of formula (VIII) can be obtained by reacting a corresponding alkyne of formula (IX) with a copper(I) species.

Representative Cu(I) species are copper(I) halides such as copper iodide or copper chloride. Alternatively, a Cu(II) species, e.g. copper sulfate, along with a reducing agent such as hydroxylammonium chloride, can also be used. The Cu(I) species is preferably CuI.

The reaction is generally carried out by dissolving the copper halide in a solvent which is less acidic than the alkyne, such as ether solvents e.g. diethyl ether, THF; chlorinated and non-chlorinated hydrocarbons, e.g. dichloromethane or toluene; or trimethylamine, aqueous ammonia or ammonium hydroxide. Preferably, the reaction is carried out in ammonium hydroxide.

Alkynes of formula (IX) or (X) are readily commercially available, such as from Sigma Aldrich (phenylacetylene, #117706; ethynyltoluene, #206504; or chloro-4-ethynylbenzene #206474).

Copper(I) or copper(II) species suitable in the above reactions can also be purchased such as from Sigma Aldrich (copper(I)chloride, #651745; copper(II)sulfate, #451657).

In an alternative pathway according to Method C, tetrazoles of formula (IIa1) are prepared directly from azido compounds of formula (VIIa) and cuprous acetylides of formula (VIII) employing the same reaction as was described above for the reaction of azido compounds of formula (IVa) with cuprous acetylides of formula (VIII) to yield halogenated nitriles of formula (IIIa1). It has unexpectedly been found that the pathway proceeding through intermediates (IVa) and (IIIa1) is particularly suitable for compounds wherein one or two of W, X, Y or Z is N, and the remainder of W, X, Y and Z are each CH, as better overall yields are obtained than when proceeding through intermediate (VIIa).

Variations of the above synthetic methods within the common general knowledge of a person skilled in the art can be used to arrive at the different compounds of formula (I) to which the present invention relates.

For instance, when $R_1$ is halogen, any of the above oxadiazoles of formula (I) can simply be halogenated employing halogenation conditions as described hereinabove.

Another aspect of the invention relates to a pharmaceutical composition comprising at least one compound of formula (I), or a salt, solvate, stereoisomer or prodrug thereof, and at least one pharmaceutically acceptable excipient. The term "excipient" refers to components of a drug compound other than the active ingredient (as defined by the European Medicines Agency—EMA). They preferably include a "carrier, adjuvant and/or vehicle". Carriers are forms to which substances are incorporated to improve the delivery and the effectiveness of drugs. Drug carriers are used in drug-delivery systems such as controlled-release technology to prolong in vivo drug actions, decrease drug metabolism, or reduce drug toxicity. Carriers are also used to increase the effectiveness of drug delivery to the target sites of pharmacological action. Adjuvant is a substance added to a drug product formulation that affects the action of the active ingredient in a predictable way. Vehicle is an excipient or a substance, preferably without therapeutic action, used as a medium to give bulk for the administration of medicines (Stedman's Medical Spellchecker© 2006 Lippincott Williams & Wilkins). Such pharmaceutical carriers, adjuvants or vehicles can be sterile liquids, such as water and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by E. W. Martin. The selection of these excipients and the amounts to be used will depend on the form of application of the pharmaceutical composition. The pharmaceutical composition according to the present invention can be in any suitable form for its application in human beings and/or animals, preferably human beings, including infants, children and adults, and can be produced by means of conventional methods known by those skilled in the art, for example those described or mentioned in the Spanish and US Pharmacopoeias and similar reference texts.

The pharmaceutical composition of the present invention can be in any form suitable for drug administration, such as intraperitoneal, intramuscular, intra-articular, intravenous, intra-arterial, intravesical, intraosseous, intracavernous, pulmonary, buccal, sublingual, ocular, intravitreal, intranasal, percutaneous, rectal, vaginal, oral, epidural, intrathecal, intraventricular, intracerebral, intracerebroventricular, intracisternal, intraspinal, paraspinal, intracranial or topical administration. Pharmaceutical forms suitable for oral administration may be tablets and capsules and may contain conventional excipients known in the art such as binders, for example syrup, gum arabic, gelatin, sorbitol, tragacanth or polyvinylpyrrolidone; fillers, for example lactose, sugar, cornstarch, calcium phosphate, sorbitol or glycine; lubricants for the preparation of tablets, for example magnesium stearate; disintegrants, for example starch, polyvinylpyrrolidone, sodium starch glycolate or microcrystalline cellulose; or pharmaceutically acceptable wetting agents such as sodium lauryl sulphate. Pharmaceutical forms suitable for parenteral administration may be sterile solutions, suspensions or lyophilized products. Suitable excipients such as fillers, buffering agents or surfactants can be used.

Another aspect of the present invention relates to a compound of formula (I) or a salt, solvate, stereoisomer or prodrug thereof, for use as a medicament. In a preferred embodiment, the medicament is for use in the prevention or treatment of an HDAC6-related disease or disorder.

Similarly, the present invention also refers to a method for preventing or treating an HDAC6-related disease or disorder in a subject in need thereof, the method comprising administering to the subject a compound of formula (I) or a pharmaceutically acceptable salt, solvate, stereoisomer or prodrug thereof.

Similarly, the present invention also refers to the use of a compound of formula (I) or of a pharmaceutically acceptable salt, solvate, stereoisomer or prodrug thereof, in the manufacture of a medicament for the prevention or treatment of an HDAC6-related disease or disorder.

Similarly, the present invention also refers to the use of a compound of formula (I) or of a pharmaceutically acceptable salt, solvate, stereoisomer or prodrug thereof, for preventing or treating an HDAC6-related disease or disorder.

As used herein, an HDAC6-related disease or disorder refers to a disease or disorder mediated, at least in part, by HDAC6. Examples of such diseases or disorders are reviewed in Van Helleputte et. al, 2014, Research and Reports in Biology, 5:1-13; Seidel et al., Epigenomics, 2015, 7(1):103-118; Ke et al., Mol Med, 2018, 24:33; Jian et al., Neuroscience Letters, 2017, 658:114-120.

In an embodiment, the HDAC6-related disease or disorder is selected from cancer, such as prostate cancer, multiple myeloma or glioblastoma multiforme; inflammation; a neurodegenerative disorder, such as Alzheimer's disease, Parkinson's disease, Huntington's disease, amyotrophic lateral sclerosis, spinal muscular atrophy, or Charcot-Marie-Tooth disease; an autoimmune disease, such as multiple sclerosis, rheumatoid arthritis or autoimmune hepatitis; peripheral neuropathy, such as chemotherapy-induced or diabetic neuropathy; major depression disorder; a kidney disease, such as autosomal dominant polycystic kidney disease, lupus nephritis or acute kidney injury; or transplantation rejection.

In addition to their ability to selectively target HDAC6, the compounds of the present invention have surprisingly been found to possess good brain-barrier permeability. Thus, a preferred embodiment of the invention relates to a compound of formula (I) for use in the treatment or prevention of a central nervous system HDAC6-related disease or disorder, such as the above mentioned neurodegenerative diseases or disorders, multiple sclerosis, or depression.

In the context of this invention, the term "treatment" or "treating" refers to the improvement or elimination of the disease or disorder.

In the context of this invention, the term "prevention" or "preventing" refers to the reduction or elimination of the risk of the disease or disorder worsening, appearing or recurring.

The compounds of the present invention can be used with at least another drug to provide a combination therapy. This other drug or drugs may be part of the same composition, or may be provided as a separate composition and can be administered at the same time or at different times. In an embodiment, more than one compound of the present invention may be used in combination with each other, as is for instance the case of Examples 12, 57 or 58 described herein. In such combinations, e.g. in the case of Examples 12, 57 or 58, the different compounds of the present invention may be present in different amounts with respect to each other.

It has also unexpectedly been found that the compounds of the present invention possess a good solubility profile as well as improved genotoxicity, which are properties often lacked by HDAC6 inhibitors.

In general, the compounds of the invention are employed in therapeutically effective amounts. What constitutes a therapeutically effective amount for any given compound of the invention can be established by a medical expert based on a number of factors such as the relative efficacy of the compound chosen, the severity of the disorder being treated or the patient's weight or age.

The following illustrative, non-limiting examples are provided to aid in the understanding of the present invention.

Synthesis of the Compounds of the Present Invention

Unless otherwise stated, reagents and substrates were purchased from commercial suppliers (Cymit Quimica S. L and Sigma-Aldrich). Thin layer chromatography (TLC) analyses were performed on silica gel 60 F254, using aluminum plates and visualized with UV lamps. Flash chromatography was carried out on columns of silica gel 60 (230-400 mesh). MS analyses were carried out using electrospray ionization (ESI) mode at 30 eV. $^1$H NMR spectra were recorded at 400 or 500 MHz for $^1$H NMR, using CDCl$_3$ or Dimethylsulfoxide (DMSO) as solvent. Purity was measured by HPLC using reverse stationary phase.

A) Examples Synthesized According to Method A of the Present Invention

Compounds of formula (I) were synthesized by applying the following synthetic protocol:

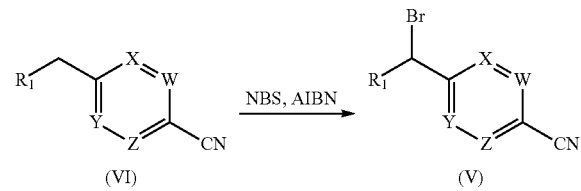

To a solution of the corresponding alkaryl compound derivative (15.6 mmol) in acetonitrile, N-bromosuccinimide (15.6 mmol, 2.37 g) and azobisisobutyronitrile (AIBN) (1.56 mmol, 0.256 g) were added. The reaction mixture was refluxed for 2 hours and azobisisobutyronitrile (0.78 mmol, 0.128 g) was added. After one hour refluxing, the mixture was allowed to stir for 16 hour at room temperature. Then, solvent was evaporated under reduced pressure, and the crude thus obtained was purified by flash chromatography (silica gel, ethyl acetate/hexane) to afford the desired bromide compound.

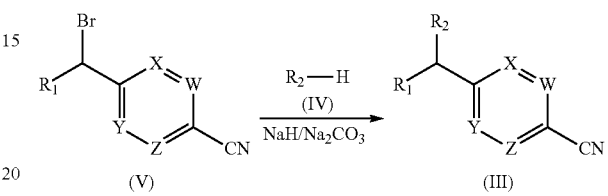

To a solution of the corresponding bromide compound (1 mmol) in N,N-dimethylformamide (DMF) at 0° C., NaH (60% in mineral oil, 1.6 mmol, 0.062 g) or Na$_2$CO$_3$ (2.3 mmol, 0.244 g) was added. After 30 minutes, the corresponding heterocyclic amine was added. The reaction was monitored by thin layer chromatography (TLC). Upon completion of the reaction, NH$_4$Cl (saturated aqueous solution) was added, and the product was extracted with ethyl acetate. The combined organic layers were dried over Na$_2$SO$_4$, filtered and concentrated. The residue was purified by flash chromatography (silica gel, ethyl acetate/hexane or MeOH/CH$_2$Cl$_2$).

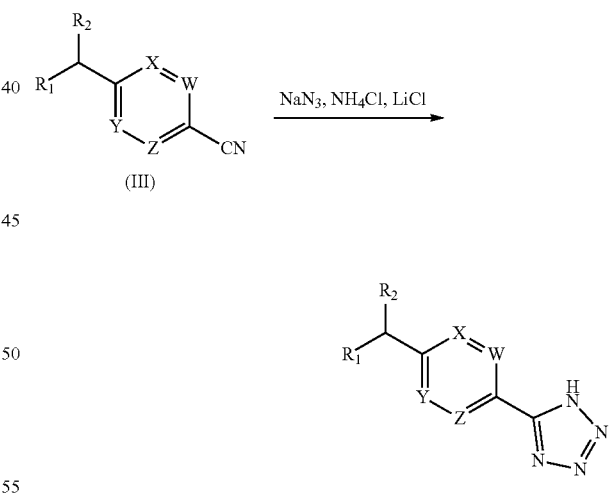

To a solution of the corresponding nitrile compound (1.0 mmol) in N,N-dimethylformamide at room temperature, NaN$_3$ (4.7 mmol, 0.305 g), NH$_4$Cl (4.7 mmol, 0.251 g) and LiCl (1.7 mmol, 0.071 g) were subsequently added. The reaction mixture was stirred at 100° C. and monitored by TLC until the completion of the reaction. The crude reaction mixture was used directly in the next step.

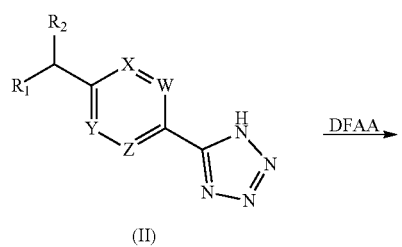

(II)

→ DFAA

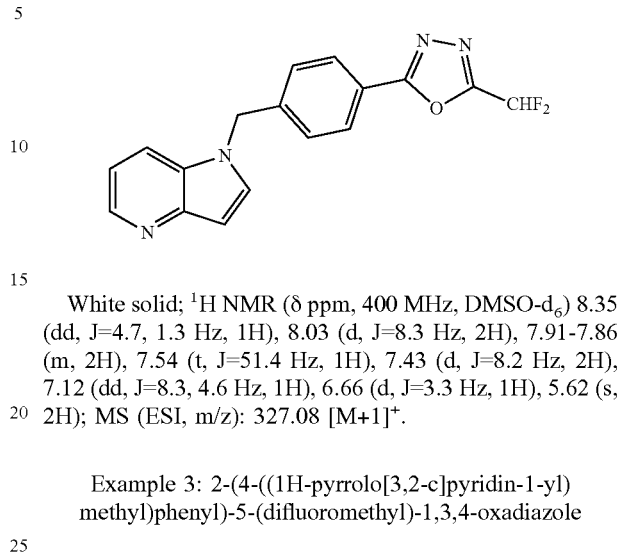

(I)

To the crude reaction obtained in the previous step, difluoroacetic anhydride (DFAA) (20.0 mmol, 2.5 ml) was added at room temperature. The reaction mixture was stirred at 60° C. (when one or two of W, X, Y or Z were N) or 100° C. (when W, X, Y and Z were each CH). The progress of the reaction was monitored by HPLC-MS. After the completion of the reaction, water was added and this solution was extracted with ethyl acetate. The combined organic fractions were washed with water and brine, dried over $Na_2SO_4$ and evaporated under reduced pressure. The crude thus obtained was purified by flash chromatography (silica gel, ethyl acetate/hexane) to afford the desired product with high purity (>90%).

Representative examples prepared by employing this protocol were:

Example 1: 2-(4-((1H-indol-1-yl)methyl)phenyl)-5-(difluoromethyl)-1,3,4-oxadiazole

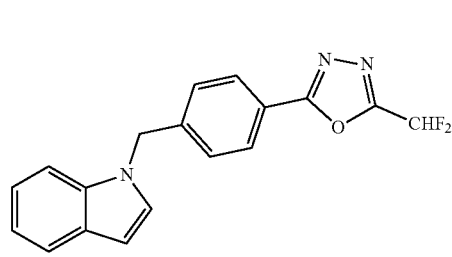

Orange solid; $^1$H NMR (δ ppm, 400 MHz, DMSO-$d_6$) 8.02 (d, J=8.3 Hz, 1H), 7.81-7.77 (m, 1H), 7.61-7.53 (m, 3H), 7.45-7.39 (m, 2H), 7.31 (d, J=8.1 Hz, 1H), 7.13-7.08 (m, 1H), 7.03 (t, J=7.4 Hz, 1H), 6.55-6.52 (m, 1H), 5.57 (app d, J=8.6 Hz, 2H); MS (ESI, m/z): 326.28 [M+1]$^+$.

Example 2: 2-(4-((1H-pyrrolo[3,2-b]pyridin-1-yl)methyl)phenyl)-5-(difluoromethyl)-1,3,4-oxadiazole

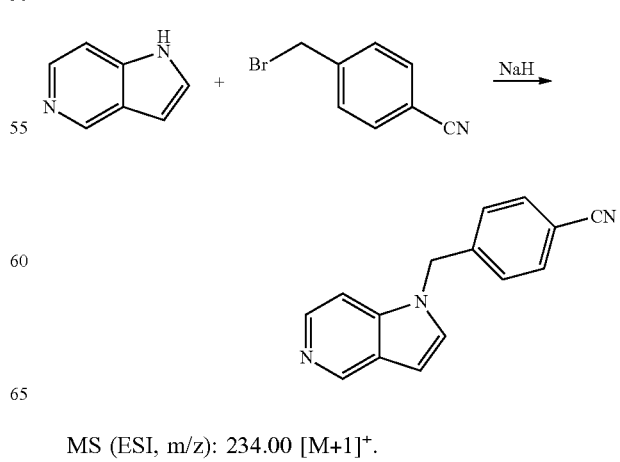

White solid; $^1$H NMR (δ ppm, 400 MHz, DMSO-$d_6$) 8.35 (dd, J=4.7, 1.3 Hz, 1H), 8.03 (d, J=8.3 Hz, 2H), 7.91-7.86 (m, 2H), 7.54 (t, J=51.4 Hz, 1H), 7.43 (d, J=8.2 Hz, 2H), 7.12 (dd, J=8.3, 4.6 Hz, 1H), 6.66 (d, J=3.3 Hz, 1H), 5.62 (s, 2H); MS (ESI, m/z): 327.08 [M+1]$^+$.

Example 3: 2-(4-((1H-pyrrolo[3,2-c]pyridin-1-yl)methyl)phenyl)-5-(difluoromethyl)-1,3,4-oxadiazole White solid; $^1$H NMR (δ ppm, 400 MHz, DMSO-$d_6$) 8.99 (s, 1H), 8.28 (d, J=6.0 Hz, 1H), 8.04 (d, J=8.3 Hz, 2H), 7.79 (d, J=3.3 Hz, 1H), 7.71 (d, J=6.0 Hz, 1H), 7.55 (t, J=51.3 Hz, 1H), 7.45 (d, J=8.1 Hz, 2H), 6.83 (d, J=3.2 Hz, 1H), 5.68 (s, 2H); MS (ESI, m/z): 327.08 [M+1]$^+$.

Intermediates 4-((1H-pyrrolo[3,2-c]pyridin-1-yl)methyl)benzonitrile

MS (ESI, m/z): 234.00 [M+1]$^+$.

1-(4-(1H-tetrazol-5-yl)benzyl)-1H-pyrrolo[3,2-c]pyridine

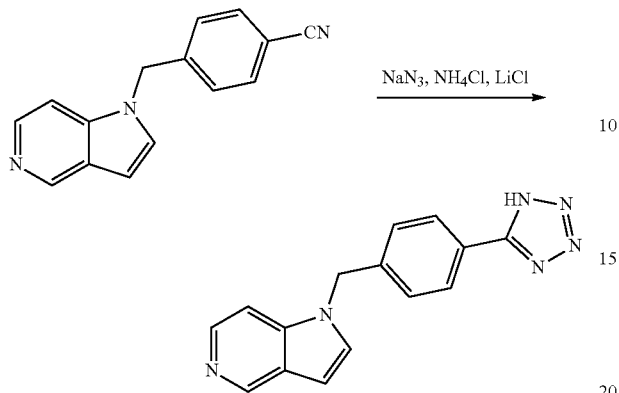

MS (ESI, m/z): 277.20 [M+1]$^+$.

Example 4: 2-(4-((1H-pyrrolo[2,3-b]pyridin-1-yl)methyl)phenyl)-5-(difluoromethyl)-1,3,4-oxadiazole

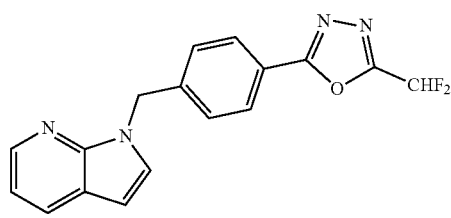 [SMILES: FC(F)c1nnc(-c2ccc(Cn3ccc4cccnc43)cc2)o1]

White solid; $^1$H NMR (δ ppm, 400 MHz, DMSO-d$_6$)$^1$H NMR (δ ppm, 400 MHz, DMSO-d$_6$) 8.27 (dd, J=4.6, 1.6 Hz, 1H), 8.04-7.99 (m, 3H), 7.70 (d, J=3.5 Hz, 1H), 7.54 (t, J=51.4 Hz, 1H), 7.44 (d, J=8.3 Hz, 2H), 7.13 (dd, J=7.8, 4.7 Hz, 1H), 6.57 (d, J=3.5 Hz, 1H), 5.62 (s, 2H); MS (ESI, m/z): 327.26 [M+1]$^+$.

Example 5: 1-(1-(4-(5-(difluoromethyl)-1,3,4-oxadiazol-2-yl)benzyl)-1H-indol-3-yl)-2,2-difluoroethanone

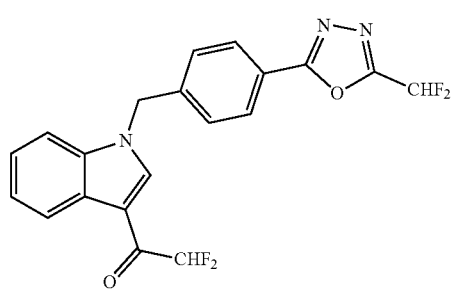 [SMILES: O=C(c1cn(Cc2ccc(-c3nnc(C(F)F)o3)cc2)c2ccccc12)C(F)F]

White solid; $^1$H NMR (δ ppm, 400 MHz, CDCl$_3$-d) 8.50-8.45 (m, 1H), 8.21-8.09 (m, 3H), 7.39 (d, J=7.0 Hz, 1H), 7.38-7.32 (m, 3H), 7.29 (d, J=2.7 Hz, 1H), 6.93 (t, J=51.7 Hz, 1H), 6.15 (t, J=54.2 Hz, 1H), 5.54 (s, 2H). MS (ESI, m/z): 402.25 [M−1]$^−$.

Example 6: 2-(4-((1H-indazol-1-yl)methyl)phenyl)-5-(difluoromethyl)-1,3,4-oxadiazole

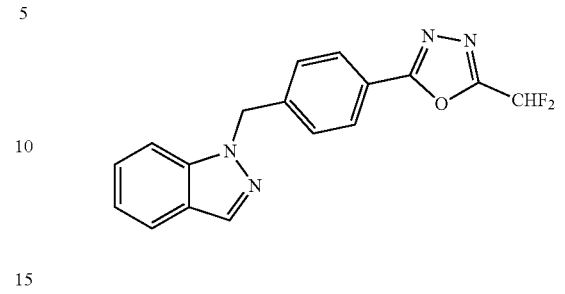

Orange solid; $^1$H NMR (δ ppm, 400 MHz, DMSO-d$_6$) 8.18 (s, 1H), 8.02 (d, J=8.1 Hz, 2H), 7.81 (dd, J=8.3, 3.5 Hz, 1H), 7.74 (d, J=8.8 Hz, 1H), 7.54 (t, J=51.4 Hz, 1H), 7.44-7.38 (m, 3H), 7.20-7.15 (m, 1H), 5.82 (s, 2H), regiochemistry was confirmed by nOe; MS (ESI, m/z): 327.26 [M+1]+.

Example 7: 2-(4-((2H-indazol-2-yl)methyl)phenyl)-5-(difluoromethyl)-1,3,4-oxadiazole

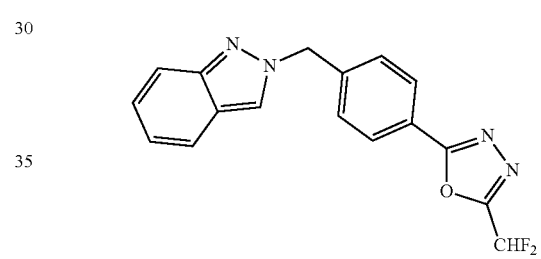

White solid; $^1$H NMR (δ ppm, 400 MHz, DMSO-d$_6$) 8.58 (d, J=0.9 Hz, 1H), 8.06 (d, J=8.2 Hz, 2H), 7.75 (d, J=8.4 Hz, 1H), 7.55 (t, J=51.4 Hz, 1H), 7.61 (d, J=8.7 Hz, 1H), 7.53 (d, J=8.2 Hz, 2H), 7.28-7.23 (m, 1H), 7.11-7.02 (m, 1H), 5.80 (s, 2H), regiochemistry was confirmed by nOe; MS (ESI, m/z): 327.05 [M+1]$^+$.

Example 8: 2-(4-((1H-benzo[d]imidazol-1-yl)methyl)phenyl)-5-(difluoromethyl)-1,3,4-oxadiazole

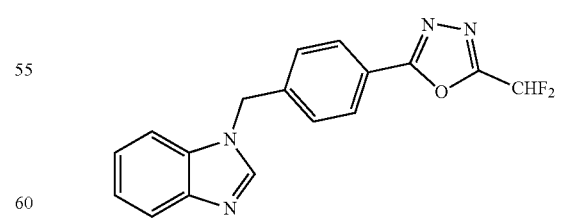

White solid; $^1$H NMR (δ ppm, 400 MHz, DMSO-d$_6$) 8.58 (d, J=0.9 Hz, 1H), 8.06 (d, J=8.2 Hz, 2H), 7.75 (d, J=8.4 Hz, 1H), 7.55 (t, J=51.4 Hz, 1H), 7.61 (d, J=8.7 Hz, 1H), 7.53 (d, J=8.2 Hz, 2H), 7.28-7.23 (m, 1H), 7.11-7.02 (m, 1H), 5.80 (s, 2H); MS (ESI, m/z): 327.03 [M+1]$^+$.

Example 9: 1-(5,6-dichloro-1-(4-(5-(difluoromethyl)-1,3,4-oxadiazol-2-yl)benzyl)-1H-benzo[d]imidazol-2-yl)-2,2-difluoroethanone

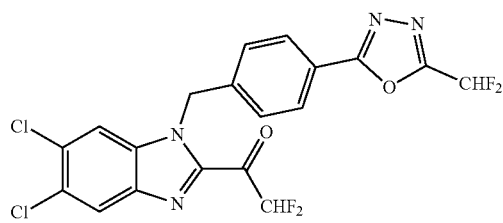 [SMILES: O=C(c1nc2cc(Cl)c(Cl)cc2n1Cc1ccc(-c2nnc(C(F)F)o2)cc1)C(F)F]

Yellow solid; $^1$H NMR (δ ppm, 400 MHz, DMSO-$d_6$) 8.38 (s, 1H), 8.35 (s, 1H), 8.03 (d, J=8.3 Hz, 2H), 7.55 (t, J=51.4 Hz, 1H), 7.42 (d, J=8.3 Hz, 2H), 7.20 (t, J=53.2 Hz, 1H), 6.01 (s, 2H); MS (ESI, m/z): 471.09 and 473.12 [M+1].

Example 10: 2-(4-((5,6-dichloro-1H-benzo[d]imidazol-1-yl)methyl)phenyl)-5-(difluoromethyl)-1,3,4-oxadiazole

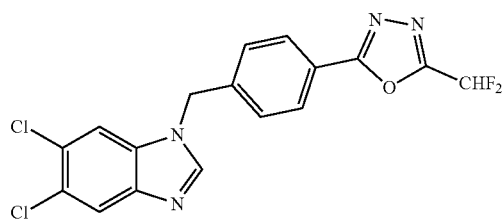 [SMILES: FC(F)c1nnc(-c2ccc(Cn3cnc4cc(Cl)c(Cl)cc43)cc2)o1]

White solid; $^1$H NMR (δ ppm, 400 MHz, DMSO-$d_6$) 8.61 (s, 1H), 8.06 (d, J=8.1 Hz, 2H), 8.00 (s, 1H), 7.97 (s, 1H), 7.55 (t, J=51.4 Hz, 1H), 7.54 (d, J=8.7 Hz, 2H), 5.68 (s, 2H); MS (ESI, m/z): 395.21 and 397.20 [M+1]$^+$ Example 11: 2-(4-((1H-benzo[d][1,2,3]triazol-1-yl)methyl)phenyl)-5-(difluoromethyl)-1,3,4-oxadiazole

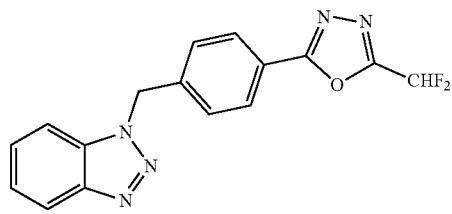 [SMILES: FC(F)c1nnc(-c2ccc(Cn3nnc4ccccc43)cc2)o1]

White solid; $^1$H NMR (δ ppm, 400 MHz, DMSO-$d_6$) 8.10 (d, J=8.4 Hz, 1H), 8.08-8.04 (m, 2H), 7.89 (d, J=8.4 Hz, 1H), 7.54 (t, J=51.4 Hz, 1H), 7.59-7.53 (m, 3H), 7.46-7.42 (m, 1H), 6.15 (s, 2H); MS (ESI, m/z): 328.24 [M+1]$^+$.

Example 12

Example 12 was tested in biological assays as a mixture of its three triazolic regioisomers, namely 2-(difluoromethyl)-5-(4-((5-methyl-1H-benzo[d][1,2,3]triazol-1-yl)methyl)phenyl)-1,3,4-oxadiazole, 2-(difluoromethyl)-5-(4-((6-methyl-1H-benzo[d][1,2,3]triazol-1-yl)methyl)phenyl)-1,3,4-oxadiazole 2-(difluoromethyl)-5-(4-((5-methyl-2H-benzo[d][1,2,3]triazol-2-yl)methyl)phenyl)-1,3,4-oxadiazole. Whilst these three regioisomers can be separated by standard methods in the art such as by silica column chromatography, they are herein presented as a mixture since this is how they were tested in the biological assays referred to hereinbelow.

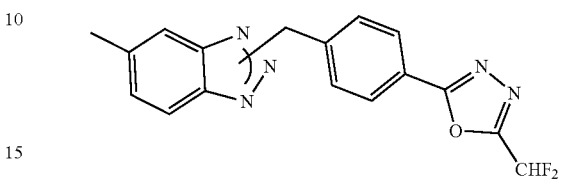

White solid; as a mixture of three regioisomers (distribution 1:1:1); MS (ESI, m/z): 342.25 [M+1]$^+$.

Example 13: 2-(4-((6-chloro-1H-benzo[d][1,2,3]triazol-1-yl)methyl)phenyl)-5-(difluoromethyl)-1,3,4-oxadiazole

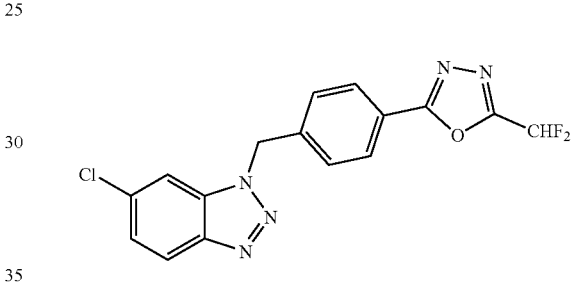

White solid; $^1$H NMR (δ ppm, 400 MHz, DMSO-$d_6$) 8.17 (d, J=1.8 Hz, 1H), 8.14 (d, J=8.8 Hz, 1H), 8.09-8.05 (m, 2H), 7.59-7.55 (m, 2H), 7.54 (t, J=51.4 Hz, 1H), 7.47 (dd, J=8.8, 1.9 Hz, 1H), 6.12 (s, 2H), Regiochemistry was confirmed by nOe enhancement between the proton at 6.12 ppm and the proton at 8.17 ppm; MS (ESI, m/z): 362.18 and 364.21 [M+1]$^+$.

Example 14: 1-(4-(5-(difluoromethyl)-1,3,4-oxadiazol-2-yl)benzyl)naphthalen-2(1H)-one

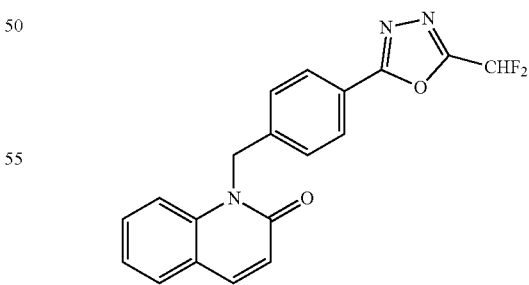

White solid; $^1$H NMR (δ ppm, 400 MHz, DMSO-$d_6$) 8.05 (d, J=10.1 Hz, 1H), 8.03 (d, J=8.7 Hz, 2H), 7.79 (dd, J=7.8, 1.5 Hz, 1H), 7.54 (t, J=51.4 Hz, 1H), 7.53-7.50 (m, 1H), 7.45 (d, J=8.2 Hz, 2H), 7.39 (d, J=8.6 Hz, 1H), 7.27 (t, J=7.4 Hz, 1H), 6.77 (d, J=9.5 Hz, 1H), 5.65 (s, 2H); MS (ESI, m/z): 354.30 [M+1]$^+$.

Example 15: 1-(4-(5-(difluoromethyl)-1,3,4-oxadiazol-2-yl)benzyl)-3,3-dimethylindolin-2-one

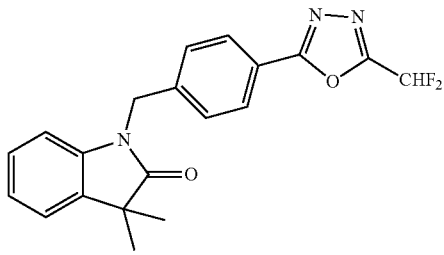 [SMILES: CC1(C)C(=O)N(Cc2ccc(-c3nnc(C(F)F)o3)cc2)c2ccccc21]

White solid; $^1$H NMR (δ ppm, 400 MHz, DMSO-d$_6$) 8.03 (d, J=8.3 Hz, 2H), 7.53 (t, J=53.6 Hz, 1H), 7.52 (d, J=8.3 Hz, 2H), 7.39 (dd, J=7.6, 1.5 Hz, 1H), 7.18 (td, J=7.7, 1.3 Hz, 1H), 7.04 (td, J=7.5, 1.0 Hz, 1H), 6.91 (d, J=7.8 Hz, 1H), 5.02 (s, 2H), 1.35 (s, 6H); MS (ESI, m/z): 370.27 [M+1]$^+$.

Example 16: 2-(4-(5-(difluoromethyl)-1,3,4-oxadiazol-2-yl)benzyl)isoindoline-1,3-dione

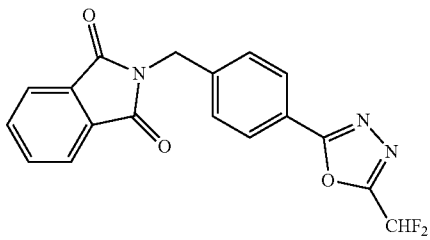 [SMILES: O=C1c2ccccc2C(=O)N1Cc1ccc(-c2nnc(C(F)F)o2)cc1]

White solid; $^1$H NMR (δ ppm, 400 MHz, DMSO-d$_6$) 8.04 (d, J=8.3 Hz, 2H), 7.97-7.92 (m, 2H), 7.92-7.87 (m, 2H), 7.58 (d, J=8.1 Hz, 2H), 7.55 (t, J=51.4 Hz, 1H), 4.90 (s, 2H); MS (ESI, m/z): 356.26 [M+1]$^+$.

Example 17: 2-(difluoromethyl)-5-(4-((5-phenyl-1H-tetrazol-1-yl)methyl)phenyl)-1,3,4-oxadiazole

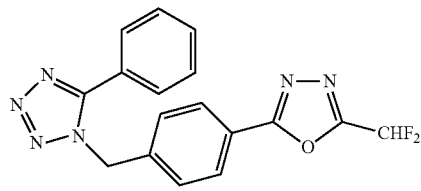 [SMILES: FC(F)c1nnc(-c2ccc(Cn3nnnc3-c3ccccc3)cc2)o1]

White solid; MS (ESI, m/z): 355.28 [M+1]$^+$.

Example 18: 1-(4-(5-(difluoromethyl)-1,3,4-oxadiazol-2-yl)benzyl)-4-phenyl-1H-1,2,4-triazol-5(4H)-one

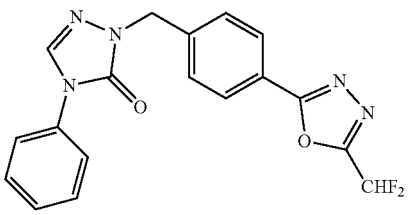 [SMILES: O=c1n(-c2ccccc2)cnn1Cc1ccc(-c2nnc(C(F)F)o2)cc1]

White solid; $^1$H NMR (δ ppm, 400 MHz, DMSO-d$_6$) 8.58 (s, 1H), 8.10-8.06 (m, 2H), 7.76-7.72 (m, 2H), 7.60-7.52 (m, 4H), 7.54 (t, J=58.9 Hz, 1H), 7.45-7.38 (m, 1H), 5.12 (s, 2H); MS (ESI, m/z): 370.24 [M+1]$^+$.

Example 19: 1'-(4-(5-(difluoromethyl)-1,3,4-oxadiazol-2-yl)benzyl)spiro[cyclohexane-1,3'-indolin]-2'-one

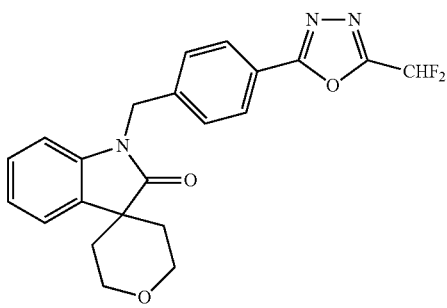 [SMILES: O=C1N(Cc2ccc(-c3nnc(C(F)F)o3)cc2)c2ccccc2C12CCOCC2]

White solid; $^1$H NMR (δ ppm, 400 MHz, DMSO-d$_6$) 8.07-8.01 (m, 2H), 7.60 (dd, J=7.5, 1.2 Hz, 1H), 7.55 (t, J=51.8 Hz, 1H), 7.54 (d, J=8.5 Hz, 2H), 7.23 (td, J=7.7, 1.2 Hz, 1H), 7.07 (td, J=7.5, 1.0 Hz, 1H), 6.93 (d, J=7.8 Hz, 1H), 5.04 (s, 2H), 4.11 (ddd, J=11.7, 7.6, 4.2 Hz, 2H), 3.87 (dt, J=11.6, 4.9 Hz, 2H), 1.84 (dt, J=9.3, 4.6 Hz, 4H). MS (ESI, m/z): 412.33 [M+1]$^+$.

Example 20: 2-(4-(1-(1H-benzo[d]imidazol-1-yl)ethyl)phenyl)-5-(difluoromethyl)-1,3,4-oxadiazole

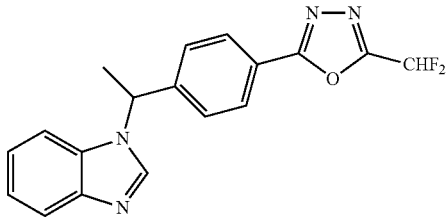 [SMILES: CC(c1ccc(-c2nnc(C(F)F)o2)cc1)n1cnc2ccccc21]

White solid; $^1$H NMR (400 MHz, Chloroform-d) 8.19 (s, 1H), 8.12 (d, J=8.4 Hz, 2H), 7.87 (d, J=8.1 Hz, 1H), 7.38 (d, J=8.3 Hz, 2H), 7.33-7.30 (m, 1H), 7.23 (t, J=7.5 Hz, 1H), 7.15 (d, J=8.2 Hz, 1H), 6.93 (t, J=51.7 Hz, 1H), 5.74 (q, J=7.1 Hz, 1H), 2.10 (d, J=7.1 Hz, 3H); MS (ESI, m/z): 341.27 [M+1]$^+$.

Example 21: 2-(6-((1H-benzo[d][1,2,3]triazol-1-yl)methyl)pyridin-3-yl)-5-(difluoromethyl)-1,3,4-oxadiazole

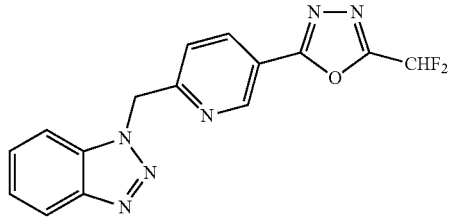 [SMILES: FC(F)c1nnc(-c2ccc(Cn3nnc4ccccc43)nc2)o1]

Yellow oil; $^1$H NMR (δ ppm, 400 MHz, DMSO-d$_6$) 9.13 (d, J=2.2 Hz, 1H), 8.47 (dd, J=8.2, 2.3 Hz, 1H), 8.10 (d, J=8.4 Hz, 1H), 7.84 (d, J=8.3 Hz, 1H), 7.60-7.54 (m, 2H), 7.56 (t, J=58.2 Hz, 1H), 7.47-7.42 (m, 1H), 6.27 (s, 2H); MS (ESI, m/z): 329.43 [M+1]$^+$.

Example 22: 2-(6-((5,6-dichloro-1H-benzo[d]imidazol-1-yl)methyl)pyridin-3-yl)-5-(difluoromethyl)-1,3,4-oxadiazole

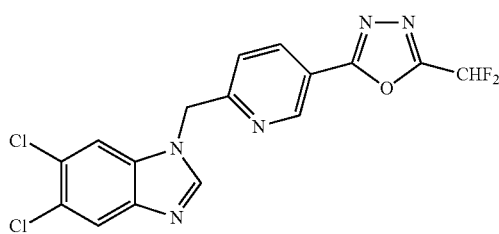 [SMILES: FC(F)c1nnc(-c2ccc(Cn3cnc4cc(Cl)c(Cl)cc43)nc2)o1]

White solid; $^1$H NMR (δ ppm, 400 MHz, DMSO-d$_6$) 9.16-9.13 (m, 1H), 8.54 (s, 1H), 8.46 (dd, J=8.2, 2.3 Hz, 1H), 8.00 (s, 1H), 7.97 (s, 1H), 7.58 (d, J=7.7 Hz, 1H), 7.51 (t, J=51.0 Hz, 1H), 5.80 (s, 2H); MS (ESI, m/z): 396.22 and 398.22 [M+1]$^+$.

Example 23: 2-(6-((3H-[1,2,3]triazolo[4,5-b]pyridin-3-yl)methyl)pyridin-3-yl)-5-(difluoromethyl)-1,3,4-oxadiazole

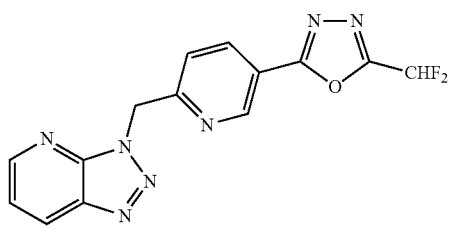 [SMILES: FC(F)c1nnc(-c2ccc(Cn3nnc4cccnc43)nc2)o1]

White solid; $^1$H NMR (δ ppm, 400 MHz, DMSO-d$_6$) 9.09 (d, J=2.2 Hz, 1H), 8.76 (dd, J=4.5, 1.4 Hz, 1H), 8.65 (dd, J=8.3, 1.4 Hz, 1H), 8.47 (dd, J=8.2, 2.3 Hz, 1H), 7.65 (d, J=8.2 Hz, 1H), 7.57-7.53 (m, 1H), 7.57 (t, J=51.1 Hz, 1H), 6.25 (s, 2H), regiochemistry was confirmed by an nOe enhancement between the protons at 6.25 ppm and 7.65 ppm only; MS (ESI, m/z): 330.20 [M+1]$^+$.

Example 24: 2-(6-((5,6-dichloro-1H-benzo[d][1,2,3]triazol-1-yl)methyl)pyridin-3-yl)-5-(difluoromethyl)-1,3,4-oxadiazole

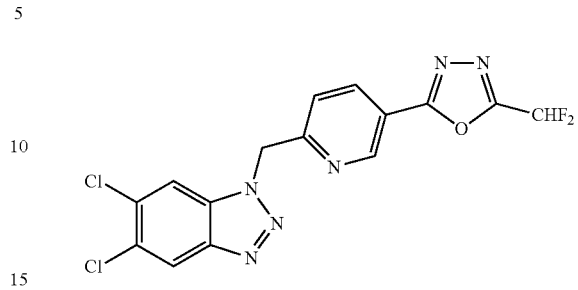

White solid; $^1$H NMR (δ ppm, 400 MHz, DMSO-d$_6$) 9.11 (d, J=2.2 Hz, 1H), 8.55 (s, 1H), 8.48 (dd, J=8.2, 2.3 Hz, 1H), 8.40 (s, 1H), 7.65 (d, J=8.2 Hz, 1H), 7.58 (t, J=51.2 Hz, 1H), 6.29 (s, 2H), regiochemistry was confirmed by nOe enhancement between the proton at 6.29 ppm and the protons at 8.40 ppm; MS (ESI, m/z): 397.20 and 399.16 [M+1]$^+$.

Example 25: 2-(6-((5,6-dichloro-2H-benzo[d][1,2,3]triazol-2-yl)methyl)pyridin-3-yl)-5-(difluoromethyl)-1,3,4-oxadiazole

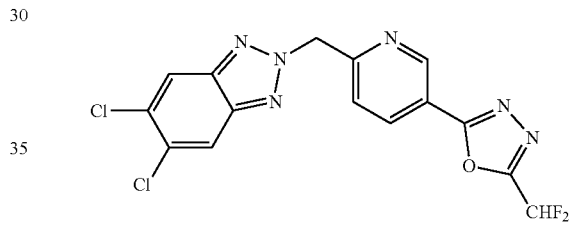

White solid; $^1$H NMR (δ ppm, 400 MHz, DMSO-d$_6$) 9.16 (d, J=2.2 Hz, 1H), 8.50 (dd, J=8.1, 2.3 Hz, 1H), 8.45 (s, 2H), 7.65 (d, J=8.3 Hz, 1H), 7.59 (t, J=51.2 Hz, 1H), 6.30 (s, 2H), regiochemistry was confirmed by an nOe enhancement between the protons at 6.30 ppm and 7.65 ppm only; MS (ESI, m/z): 397.22 and 399.20 [M+1]$^+$.

Example 26: 2-(difluoromethyl)-5-(6-((4-phenyl-1H-imidazol-1-yl)methyl)pyridin-3-yl)-1,3,4-oxadiazole

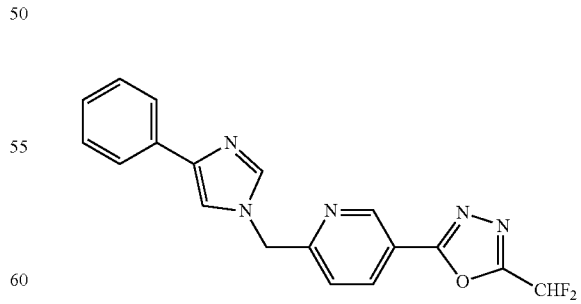

White solid; $^1$H NMR (δ ppm, 400 MHz, CDCl$_3$-d) 9.35 (d, J=2.2 Hz, 1H), 8.40 (dd, J=8.2, 2.3 Hz, 1H), 7.84-7.78 (m, 2H), 7.75 (s, 1H), 7.40 (t, J=7.6 Hz, 2H), 7.30-7.27 (m, 1H), 7.33 (s, 1H), 7.23 (d, J=8.2 Hz, 1H), 6.96 (t, J=51.6 Hz, 1H), 5.41 (s, 2H), regiochemistry was confirmed by nOe enhancement between the proton at 5.41 ppm and the protons at 7.23 ppm, 7.33 ppm and 7.75 ppm; MS (ESI, m/z): 354.26 [M+1]+.

Example 58: 2-(6-((5,6-dichloro-2-(trifluoromethyl)-1H-benzo[d]imidazol-1-yl)methyl)pyridin-3-yl)-5-(difluoromethyl)-1,3,4-oxadiazole

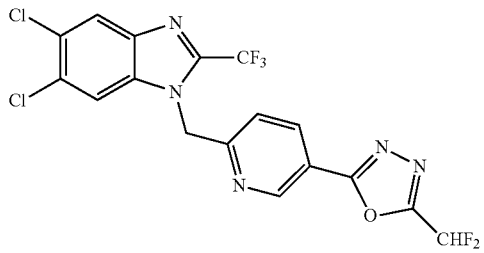 [SMILES: FC(F)c1nnc(-c2ccc(Cn3c(C(F)(F)F)nc4cc(Cl)c(Cl)cc43)nc2)o1]

White solid; 1H NMR (δ ppm, 400 MHz, CDCl3-d) 9.05-9.03 (m, 1H), 8.48 (dd, J=8.2, 2.2 Hz, 1H), 8.30 (s, 1H), 8.27 (s, 1H), 7.67 (d, J=8.3 Hz, 1H), 7.57 (t, J=51.2 Hz, 1H), 6.01 (s, 2H); MS (ESI, m/z): 464.19 and 466.19 [M+1]+.

Example 59: 2-(difluoromethyl)-5-(6-((5,6-dimethyl-1H-benzo[d][1,2,3]triazol-1-yl)methyl)pyridin-3-yl)-1,3,4-oxadiazole

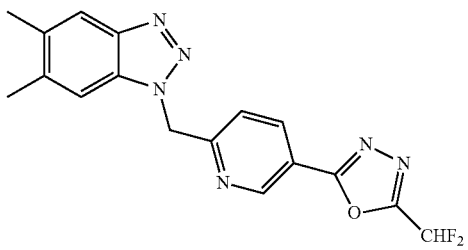 [SMILES: Cc1cc2nnn(Cc3ccc(-c4nnc(C(F)F)o4)cn3)c2cc1C]

White solid; 1H NMR (δ ppm, 400 MHz, CDCl3-d) 9.14 (d, J=2.3 Hz, 1H), 8.45 (dd, J=8.2, 2.3 Hz, 1H), 7.84 (s, 1H), 7.59 (s, 1H), 7.57 (t, J=51.3 Hz, 1H), 7.46 (d, J=8.4 Hz, 1H), 6.18 (s, 2H), 2.37 (d, J=4.3 Hz, 6H); MS (ESI, m/z): 357.24 [M+1]+.

Example 60: 2-(6-((5,6-dichloro-2-methyl-1H-benzo[d]imidazol-1-yl)methyl)pyridin-3-yl)-5-(difluoromethyl)-1,3,4-oxadiazole

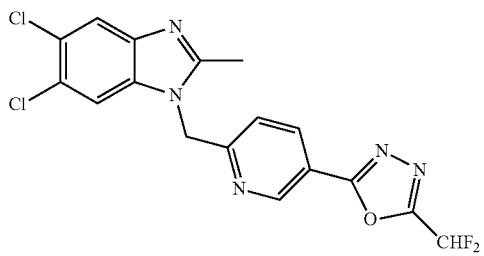 [SMILES: Cc1nc2cc(Cl)c(Cl)cc2n1Cc1ccc(-c2nnc(C(F)F)o2)cn1]

Yellow oil; 1H NMR (δ ppm, 400 MHz, CDCl3-d) 9.34 (dd, J=2.2, 0.8 Hz, 1H), 8.38 (dd, J=8.2, 2.2 Hz, 1H), 7.84 (s, 1H), 7.36 (s, 1H), 7.09-7.05 (m, 1H), 6.96 (t, J=51.6 Hz, 1H), 5.50 (s, 2H), 2.67 (s, 3H); MS (ESI, m/z): 410.23 and 412.23 [M+1]+.

Example 61: 2-(difluoromethyl)-5-(6-((5,6-dimethyl-1H-benzo[d]imidazol-1-yl)methyl)pyridin-3-yl)-1,3,4-oxadiazole

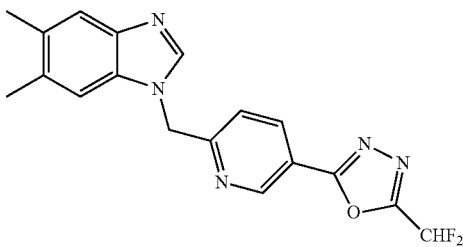

Brown solid; 1H NMR (δ ppm, 400 MHz, CDCl3-d) 9.36 (d, J=2.1 Hz, 1H), 8.32 (dd, J=8.2, 2.2 Hz, 1H), 8.07 (s, 1H), 7.65 (s, 1H), 7.09-7.05 (m, 2H), 6.96 (t, J=51.6 Hz, 1H), 5.59 (s, 2H), 2.40 (s, 3H), 2.36 (s, 3H); MS (ESI, m/z): 356.26 [M+1]+.

Example 62 2-(6-((6-bromo-1H-benzo[d]imidazol-1-yl)methyl)pyridin-3-yl)-5-(difluoromethyl)-1,3,4-oxadiazole, and Example 63: 2-(6-((5-bromo-1H-benzo[d]imidazol-1-yl)methyl)pyridin-3-yl)-5-(difluoromethyl)-1,3,4-oxadiazole

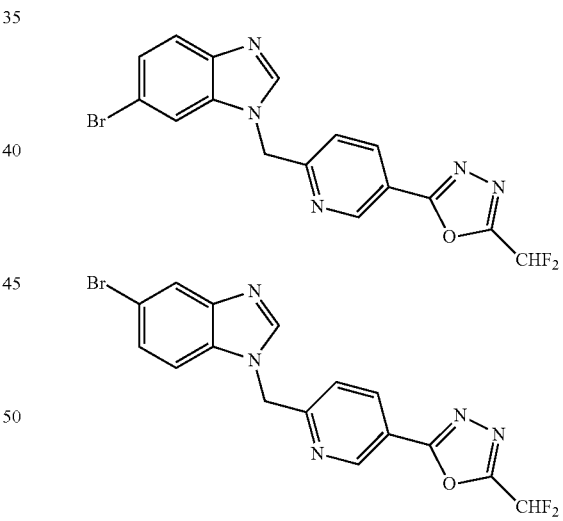

Two enriched fractions were obtained. Fraction 1: Yellow oil; Mix of two regioisomers (distribution 1st eluted compound: 2nd eluted compound 37:63); MS (ESI, m/z): 406.17 and 408.17 [M+1]+ 1st eluted compound and 406.17 and 408.17 [M+1]+ 2nd eluted compound.

Fraction 2: Yellow oil; Mix of two regioisomers (distribution 1st eluted compound: 2nd eluted compound 62:38); MS (ESI, m/z): 406.17 and 408.17 [M+1]+ 1st eluted compound and 406.17 and 408.17 [M+1]+ 2nd eluted compound.

Examples 57 and 58 can be separated by standard methods in the art such as by silica column chromatography, however, they are herein presented as their enriched mixtures since this is how they were tested in the biological assays referred to hereinbelow.

Example 64: 2-(6-((5-bromo-1H-benzo[d][1,2,3] triazol-1-yl)methyl)pyridin-3-yl)-5-(difluoromethyl)-1,3,4-oxadiazole

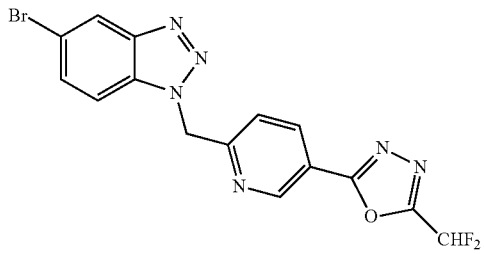 [SMILES: FC(F)c1nnc(-c2ccc(Cn3nnc4cc(Br)ccc43)nc2)o1]

Yellow oil; $^1$H NMR (δ ppm, 400 MHz, CDCl$_3$-d) 9.33 (d, J=2.0 Hz, 1H), 8.38 (dd, J=8.2, 2.2 Hz, 1H), 8.28 (dd, J=1.7, 0.7 Hz, 1H), 7.60 (dd, J=8.8, 1.6 Hz, 1H), 7.49 (dd, J=8.7, 0.7 Hz, 1H), 7.33 (d, J=8.2 Hz, 1H), 6.95 (t, J=51.6 Hz, 1H), 6.07 (s, 2H), regiochemistry was confirmed by nOe enhancement between the proton at 6.07 ppm and the protons at 7.33 ppm and 7.49 ppm; MS (ESI, m/z): 407.18 and 409.18 [M+1]$^+$.

Example 65: 2-(6-((6-bromo-1H-benzo[d][1,2,3] triazol-1-yl)methyl)pyridin-3-yl)-5-(difluoromethyl)-1,3,4-oxadiazole

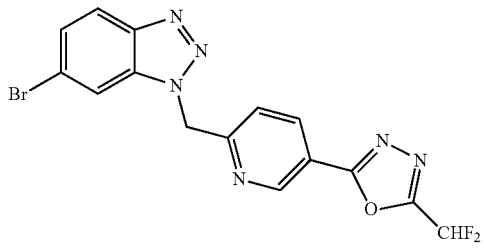 [SMILES: FC(F)c1nnc(-c2ccc(Cn3nnc4ccc(Br)cc43)nc2)o1]

Yellow oil; $^1$H NMR (δ ppm, 400 MHz, CDCl$_3$-d) 9.35 (s, 1H), 8.39 (dd, J=8.2, 2.1 Hz, 1H), 7.99 (d, J=8.8 Hz, 1H), 7.79 (d, J=1.8 Hz, 1H), 7.52 (dd, J=8.8, 1.6 Hz, 1H), 7.34 (d, J=8.2 Hz, 1H), 6.95 (t, J=51.6 Hz, 1H), 6.05 (s, 2H), regiochemistry was confirmed by nOe enhancement between the proton at 6.05 ppm and the protons at 7.34 ppm and 7.79 ppm; MS (ESI, m/z): 407.18 and 409.18 [M+1]$^+$.

Example 66: 2-(6-((5-bromo-2H-benzo[d][1,2,3] triazol-2-yl)methyl)pyridin-3-yl)-5-(difluoromethyl)-1,3,4-oxadiazole

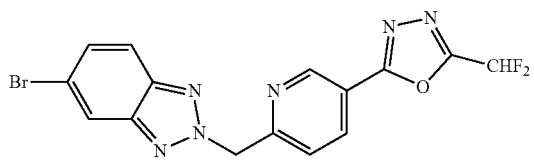 [SMILES: FC(F)c1nnc(-c2ccc(Cn3nc4ccc(Br)cc4n3)nc2)o1]

Yellow oil; $^1$H NMR (δ ppm, 400 MHz, CDCl$_3$-d) 9.34 (d, J=2.1 Hz, 1H), 8.40 (dd, J=8.2, 2.2 Hz, 1H), 8.11 (d, J=1.7 Hz, 1H), 7.81 (dd, J=9.0, 0.8 Hz, 1H), 7.53 (dd, J=9.1, 1.7 Hz, 1H), 7.31 (d, J=8.2 Hz, 1H), 6.95 (t, J=51.7 Hz, 1H), 6.15 (s, 2H), regiochemistry was confirmed by an nOe enhancement between the protons at 6.15 ppm and 7.31 ppm only; MS (ESI, m/z): 407.18 and 409.18 [M+1]$^+$.

B) Examples Synthesized According to Method B of the Present Invention

Compounds of formula (I) were synthesized by applying the following synthetic protocol:

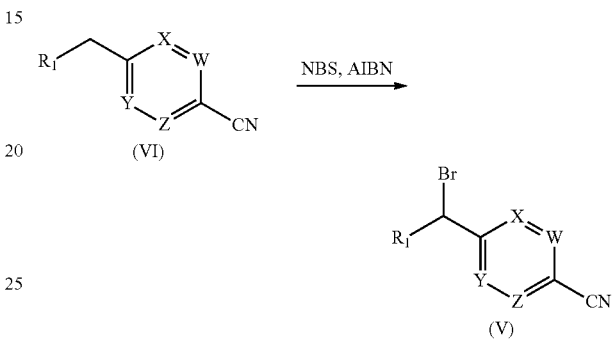

To a solution of the corresponding alkaryl compound (15.6 mmol) in acetonitrile, N-bromosuccinimide (NBS) (15.6 mmol, 2.37 g) and azobisisobutyronitrile (AIBN) (1.56 mmol, 0.256 g) were added. The reaction mixture was refluxed for 2 hours and azobisisobutyronitrile (0.78 mmol, 0.128 g) was added again. After one hour refluxing, the mixture was allowed to stir for 16 hours at room temperature. Then, solvent was evaporated under reduced pressure, and the crude thus obtained was purified by flash chromatography (silica gel, ethyl acetate/hexane) to afford the bromide compound.

Where all of W, X, Y and Z are CH

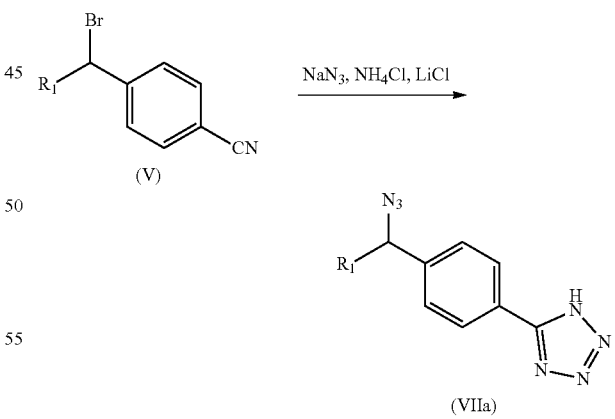

To a solution of the corresponding bromide compound (1.0 mmol) in N,N-dimethylformamide (DMF) at room temperature, NaN$_3$ (4.7 mmol, 0.305 g), NH$_4$Cl (4.7 mmol, 0.251 g) and LiCl (1.7 mmol, 0.071 g) were subsequently added. The reaction mixture was stirred at 100° C. and monitored by TLC until the completion of the reaction. Then, ethyl acetate was added, and the organic layer was washed with water, dried over sodium sulfate, filtered and evaporated under reduced pressure. The crude thus obtained was used without further purification.

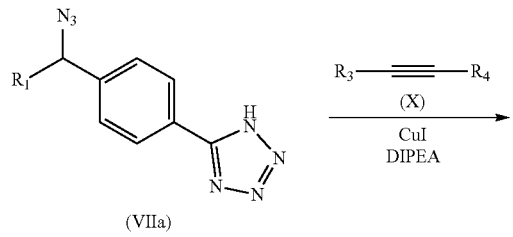

(VIIa)

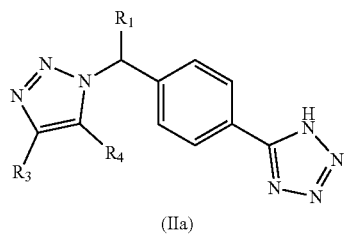

(IIa)

To a solution of the corresponding alkyne (0.5 mmol), the azide compound (0.5 mmol) and CuI (0.22 mmol, 0.041 g) in N,N-dimethylformamide at room temperature, N,N-diisopropylethylamine (DIPEA) (2.8 mmol, 0.5 ml) was added. The reaction mixture was stirred and monitored by HPLC-MS. Upon the completion of the reaction, ethyl acetate was added. Then, the organic layer was washed with NH$_3$/H$_2$O (×2) and brine, dried over Na$_2$SO$_4$, filtered and evaporated under reduced pressure. The crude thus obtained was purified by flash chromatography (silica gel, ethyl acetate/hexane) to afford the desired product.

Where one or two of W, X, Y or Z is N (pyridine exemplified)

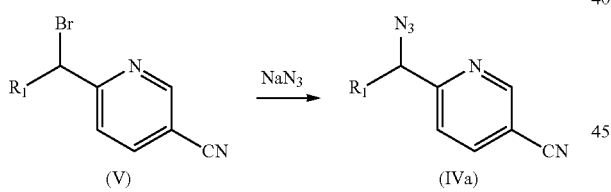

To a solution of the corresponding bromide compound (1.0 mmol) in N,N-dimethylformamide, NaN$_3$ was added. The reaction mixture was stirred at room temperature for 5 hours. Then, ethyl acetate was added and the organic layer was washed with water and brine, dried over sodium sulfate, filtered and evaporated under reduce pressure. The crude thus obtained was used without further purification.

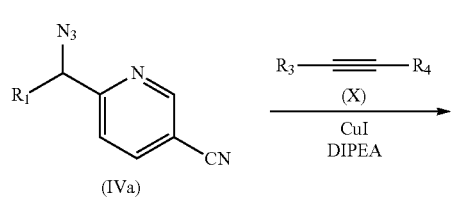

(IVa)

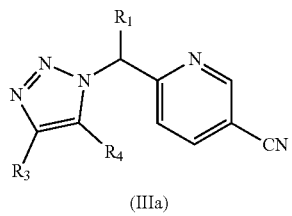

(IIIa)

To a solution of the corresponding alkyne (0.5 mmol), the azido compound (0.5 mmol) and CuI (0.22 mmol, 0.041 g) in N,N-dimethylformamide at room temperature, N,N-diisopropylethylamine (DIPEA) (2.8 mmol, 0.5 ml) was added. The reaction mixture was stirred and monitored by HPLC-MS. Upon the completion of the reaction, ethyl acetate was added. Then, the organic layer was washed with NH$_3$/H$_2$O (×2) and brine, dried over Na$_2$SO$_4$, filtered and evaporated under reduced pressure. The crude thus obtained was purified by flash chromatography (silica gel, ethyl acetate/hexane) to afford the desired product.

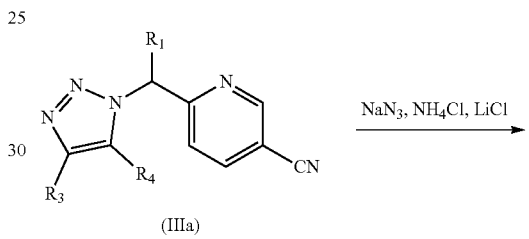

(IIIa)

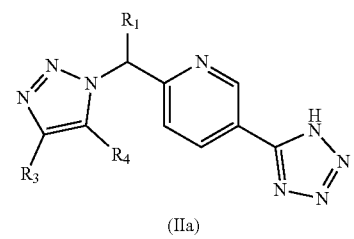

(IIa)

To a solution of the corresponding nitrile compound (1.0 mmol) in N,N-dimethylformamide at room temperature, NaN$_3$ (4.7 mmol, 0.305 g), NH$_4$Cl (4.7 mmol, 0.251 g) and LiCl (1.7 mmol, 0.071 g) were subsequently added. The reaction mixture was stirred at 100° C. and monitored by TLC until the completion of the reaction. The crude thus obtained was used without further purification.

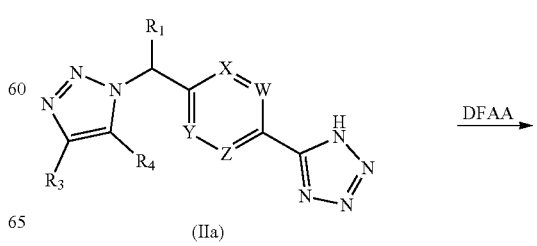

(IIa)

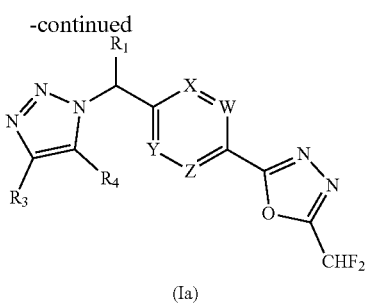

(Ia)

To the crude reaction obtained in the previous step, difluoroacetic anhydride (DFAA) (20.0 mmol, 2.5 ml) was added at room temperature. The reaction mixture was stirred at 60° C. (when one or two of W, X, Y or Z were N) or 100° C. (when W, X, Y and Z were each CH). The progress of the reaction was monitored by HPLC-MS. After the completion of the reaction, water was added and this solution was extracted with ethyl acetate. The combined organic fractions were washed with water and brine, dried over $Na_2SO_4$ and evaporated under reduced pressure. The crude thus obtained was purified by flash chromatography (silica gel, ethyl acetate/hexane) to afford the desired product with high purity (>90%).

Representative examples prepared by employing this protocol were:

Example 27: 2-(difluoromethyl)-5-(4-((4-phenyl-1H-1,2,3-triazol-1-yl)methyl)phenyl)-1,3,4-oxadiazole

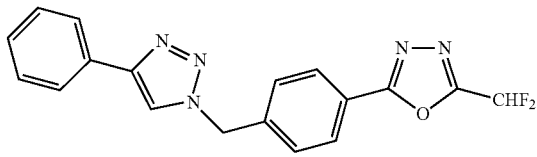 [SMILES: FC(F)c1nnc(-c2ccc(Cn3cc(-c4ccccc4)nn3)cc2)o1]

White solid; $^1$H NMR (δ ppm, 400 MHz, DMSO-d$_6$) 8.72 (s, 1H), 8.10 (d, J=8.3 Hz, 2H), 7.87 (d, J=7.1 Hz, 2H), 7.58 (d, J=8.2 Hz, 2H), 7.56 (t, J=51.3 Hz, 1H), 7.46 (dd, J=8.3, 7.0 Hz, 2H), 7.38-7.33 (m, 1H), 5.82 (s, 2H); MS (ESI, m/z): 354.30 [M+1]$^+$.

Example 28: methyl 1-(4-(5-(difluoromethyl)-1,3,4-oxadiazol-2-yl)benzyl)-1H-1,2,3-triazole-4-carboxylate

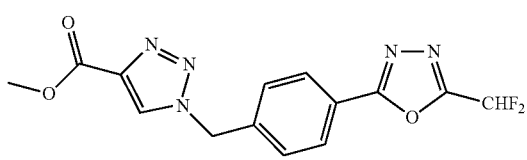 [SMILES: COC(=O)c1cn(Cc2ccc(-c3nnc(C(F)F)o3)cc2)nn1]

White solid; $^1$H NMR (δ ppm, 400 MHz, DMSO-d$_6$) 8.96 (s, 1H), 7.88 (d, J=8.3 Hz, 2H), 7.56 (t, J=52.6 Hz, 1H), 7.50 (d, J=8.3 Hz, 2H), 5.80 (s, 2H), 3.84 (s, 3H); MS (ESI, m/z): 336.26 [M+1]$^+$.

Example 29: 2-(4-((4-(4-chlorophenyl)-1H-1,2,3-triazol-1-yl)methyl)phenyl)-5-(difluoromethyl)-1,3,4-oxadiazole

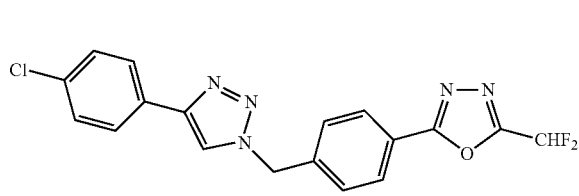 [SMILES: FC(F)c1nnc(-c2ccc(Cn3cc(-c4ccc(Cl)cc4)nn3)cc2)o1]

White solid; $^1$H NMR (δ ppm, 400 MHz, DMSO-d$_6$) 8.77 (s, 1H), 8.10 (d, J=8.3 Hz, 2H), 7.90 (d, J=8.6 Hz, 2H), 7.58 (d, J=8.2 Hz, 2H), 7.56 (t, J=51.3 Hz, 1H), 7.53 (d, J=8.6 Hz, 2H), 5.82 (s, 2H); MS (ESI, m/z): 388.24 and 390.27 [M+1]$^+$.

Example 30: 2-(difluoromethyl)-5-(4-((4-(4-(trifluoromethyl)phenyl)-1H-1,2,3-triazol-1-yl)methyl)phenyl)-1,3,4-oxadiazole

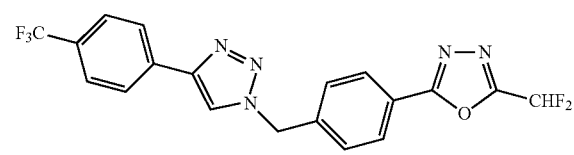 [SMILES: FC(F)c1nnc(-c2ccc(Cn3cc(-c4ccc(C(F)(F)F)cc4)nn3)cc2)o1]

White solid; $^1$H NMR (δ ppm, 400 MHz, DMSO-d$_6$) 8.90 (s, 1H), 8.12-8.09 (m, 4H), 7.83 (d, J=8.2 Hz, 2H), 7.60 (d, J=8.3 Hz, 2H), 7.56 (t, J=51.3 Hz, 1H), 5.85 (s, 2H); MS (ESI, m/z): 422.31 [M+1]$^+$.

Example 31: 2-(4-((4-(tert-butyl)-1H-1,2,3-triazol-1-yl)methyl)phenyl)-5-(difluoromethyl)-1,3,4-oxadiazole

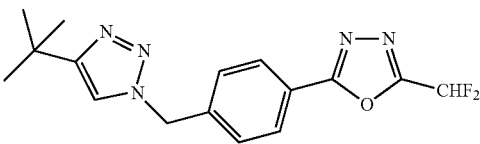 [SMILES: CC(C)(C)c1cn(Cc2ccc(-c3nnc(C(F)F)o3)cc2)nn1]

White solid; $^1$H NMR (δ ppm, 400 MHz, DMSO-d$_6$) 8.09 (d, J=8.3 Hz, 2H), 7.99 (s, 1H), 7.56 (t, J=51.4 Hz, 1H), 7.54 (d, J=8.3 Hz, 2H), 5.68 (s, 2H), 1.28 (s, 9H); MS (ESI, m/z): 334.02 [M+1]$^+$.

Example 32: 2-(4-((4-cyclohexyl-1H-1,2,3-triazol-1-yl)methyl)phenyl)-5-(difluoromethyl)-1,3,4-oxadiazole

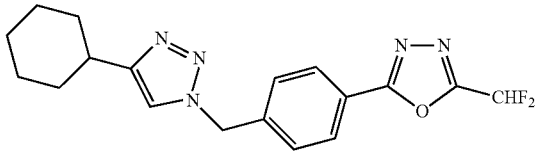 [SMILES: FC(F)c1nnc(-c2ccc(Cn3cc(C4CCCCC4)nn3)cc2)o1]

White solid; ¹H NMR (δ ppm, 400 MHz, DMSO-d₆) 8.08 (d, J=8.3 Hz, 2H), 7.97 (s, 1H), 7.56 (t, J=51.4 Hz, 1H), 7.51 (d, J=8.3 Hz, 2H), 5.68 (s, 2H), 2.72-2.63 (m, 1H), 2.01-1.89 (m, 2H), 1.76-1.72 (m, 2H), 1.75-1.66 (m, 1H), 1.43-1.30 (m, 4H), 1.27-1.16 (m, 1H); MS (ESI, m/z): 360.57 [M+1]⁺.

Example 33: 2-(difluoromethyl)-5-(4-((4-(pyridin-4-yl)-1H-1,2,3-triazol-1-yl)methyl)phenyl)-1,3,4-oxadiazole

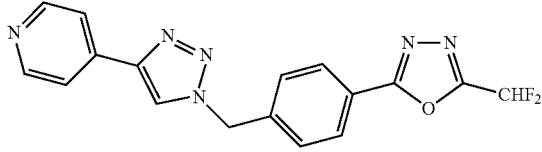 [SMILES: FC(F)c1nnc(-c2ccc(Cn3cc(-c4ccncc4)nn3)cc2)o1]

White solid; ¹H NMR (δ ppm, 400 MHz, DMSO-d₆) 8.95 (s, 1H), 8.65 (d, J=5.8 Hz, 2H), 8.11 (d, J=8.3 Hz, 2H), 7.84 (d, J=6.1 Hz, 2H), 7.59 (d, J=8.2 Hz, 2H), 7.56 (t, J=51.3 Hz, 1H), 5.86 (s, 2H); MS (ESI, m/z): 355.00 [M+1]⁺.

Example 34: 2-(difluoromethyl)-5-(4-((4-(pyridin-3-yl)-1H-1,2,3-triazol-1-yl)methyl)phenyl)-1,3,4-oxadiazole

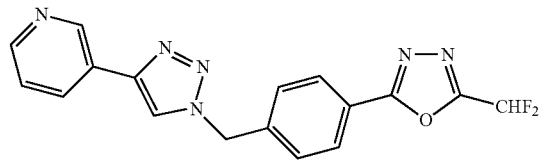 [SMILES: FC(F)c1nnc(-c2ccc(Cn3cc(-c4cccnc4)nn3)cc2)o1]

Yellow solid; ¹H NMR (δ ppm, 400 MHz, DMSO-d₆) 9.08 (s, 1H), 8.85 (s, 1H), 8.56 (d, J=4.8 Hz, 1H), 8.24 (dt, J=7.9, 2.0 Hz, 1H), 8.11 (d, J=8.3 Hz, 2H), 7.59 (d, J=8.3 Hz, 2H), 7.56 (t, J=51.3 Hz, 1H), 7.50 (dd, J=8.0, 4.8 Hz, 1H), 5.85 (s, 2H); MS (ESI, m/z): 355.25 [M+1]⁺.

Example 35: 2-(difluoromethyl)-5-(4-((4-(thiophen-3-yl)-1H-1,2,3-triazol-1-yl)methyl)phenyl)-1,3,4-oxadiazole

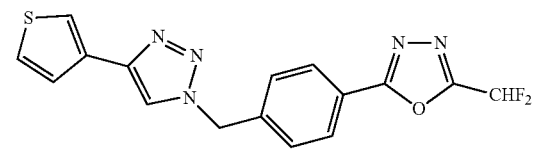 [SMILES: FC(F)c1nnc(-c2ccc(Cn3cc(-c4ccsc4)nn3)cc2)o1]

White solid; ¹H NMR (δ ppm, 400 MHz, DMSO-d₆) 8.56 (s, 1H), 8.10 (d, J=8.3 Hz, 2H), 7.88 (dd, J=2.9, 1.2 Hz, 1H), 7.66 (dd, J=5.0, 2.9 Hz, 1H), 7.56 (t, J=51.4 Hz, 1H), 7.55 (d, J=8.3 Hz, 2H), 7.53 (dd, J=5.1, 1.3 Hz, 1H), 5.80 (s, 2H); MS (ESI, m/z): 360.22 [M+1]⁺.

Example 36: 2-(difluoromethyl)-5-(4-((4-(thiophen-2-yl)-1H-1,2,3-triazol-1-yl)methyl)phenyl)-1,3,4-oxadiazole

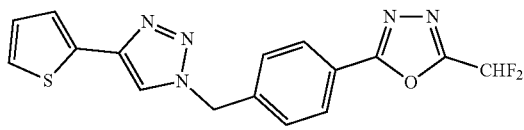 [SMILES: FC(F)c1nnc(-c2ccc(Cn3cc(-c4cccs4)nn3)cc2)o1]

White solid; ¹H NMR (δ ppm, 400 MHz, DMSO-d₆) 8.63 (s, 1H), 8.10 (d, J=8.3 Hz, 2H), 7.58-7.54 (m, 3H), 7.56 (t, J=51.5 Hz, 1H), 7.55 (d, J=1.2 Hz, 1H), 7.46 (dd, J=3.6, 1.1 Hz, 1H), 5.80 (s, 2H); MS (ESI, m/z): 360.22 [M+1]⁺.

Example 37: 2-(difluoromethyl)-5-(4-(1-(4-phenyl-1H-1,2,3-triazol-1-yl)ethyl)phenyl)-1,3,4-oxadiazole

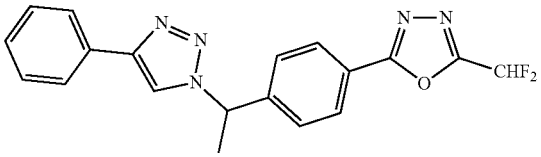 [SMILES: CC(c1ccc(-c2nnc(C(F)F)o2)cc1)n1cc(-c2ccccc2)nn1]

White solid; ¹H NMR (400 MHz, DMSO-d₆) δ 8.84 (s, 1H), 8.09 (d, J=8.4 Hz, 2H), 7.88 (d, J=7.1 Hz, 2H), 7.60 (d, J=8.4 Hz, 2H), 7.56 (t, J=51.4 Hz, 1H), 7.46 (t, J=7.6 Hz, 2H), 7.38-7.33 (m, 1H), 6.16 (q, J=7.1 Hz, 1H), 1.99 (d, J=7.1 Hz, 3H); MS (ESI, m/z): 368.29 [M+1]⁺.

Example 38: 2-(difluoromethyl)-5-(4-((4,5-diphenyl-1H-1,2,3-triazol-1-yl)methyl)phenyl)-1,3,4-oxadiazole

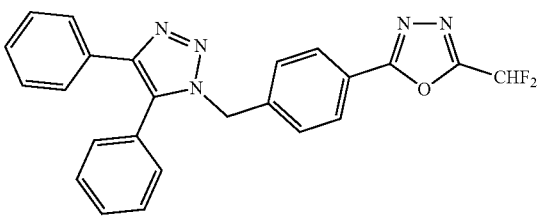 [SMILES: FC(F)c1nnc(-c2ccc(Cn3nnc(-c4ccccc4)c3-c3ccccc3)cc2)o1]

White solid; ¹H NMR (δ ppm, 400 MHz, CDCl₃-d) 8.08-8.01 (m, 2H), 7.62-7.57 (m, 2H), 7.56-7.50 (m, 2H), 7.49-7.43 (m, 2H), 7.33-7.27 (m, 2H), 7.23 (d, J=8.2 Hz, 2H), 7.20-7.16 (m, 2H), 6.93 (t, J=51.7 Hz, 1H), 5.53 (s, 2H); MS (ESI, m/z): 430.33 [M+1]⁺.

Example 39: 2-(difluoromethyl)-5-(4-((5-methyl-4-phenyl-1H-1,2,3-triazol-1-yl)methyl)phenyl)-1,3,4-oxadiazole

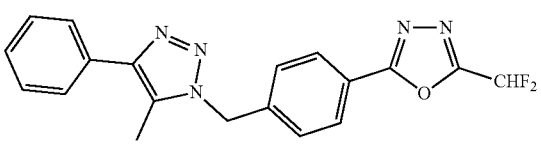 [SMILES: Cc1c(-c2ccccc2)nnn1Cc1ccc(-c2nnc(C(F)F)o2)cc1]

White solid; ¹H NMR (δ ppm, 400 MHz, CDCl₃-d) 8.18-8.12 (m, 2H), 7.75-7.72 (m, 2H), 7.51-7.46 (m, 2H), 7.41-7.37 (m, 3H), 6.94 (t, J=51.7 Hz, 1H), 5.68 (s, 2H), 2.40 (s, 3H), Regiochemistry was confirmed by nOe enhancement between the proton at 5.68 ppm and the protons at 2.40 ppm and 7.41 ppm; MS (ESI, m/z): 368.27 [M+1]⁺.

Example 40: 2-(difluoromethyl)-5-(4-((4-methyl-5-phenyl-1H-1,2,3-triazol-1-yl)methyl)phenyl)-1,3,4-oxadiazole

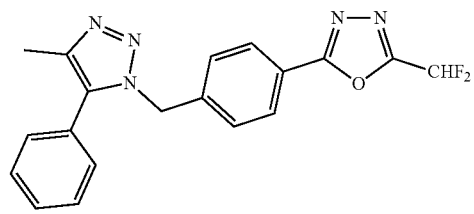 [SMILES: Cc1nnn(Cc2ccc(-c3nnc(C(F)F)o3)cc2)c1-c1ccccc1]

White solid; ¹H NMR (δ ppm, 400 MHz, CDCl₃-d) 8.06-8.02 (m, 2H), 7.49-7.45 (m, 3H), 7.22 (d, J=8.2 Hz, 2H), 7.16 (dd, J=7.4, 2.2 Hz, 2H), 6.93 (t, J=51.7 Hz, 1H), 5.55 (s, 2H), 2.35 (s, 3H); MS (ESI, m/z): 368.27 [M+1]⁺.

Example 41: 2-(difluoromethyl)-5-(6-((4-phenyl-1H-1,2,3-triazol-1-yl)methyl)pyridin-3-yl)-1,3,4-oxadiazole

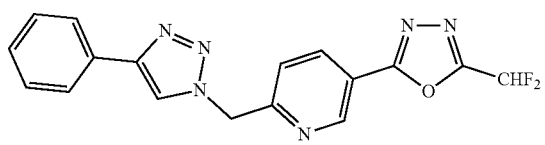 [SMILES: FC(F)c1nnc(-c2ccc(Cn3cc(-c4ccccc4)nn3)nc2)o1]

White solid; ¹H NMR (δ ppm, 400 MHz, DMSO-d₆) 9.21 (d, J=2.2 Hz, 1H), 8.74 (s, 1H), 8.50 (dd, J=8.2, 2.3 Hz, 1H), 7.89 (dd, J=8.3, 1.3 Hz, 1H), 7.59 (t, J=51.4 Hz, 1H), 7.58 (d, J=8.5 Hz, 2H), 7.47 (t, J=7.6 Hz, 2H), 7.36 (t, J=7.4 Hz, 1H), 5.94 (s, 2H); MS (ESI, m/z): 355.25 [M+1]⁺.

Intermediates 6-(bromomethyl)nicotinonitrile

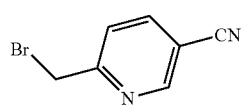

MS (ESI, m/z): 196.99 [M+1]⁺.

6-(azidomethyl)nicotinonitrile

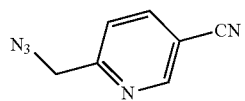 [SMILES: N#Cc1ccc(CN=[N+]=[N-])nc1]

MS (ESI, m/z): 160.02 [M+1]⁺.

6-((4-phenyl-1H-1,2,3-triazol-1-yl)methyl)nicotinonitrile, with the following structural

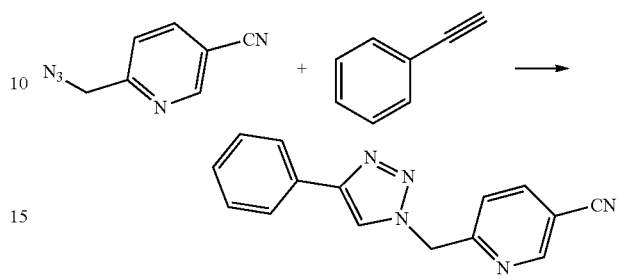

MS (ESI, m/z): 262.20 [M+1]⁺.

2-((4(4-phenyl-1H-1,2,3-triazol-1-yl)methyl)-5-(1H-tetrazol-5-yl)pyridine

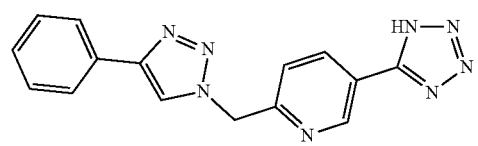 [SMILES: c1ccc(-c2cn(Cc3ccc(-c4nnn[nH]4)cn3)nn2)cc1]

MS (ESI, m/z): 305.23 [M+1]⁺.

Example 42: 2-(difluoromethyl)-5-(5-((4-phenyl-1H-1,2,3-triazol-1-yl)methyl)pyridin-2-yl)-1,3,4-oxadiazole

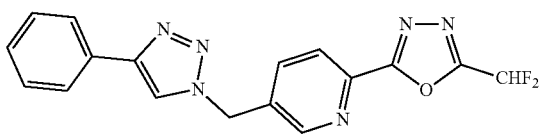 [SMILES: FC(F)c1nnc(-c2ccc(Cn3cc(-c4ccccc4)nn3)cn2)o1]

Yellow oil; ¹H NMR (δ ppm, 400 MHz, DMSO-d₆) 8.90 (d, J=2.1 Hz, 1H), 8.75 (s, 1H), 8.30 (d, J=8.1 Hz, 1H), 8.02 (dd, J=8.2, 2.2 Hz, 1H), 7.88-7.85 (m, 2H), 7.60 (t, J=51.3 Hz, 1H), 7.49-7.44 (m, 2H), 7.38-7.33 (m, 1H), 5.88 (s, 2H); MS (ESI, m/z): 355.25 [M+1]⁺.

Example 43: 2-(6-((4-(4-chlorophenyl)-1H-1,2,3-triazol-1-yl)methyl)pyridin-3-yl)-5-(difluoromethyl)-1,3,4-oxadiazole

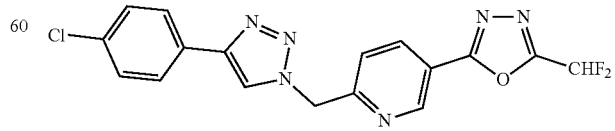

Yellow solid; ¹H NMR (δ ppm, 400 MHz, DMSO-d₆) 9.20 (d, J=2.2 Hz, 1H), 8.78 (s, 1H), 8.50 (dd, J=8.2, 2.3 Hz, 1H), 7.92 (d, J=8.5 Hz, 2H), 7.59 (t, J=51.3 Hz, 1H), 7.58 (d, J=8.1 Hz, 1H), 7.54 (d, J=8.5 Hz, 2H), 5.95 (s, 2H); MS (ESI, m/z): 389.25 and 391.21 [M+1]⁺.

Example 44: 2-(6-((4-(2-chlorophenyl)-1H-1,2,3-triazol-1-yl)methyl)pyridin-3-yl)-5-(difluoromethyl)-1,3,4-oxadiazole

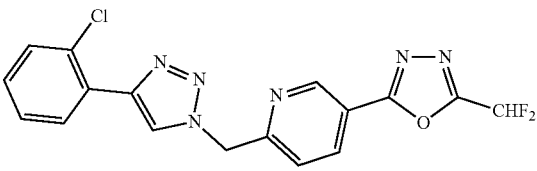

Yellow solid; ¹H NMR (δ ppm, 400 MHz, DMSO-d₆) 9.21 (s, 1H), 8.87 (s, 1H), 8.50 (dd, J=8.3, 2.3 Hz, 1H), 8.14 (d, J=7.8 Hz, 1H), 7.66-7.54 (m, 3H), 7.52-7.38 (m, 2H), 6.00 (s, 2H); MS (ESI, m/z): 389.25 and 391.25 [M+1]⁺.

Example 45: 2-(6-((4-(3-chlorophenyl)-1H-1,2,3-triazol-1-yl)methyl)pyridin-3-yl)-5-(difluoromethyl)-1,3,4-oxadiazole

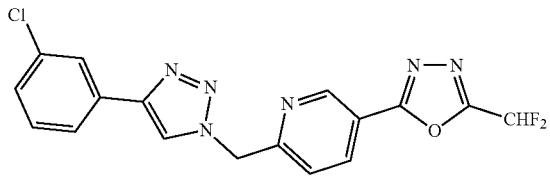 [SMILES: FC(F)c1nnc(-c2ccc(Cn3cc(-c4cccc(Cl)c4)nn3)nc2)o1]

Yellow solid; ¹H NMR (δ ppm, 400 MHz, DMSO-d₆) 9.21 (d, J=2.2 Hz, 1H), 8.83 (s, 1H), 8.51 (dd, J=8.2, 2.3 Hz, 1H), 7.95 (t, J=1.9 Hz, 1H), 7.89-7.85 (m, 1H), 7.61 (d, J=8.7 Hz, 1H), 7.59 (t, J=51.1 Hz, 1H), 7.53-7.40 (m, 2H), 5.95 (s, 2H); MS (ESI, m/z): 389.22 and 391.25 [M+1]⁺.

Example 46: 2-(6-((4-(3,4-dichlorophenyl)-1H-1,2,3-triazol-1-yl)methyl)pyridin-3-yl)-5-(difluoromethyl)-1,3,4-oxadiazole

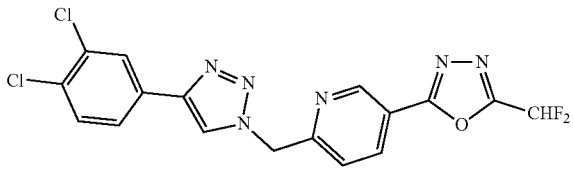

Yellow solid; ¹H NMR (δ ppm, 400 MHz, DMSO-d₆) 9.20 (d, J=2.2 Hz, 1H), 8.87 (s, 1H), 8.51 (dd, J=8.2, 2.3 Hz, 1H), 8.15 (d, J=2.0 Hz, 1H), 7.90 (dd, J=8.4, 2.0 Hz, 1H), 7.75 (d, J=8.4 Hz, 1H), 7.62 (d, J=8.2 Hz, 1H), 7.59 (t, J=51.2 Hz, 1H), 5.96 (s, 2H); MS (ESI, m/z): 423.22 and 425.22 [M+1]⁺.

Example 47: 2-(6-((4-(3,5-dichlorophenyl)-1H-1,2,3-triazol-1-yl)methyl)pyridin-3-yl)-5-(difluoromethyl)-1,3,4-oxadiazole

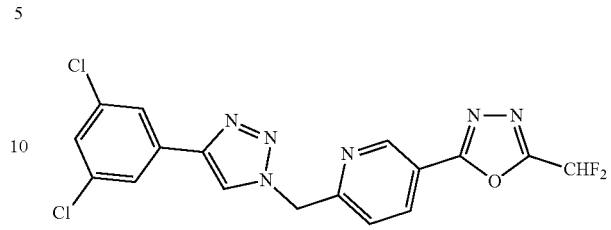

White solid; ¹H NMR (δ ppm, 400 MHz, DMSO-d₆) 9.21 (dd, J=2.3, 0.8 Hz, 1H), 8.91 (s, 1H), 8.51 (dd, J=8.2, 2.3 Hz, 1H), 7.96 (d, J=2.0 Hz, 2H), 7.64 (dd, J=8.2, 0.9 Hz, 1H), 7.61 (t, J=1.9 Hz, 1H), 7.59 (t, J=51.2 Hz, 1H), 5.96 (s, 2H). MS (ESI, m/z): 423.26 and 425.28 [M+1]⁺.

Example 48: 2-(difluoromethyl)-5-(6-((4-(2-fluorophenyl)-1H-1,2,3-triazol-1-yl)methyl)pyridin-3-yl)-1,3,4-oxadiazole

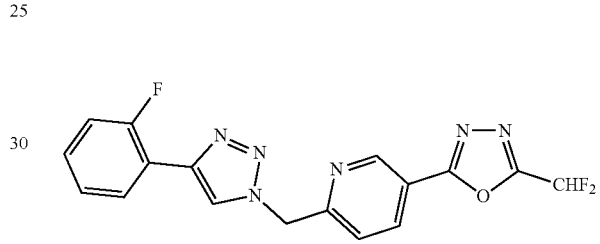

Yellow solid; ¹H NMR (δ ppm, 400 MHz, DMSO-d₆) 9.20 (dd, J=2.3, 0.8 Hz, 1H), 8.64 (d, J=3.8 Hz, 1H), 8.49 (dd, J=8.2, 2.3 Hz, 1H), 8.18 (td, J=7.6, 1.7 Hz, 1H), 7.65 (t, J=51.3 Hz, 1H), 7.56 (d, J=8.2 Hz, 1H), 7.45-7.33 (m, 3H), 5.99 (s, 2H); MS (ESI, m/z): 373.21 [M+1]⁺.

Example 49: 2-(difluoromethyl)-5-(6-((4-(2,6-difluorophenyl)-1H-1,2,3-triazol-1-yl)methyl)pyridin-3-yl)-1,3,4-oxadiazole

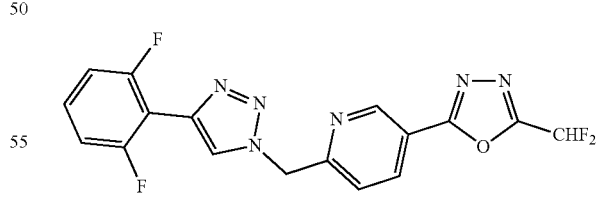

Brown solid; ¹H NMR (δ ppm, 400 MHz, DMSO-d₆) 9.21 (d, J=2.2 Hz, 1H), 8.66 (t, J=1.5 Hz, 1H), 8.51 (dd, J=8.2, 2.3 Hz, 1H), 7.59 (d, J=8.2 Hz, 1H)), 7.59 (t, J=51.2 Hz, 1H), 7.52 (tt, J=8.5, 6.4 Hz, 1H), 7.28 (t, J=8.4 Hz, 2H), 6.00 (s, 2H); MS (ESI, m/z): 391.28 [M+1]⁺.

Example 50: 2-(6-((4-(3-chlorophenyl)-1H-1,2,3-triazol-1-yl)methyl)pyridin-3-yl)-5-(difluoromethyl)-1,3,4-oxadiazole

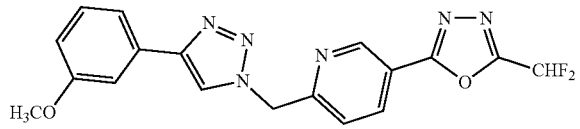 [SMILES: COc1cccc(-c2cn(Cc3ccc(-c4nnc(C(F)F)o4)cn3)nn2)c1]

White solid; $^1$H NMR (δ ppm, 400 MHz, DMSO-$d_6$) 9.21 (d, J=2.2 Hz, 1H), 8.75 (s, 1H), 8.50 (dd, J=8.2, 2.3 Hz, 1H), 7.59 (t, J=51.4 Hz, 1H), 7.58 (d, J=9.0 Hz, 1H), 7.48 (t, J=1.3 Hz, 1H), 7.46 (dt, J=3.4, 1.8 Hz, 1H), 7.38 (t, J=7.9 Hz, 1H), 6.93 (ddd, J=8.2, 2.6, 1.1 Hz, 1H), 5.94 (s, 2H), 3.82 (s, 3H); MS (ESI, m/z): 385.33 [M+1]$^+$.

Example 56: 2-(difluoromethyl)-5-(6-((4-(3,5-difluorophenyl)-1H-1,2,3-triazol-1-yl)methyl)pyridin-3-yl)-1,3,4-oxadiazole

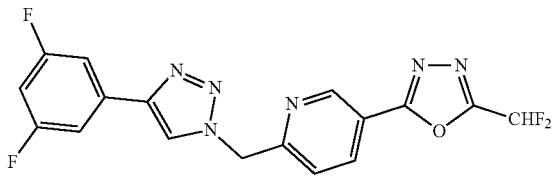 [SMILES: Fc1cc(F)cc(-c2cn(Cc3ccc(-c4nnc(C(F)F)o4)cn3)nn2)c1]

White solid; $^1$H NMR (δ ppm, 400 MHz, CDCl$_3$-d) 9.20 (d, J=2.3 Hz, 1H), 8.86 (s, 1H), 8.51 (dd, J=8.2, 2.3 Hz, 1H), 7.65-7.61 (m, 3H), 7.59 (t, J=51.3 Hz, 1H), 7.30-7.20 (m, 1H), 5.97 (s, 2H); MS (ESI, m/z): 391.25 [M+1]$^+$.

Example 57: 2-(difluoromethyl)-5-(6-((4-(3,4,5-trifluorophenyl)-1H-1,2,3-triazol-1-yl)methyl)pyridin-3-yl)-1,3,4-oxadiazole

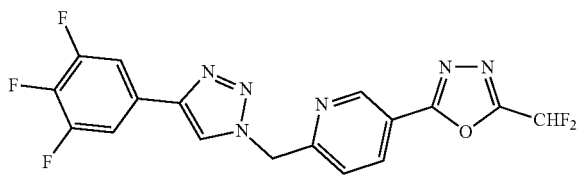 [SMILES: Fc1cc(-c2cn(Cc3ccc(-c4nnc(C(F)F)o4)cn3)nn2)cc(F)c1F]

White solid; $^1$H NMR (δ ppm, 400 MHz, CDCl$_3$-d) 9.20 (d, J=2.1 Hz, 1H), 8.82 (s, 1H), 8.51 (dd, J=8.2, 2.3 Hz, 1H), 7.85 (dd, J=9.0, 6.7 Hz, 2H), 7.63 (d, J=8.2 Hz, 1H), 7.59 (t, J=51.2 Hz, 1H), 5.97 (s, 2H); MS (ESI, m/z): 409.25 [M+1]$^+$.

C) Examples Synthesized According to Method C of the Present Invention

Compounds of formula (I) were synthesized by applying the following synthetic protocol:

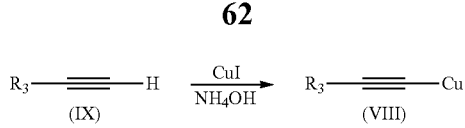

CuI (2.5 mmol, 0.500 g) was dissolved in ammonium hydroxide. While stirring, the corresponding arylacetylene was added dropwise. After 15 min, the yellow precipitate formed was filtered and washed with water, EtOH and Et$_2$O.

Where all of W, X, Y and Z are CH

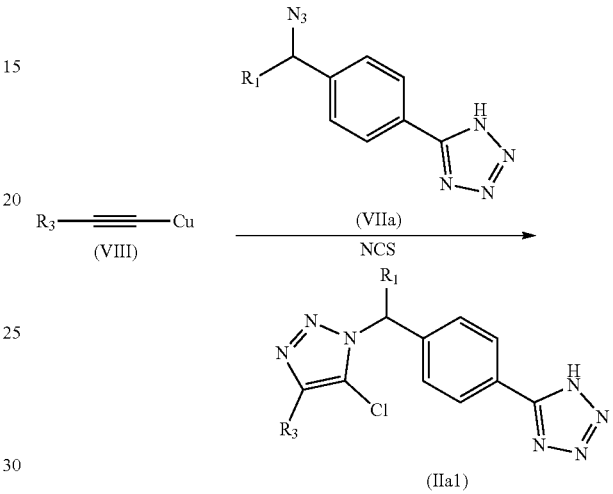

To a solution of the corresponding copper (I) arylacetylide (0.5 mmol) and the corresponding azide compound (synthesised as described for method B; 0.6 mmol) in CH$_2$Cl$_2$ (1 ml), N-chlorosuccinimide (0.6 mmol, 0.080 g) was added. The mixture was stirred at room temperature and monitored by HPLC-MS. Upon the completion of the reaction, dichloromethane was evaporated under reduced pressure and, the crude thus obtained was purified by flash chromatography (silica gel, ethyl acetate/hexane) to afford the desired product.

Where one or two of W, X, Y or Z is N (pyridine exemplified)

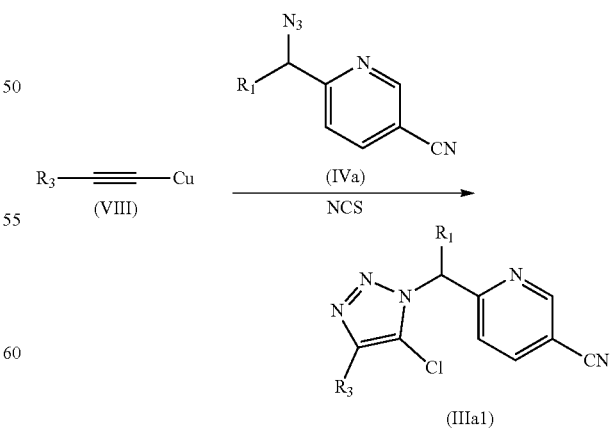

To a solution of the corresponding copper (I) arylacetylide (0.5 mmol) and the corresponding azide derivative (synthesised as described for method B; 0.6 mmol) in CH$_2$Cl$_2$ (1 ml), N-chlorosuccinimide (0.6 mmol, 0.080 g) was added. The mixture was stirred at room temperature and monitored by HPLC-MS. Upon the completion of the reaction, dichloromethane was evaporated under reduced pressure and, the crude thus obtained was purified by flash chromatography (silica gel, ethyl acetate/hexane) to afford the desired product.

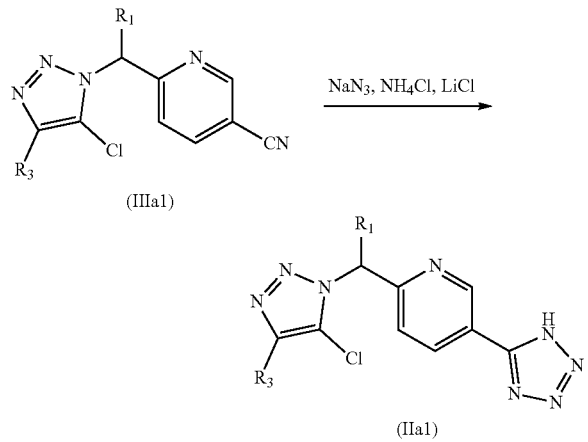

To a solution of the corresponding nitrile derivative (1.0 mmol) in N,N-dimethylformamide at room temperature, NaN$_3$ (4.7 mmol, 0.305 g), NH$_4$Cl (4.7 mmol, 0.251 g) and LiCl (1.7 mmol, 0.071 g) were subsequently added. The reaction mixture was stirred at 100° C. and monitored by TLC until the completion of the reaction. The crude thus obtained was used without further purification.

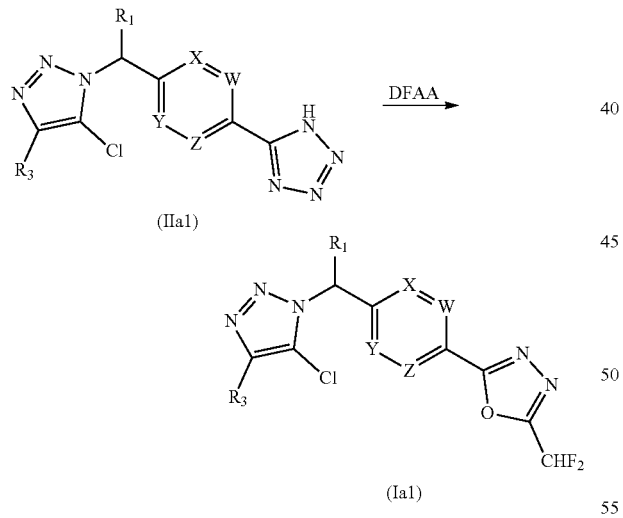

To the crude reaction obtained in the previous step, DFAA (20.0 mmol, 2.5 ml) was added at room temperature. The reaction mixture was stirred at 60° C. (when W=N) or 100° C. (when W=C). The progress of the reaction was monitored by HPLC-MS. After the completion of the reaction, water was added and this solution was extracted with ethyl acetate. The combined organic fractions were washed with water and brine, dried over Na$_2$SO$_4$ and evaporated under reduced pressure. The crude thus obtained was purified by flash chromatography (silica gel, ethyl acetate/hexane) to afford the desired product with high purity (>90%).

Representative examples prepared by employing this protocol were:

Example 51: 2-(4-((5-chloro-4-phenyl-1H-1,2,3-triazol-1-yl)methyl)phenyl)-5-(difluoromethyl)-1,3,4-oxadiazole

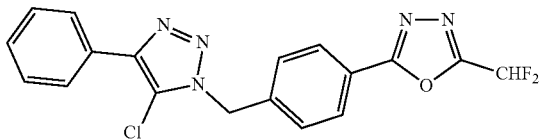 [SMILES: FC(F)c1nnc(-c2ccc(Cn3nnc(-c4ccccc4)c3Cl)cc2)o1]

White solid; $^1$H NMR (δ ppm, 400 MHz, DMSO-d$_6$)$^1$H NMR (400 MHz, DMSO-d$_6$) 8.11 (d, J=8.3 Hz, 2H), 7.95-7.91 (m, 2H), 7.56 (t, J=51.4 Hz, 1H), 7.56-7.52 (m, 4H), 7.48-7.44 (m, 1H), 5.88 (s, 2H); MS (ESI, m/z): 388.20 and 390.20 [M+1]$^+$.

Intermediates (phenylethynyl)copper

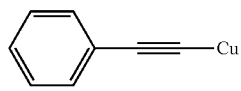

MS (ESI, m/z): 388.20 [M+1]$^+$.

(5-(4-(azidomethyl)phenyl)-1H-tetrazole

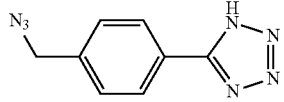

MS (ESI, m/z): 202.20 [M+1]$^+$.

5-(4-((5-chloro-4-phenyl-1H-1,2,3-triazol-1-yl)methyl)phenyl)-1H-tetrazole

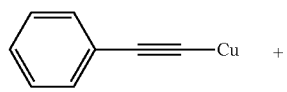

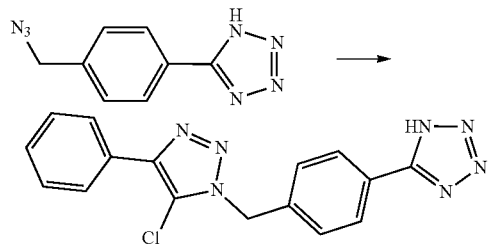

MS (ESI, m/z): 338.19 and 340.18 [M+1]$^+$.

Example 52: 2-(6-((5-chloro-4-phenyl-1H-1,2,3-triazol-1-yl)methyl)pyridin-3-yl)-5-(difluoromethyl)-1,3,4-oxadiazole, with the Following Structural Formula

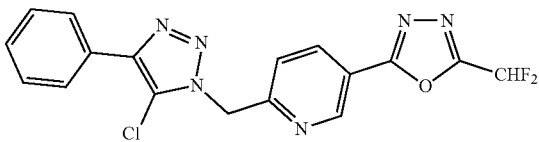 [SMILES: FC(F)c1nnc(-c2ccc(Cn3nnc(-c4ccccc4)c3Cl)nc2)o1]

White solid; $^1$H NMR (δ ppm, 400 MHz, DMSO-d$_6$)$^1$H NMR (400 MHz, DMSO-d$_6$) 9.18 (d, J=2.3 Hz, 1H), 8.52 (dd, J=8.2, 2.3 Hz, 1H), 7.99-7.92 (m, 2H), 7.68 (d, J=8.3 Hz, 1H), 7.59 (d, J=51.3 Hz, 1H), 7.55 (t, J=7.7 Hz, 2H), 7.48-7.44 (m, 1H), 6.02 (s, 2H); MS (ESI, m/z): 389.22 and 391.21 [M+1]$^+$.

Example 53: 2-(6-((5-chloro-4-(2-chlorophenyl)-1H-1,2,3-triazol-1-yl)methyl)pyridin-3-yl)-5-(difluoromethyl)-1,3,4-oxadiazole

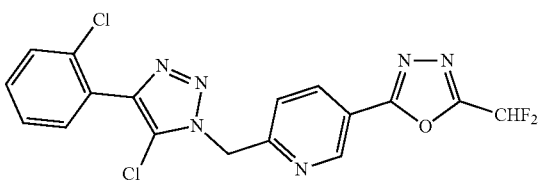 [SMILES: FC(F)c1nnc(-c2ccc(Cn3nnc(-c4ccccc4Cl)c3Cl)nc2)o1]

Yellow oil; $^1$H NMR (δ ppm, 400 MHz, CDCl$_3$-d) 9.37 (d, J=2.1 Hz, 1H), 8.46 (dd, J=8.3, 2.2 Hz, 1H), 7.58-7.54 (m, 2H), 7.45-7.41 (m, 2H, 7.32 (d, J=8.5 Hz, 1H), 6.97 (t, J=51.6 Hz, 1H), 5.89 (s, 2H); MS (ESI, m/z): 423.19 and 425.18 [M+1]$^+$.

Example 54: 2-(6-((5-chloro-4-(3-chlorophenyl)-1H-1,2,3-triazol-1-yl)methyl)pyridin-3-yl)-5-(difluoromethyl)-1,3,4-oxadiazole

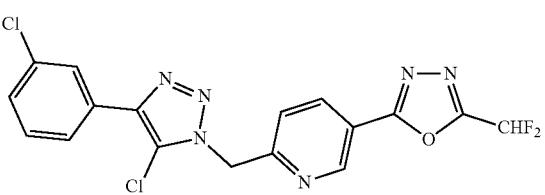 [SMILES: FC(F)c1nnc(-c2ccc(Cn3nnc(-c4cccc(Cl)c4)c3Cl)nc2)o1]

Yellow oil; $^1$H NMR (δ ppm, 400 MHz, CDCl$_3$-d) 9.35 (d, J=2.2 Hz, 1H), 8.45 (dd, J=8.2, 2.2 Hz, 1H), 8.05 (t, J=1.9 Hz, 1H), 7.94 (dt, J=7.5, 1.6 Hz, 1H), 7.49-7.39 (m, 2H), 7.34 (d, J=8.2 Hz, 1H), 6.97 (t, J=51.6 Hz, 1H), 5.87 (s, 2H); MS (ESI, m/z): 423.19 and 425.22 [M+1]$^+$.

Example 67: Preparation of 2-(6-((5-chloro-4-(2-fluorophenyl)-1H-1,2,3-triazol-1-yl)methyl)pyridin-3-yl)-5-(difluoromethyl)-1,3,4-oxadiazole, with the Following Structural Formula

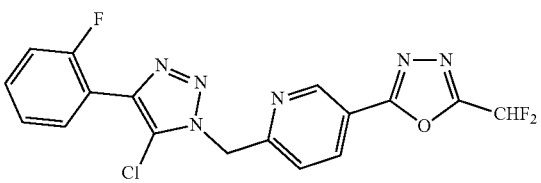 [SMILES: Fc1ccccc1-c1nnn(Cc2ccc(-c3nnc(C(F)F)o3)cn2)c1Cl]

This compound was prepared following procedures described in Method C. Yellow oil;
$^1$H NMR (δ ppm, 400 MHz, CDCl$_3$-d) 9.37 (s, 1H), 8.46 (d, J=8.1 Hz, 1H), 7.76 (td, J=7.5, 1.8 Hz, 1H), 7.47 (tdd, J=7.3, 6.1, 1.6 Hz, 1H), 7.33-7.27 (m, 2H), 7.23 (ddd, J=9.7, 8.3, 1.1 Hz, 1H), 6.97 (t, J=51.6 Hz, 1H), 5.88 (s, 2H); MS (ESI, m/z): 407.22 and 409.22 [M+1]$^+$.

Compounds obtained by any of the above methods may be further transformed into other compounds of the invention. A representative example is shown below.

Example 55: 2-(6-(chloro(4-phenyl-1H-1,2,3-triazol-1-yl)methyl)pyridin-3-yl)-5-(difluoromethyl)-1,3,4-oxadiazole

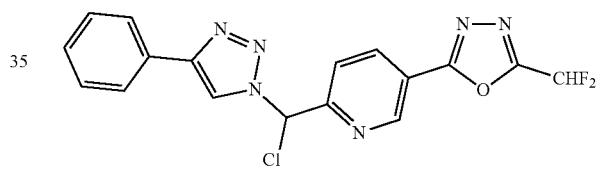

To a solution of Example 39 (0.05 mmol) in N,N-dimethylformamide (0.3 ml), N-chlorosuccinimide (0.08 mmol, 0.015 g) was added. The resulting mixture was refluxed for 16 h. Then, the crude reaction solution was evaporated to dryness under reduced pressure and purified by flash chromatography (silica gel, ethyl acetate/hexane) to afford the desired product.

Yellow oil; $^1$H NMR (δ ppm, 400 MHz, CDCl$_3$-d) 9.43 (d, J=2.2 Hz, 1H), 8.58 (dd, J=8.2, 2.2 Hz, 1H), 8.42 (s, 1H), 7.94-7.88 (m, 3H), 7.69 (s, 1H), 7.48 (dd, J=8.2, 6.7 Hz, 2H), 7.44-7.37 (m, 1H), 6.99 (t, J=51.6 Hz, 1H); MS (ESI, m/z): 389.25 and 391.25 [M+1]$^+$.

Biological Activity of the Compounds of the Present Invention

All enzymatic reactions were conducted in duplicate at room temperature for 17 hours in a 50 μL mixture containing HDAC assay buffer (50 mM Tris-HCl, pH 7.4, 137 mM NaCl, 2.7 mM KCl, 0.05% Tween 20, 5 μg BSA), an HDAC substrate, an HDAC enzyme, and a test compound. Compound dilution was prepared one hundred-fold higher than the final concentration of the compounds with 100% DMSO and 300 nL of the dilution was added by Echo acoustic dispenser to a 30 μL reaction so that the final concentration of DMSO is 1% in all of reactions. After enzymatic reactions, reaction was stopped by adding 5 μl of 10 μM solution of a known inhibitor. The fluorescent signal of substrate and product was measured by means of microfluidics mobility assay in a EZ Reader II equipment. The percentage of conversion of substrate into product was calculated by the equipment software based on the area of the peaks.

The percentage of conversion data were analyzed using the computer software, Graphpad Prism. In the absence of the compound, the conversion (Ct) in each data set was defined as 100% activity. In the absence of HDAC, the conversion (Cb) in each data set was defined as 0% activity. The percent activity in the presence of each compound was calculated according to the following equation: % inhibition=(Ct−C)/(Ct−Cb), where C=the percentage of conversion in the presence of the compound.

The values of % inhibition versus a series of compound concentrations were then plotted using non-linear regression analysis of Sigmoidal dose-response curve generated with the equation Y=B+(T−B)/1+10((Log EC50−X)×Hill Slope), where Y=percent inhibition, B=minimum percent inhibition, T=maximum percent inhibition, X=logarithm of compound and Hill Slope=slope factor or Hill coefficient. The $IC_{50}$ value was determined by the concentration causing a half-maximal percent activity.

hHDAC1 Inhibition Protocol

The buffer assay used in the inhibition hHDAC1 assay is: Hepes 50 mM, KCl 100 mM, Tween 20 0.001%, BSA 0.01%; pH=7.4. Study compound and HDAC1 (BPS Bioscience 50010) enzyme 5 nM was added in a 384 well Microplate (Geriner 784209) and incubated during 3 hours at RT. Later Acetylated Peptide A (Perkin Elmer CLS960006) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC1, LBH-589 (Reaction Biology Corp EP1009B) IC50 1 nM, J Med Chem 2016, 59, 1455-1470.

hHDAC2 Inhibition Protocol

The buffer assay used in the inhibition hHDAC2 assay is: Hepes 50 mM, KCl 100 mM, Tween 20 0.001%, BSA 0.01%; pH=7.4. Study compound and HDAC2 (BPS Bioscience 50002) enzyme 12 nM was added in a 384 well Microplate (Geriner 784209) and incubated during 3 hours at RT. Later Acetylated Peptide A (Perkin Elmer CLS960006) 1 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. hHDAC2, LBH-589 (Reaction Biology Corp EP1009B) IC50<3 nM, Gale et al, Application note Perkin Elmer.

hHDAC3 Inhibition Protocol

The buffer assay used in the inhibition hHDAC3 assay is: Hepes 50 mM, KCl 100 mM, Tween 20 0.001%, BSA 0.01%; pH=7.4. Study compound and HDAC3 (BPS Bioscience 50003) enzyme 5 nM was added in a 384 well Microplate (Geriner 784209) and incubated during 3 hours at RT. Later Acetylated Peptide A (Perkin Elmer CLS960006) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC3, LBH-589 (Reaction Biology Corp EP1009B) IC50 2 nM, Cancer Lett 2009; 280:233-241.

hHDAC4 Inhibition Protocol

The buffer assay used in the inhibition hHDAC4 assay is: Hepes 50 mM, KCl 100 mM, Tween 20 0.001%, BSA 0.01%; pH=7.4. Study compound and HDAC4 (BPS Bioscience 50004) enzyme 0.5 nM was added in a 384 well Microplate (Geriner 784209) and incubated during 5 minutes at RT. Later Acetylated Peptide B (Perkin Elmer CLS960007) 1 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC4, LBH-589 (Reaction Biology Corp EP1009B), IC50 65 nM, Gale et al., Application note Perkin Elmer.

hHDAC5 Inhibition Protocol

The buffer assay used in the inhibition hHDAC5 assay is: Hepes 50 mM, KCl 100 mM, Tween 20 0.001%, BSA 0.01%; pH=7.4. Study compound and HDAC5 (BPS Bioscience 50005) enzyme 0.75 nM was added in a 384 well Microplate (Geriner 784209) and incubated during 5 minutes at RT. Later Acetylated Peptide B (Perkin Elmer CLS960007) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC5, LBH-589 (Reaction Biology Corp EP1009B), IC50 160 nM, Nat. Chem. Biol. 6,238-243 (2010).

HDAC6 Inhibition Protocol

The buffer assay used in the inhibition hHDAC6 assay is: Hepes 50 mM, KCl 100 mM, Tween 20 0.001%, BSA 0.01%; pH=7.4. Study compound and hHDAC6 (BPS Bioscience 50006) enzyme 1.20 nM was added in a 384 well Microplate (Greiner 784209) and incubated during 5 minutes at RT. Later Acetylated Peptide A (Perkin Elmer CLS960006) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC6, LBH589 (Reaction Biology Corp EP1009B), IC50 2.0 nM, Gale et al., Perkin Elmer Application note.

hHDAC7 Inhibition Protocol

The buffer assay used in the inhibition hHDAC7 assay is: Hepes 50 mM, KCl 100 mM, Tween 20 0.001%, BSA 0.01%; pH=7.4. Study compound and HDAC7 (BPS Bioscience 50007) enzyme 5 nM was added in a 384 well Microplate (Geriner 784209) and incubated during 5 minutes at RT. Later Acetylated Peptide B (Perkin Elmer CLS960007) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: Literature IC50 value of reference compound to validate the assay: hHDAC7, LBH-589 (Reaction Biology Corp EP1009B), IC50 760 nM, Gale et al, Application note Perkin Elmer.

hHDAC8 Inhibition Protocol

The buffer assay used in the inhibition hHDAC8 assay is: Hepes 50 mM, KCl 100 mM, Tween 20 0.001%, BSA 0.01%; pH=7.4. Study compound and HDAC8 (BPS Bioscience 50008) enzyme 1 nM was added in a 384 well Microplate (Geriner 784209) and incubated during 5 minutes at RT. Later Acetylated Peptide B (Perkin Elmer CLS960007) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC8, Trichostatin A (Reaction Biology Corp. EP1009F), IC50 90 nM, Bradner, J. E. et al. Nat. Chem. Biol. 6, 238-243 (2010).

hHDAC9 Inhibition Protocol

The buffer assay used in the inhibition hHDAC9 assay is: Hepes 50 mM, KCl 100 mM, Tween 20 0.001%, BSA 0.01%; pH=7.4. Study compound and HDAC9 (BPS Bioscience 50009) enzyme 2 nM was added in a 384 well Microplate (Geriner 784209) and incubated during 5 minutes at RT. Later Acetylated Peptide B (Perkin Elmer CLS960007) 2 µM was added and incubated during 1 hour at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: Literature IC50 value of reference compound to validate the assay: hHDAC9, LBH-589 (Reaction Biology Corp EP1009B), IC50 390 nM, Gale et al., Application note Perkin Elmer.

HDAC10 Inhibition Protocol

The buffer assay used in the inhibition hHDAC10 assay is: Hepes 50 mM, KCl 100 mM, Tween 20 0.001%, BSA 0.01%; pH=7.4. Study compound and hHDAC10 (BPS Bioscience 50010) enzyme 10 nM was added in a 384 well Microplate (Geriner 784209) and incubated during 60 minutes at RT. Later Acetylated Peptide A (Perkin Elmer CLS960007) 6 µM was added and incubated during 24 hours at RT. Finally, LBH589 (Reaction Biology Corp EP1009B) 1.4 µM was added to stop the reaction. The reaction was measured in a Caliper EzReader LabChip 3000 (Caliper, Hopkinton, MA) reader. Literature IC50 value of reference compound to validate the assay: hHDAC10, SAHA (supplied by Quimatryx), IC50 456 nM, Hanessian et al., ACS Med. Chem. Lett. 2010, 1, 2, 70-74.

The following HDAC6 inhibitory activities were observed for Examples 1-67

| Compound | IC50 (nM) of enzyme activity HDAC6 |
|---|---|
| Example 1 | 3043.0 |
| Example 2 | 1036.0 |
| Example 3 | 4914.7 |
| Example 4 | 1755.7 |
| Example 5 | 239.3 |
| Example 6 | 417.3 |
| Example 7 | 364.8 |
| Example 8 | 386.7 |
| Example 9 | 235.7 |
| Example 10 | 60.2 |
| Example 11 | 171.3 |
| Example 12 | 189.6 |
| Example 13 | 129.1 |
| Example 14 | 190.4 |
| Example 15 | 213.7 |
| Example 16 | 257.6 |
| Example 17 | 919.7 |
| Example 18 | 1164.9 |
| Example 19 | 228.8 |
| Example 20 | 589.1 |
| Example 21 | 103.3 |
| Example 22 | 22.4 |
| Example 23 | 190.3 |
| Example 24 | 29.5 |
| Example 25 | 29.8 |
| Example 26 | 48.3 |
| Example 27 | 85.3 |
| Example 28 | 2801.2 |
| Example 29 | 95.6 |
| Example 30 | 238.3 |
| Example 31 | 272.7 |
| Example 32 | 474.6 |
| Example 40 | 685.7 |
| Example 67 | 67.4 |
| Example 33 | 188.4 |
| Example 34 | 202.0 |
| Example 35 | 131.3 |
| Example 36 | 104.9 |
| Example 37 | 149.4 |
| Example 38 | 266.5 |
| Example 39 | 366.3 |
| Example 41 | 40.9 |
| Example 42 | 1990.5 |
| Example 43 | 43.1 |
| Example 44 | 37.1 |
| Example 45 | 33.5 |
| Example 46 | 37.9 |
| Example 47 | 25.7 |
| Example 48 | 24.0 |
| Example 49 | 66.7 |
| Example 50 | 43.5 |
| Example 51 | 87.9 |
| Example 52 | 48.4 |
| Example 53 | 81.5 |
| Example 54 | 34.1 |
| Example 55 | 58.2 |
| Example 56 | 66.5 |
| Example 57 | 148.8 |
| Example 58 | 121.3 |
| Example 59 | 85.1 |
| Example 60 | 42.3 |
| Example 61 | 186.8 |
| Example 62 | 61.8 |
| Example 63 | 48.3 |
| Example 64 | 48.7 |
| Example 65 | 40.4 |
| Example 66 | 33.3 |

In addition, the Examples (Ex.) 1-67 displayed a high degree of selectivity over the other HDAC1-10 enzymes. Representative selectivities are shown in the table below.

| Ex. | HDAC1 | HDAC2 | HDAC3 | HDAC4 | HDAC5 | HDAC6 | HDAC7 | HDAC8 | HDAC9 | HDAC10 |
|---|---|---|---|---|---|---|---|---|---|---|
| 7 | >10000 | >10000 | >10000 | >10000 | >10000 | 364.8 | >10000 | >10000 | >10000 | >10000 |
| 11 | >10000 | >10000 | >10000 | >10000 | >10000 | 171.3 | >10000 | >10000 | >10000 | >10000 |
| 14 | >10000 | >10000 | >10000 | >10000 | >10000 | 190.4 | >10000 | >10000 | >10000 | >10000 |
| 22 | >10000 | >10000 | >10000 | 2404.6 | >10000 | 22.4 | 9400 | >10000 | 6522 | >10000 |
| 24 | >10000 | >10000 | >10000 | 8370.3 | >10000 | 29.5 | >10000 | >10000 | 8615.5 | >10000 |
| 25 | >10000 | >10000 | >10000 | >10000 | >10000 | 29.8 | >10000 | >10000 | >10000 | >10000 |
| 27 | >10000 | >10000 | >10000 | >10000 | >10000 | 85.3 | >10000 | >10000 | >10000 | >10000 |
| 48 | >10000 | >10000 | >10000 | >10000 | >10000 | 24.0 | >10000 | >10000 | >10000 | >10000 |
| 54 | >10000 | >10000 | >10000 | 1488.5 | >10000 | 34.1 | 1399.8 | >10000 | 2612.4 | >10000 |

IC50 (nM) of enzyme activity

The invention claimed is:

1. A compound of formula (I)

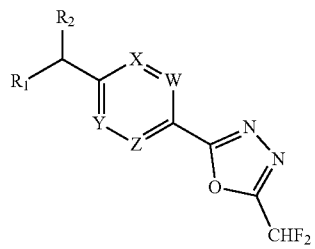

or a salt, solvate, stereoisomer or prodrug thereof, wherein
one or two of W, X, Y or Z is N, and the remainder of W, X, Y and Z are each CH; or each of W, X, Y and Z is CH;
$R_1$ is H; unsubstituted or substituted alkyl; or halogen; and
$R_2$ is an unsubstituted or substituted, aromatic or non-aromatic heterocyclic ring, wherein the ring comprises from 1 to 4 nitrogen atoms, and wherein it is one of these ring nitrogen atoms of the $R_2$ group that forms the bond to the rest of formula (I).

2. The compound according to claim 1, wherein X is N and the remainder of W, X, Y and Z are each CH.

3. The compound according to claim 1, wherein each of W, X, Y and Z is CH.

4. The compound according to claim 1, wherein $R_1$ is H.

5. The compound according to claim 1, wherein $R_2$ is aromatic.

6. The compound according to claim 5, wherein $R_2$ is a 5-membered monocyclic heteroaryl ring.

7. The compound according to claim 6, wherein $R_2$ is a triazolyl or an imidazolyl ring.

8. The compound according to claim 5, wherein $R_2$ is a 9-membered bicyclic heteroaryl ring.

9. The compound according to claim 8, wherein $R_2$ is a benzotriazolyl or benzoimidazolyl ring.

10. The compound according to claim 1, selected from:

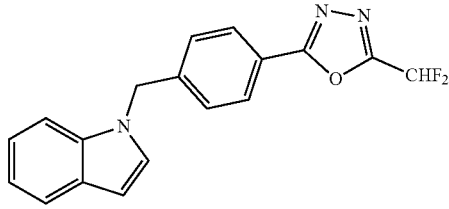

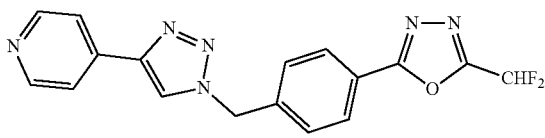

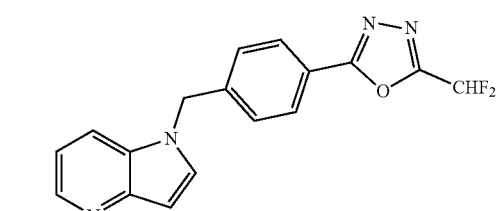

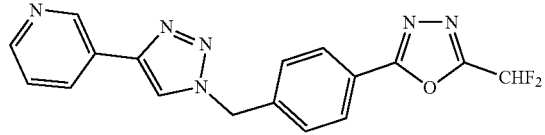

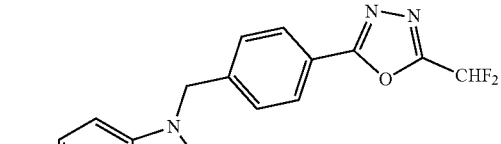

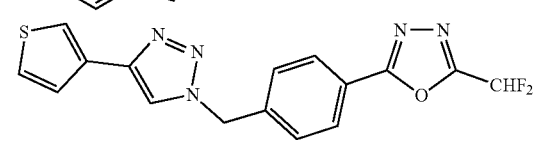

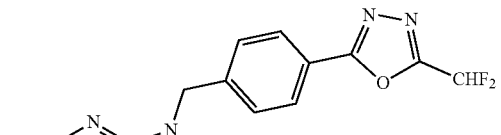

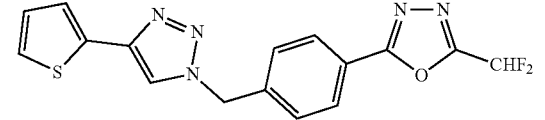

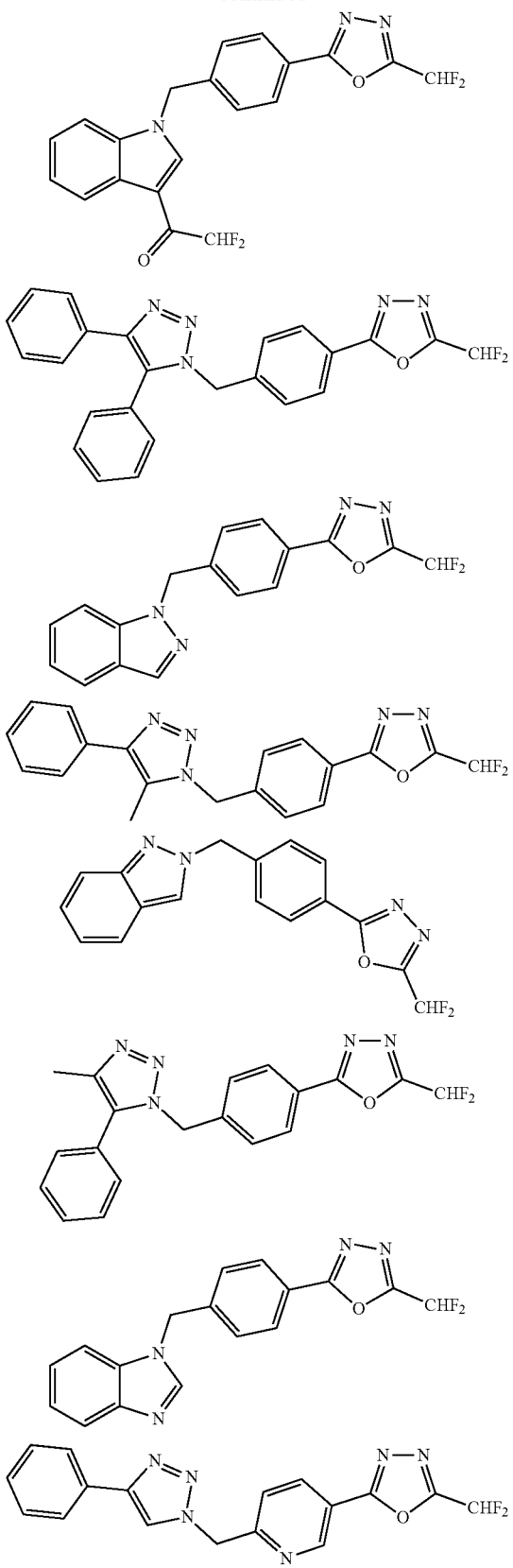
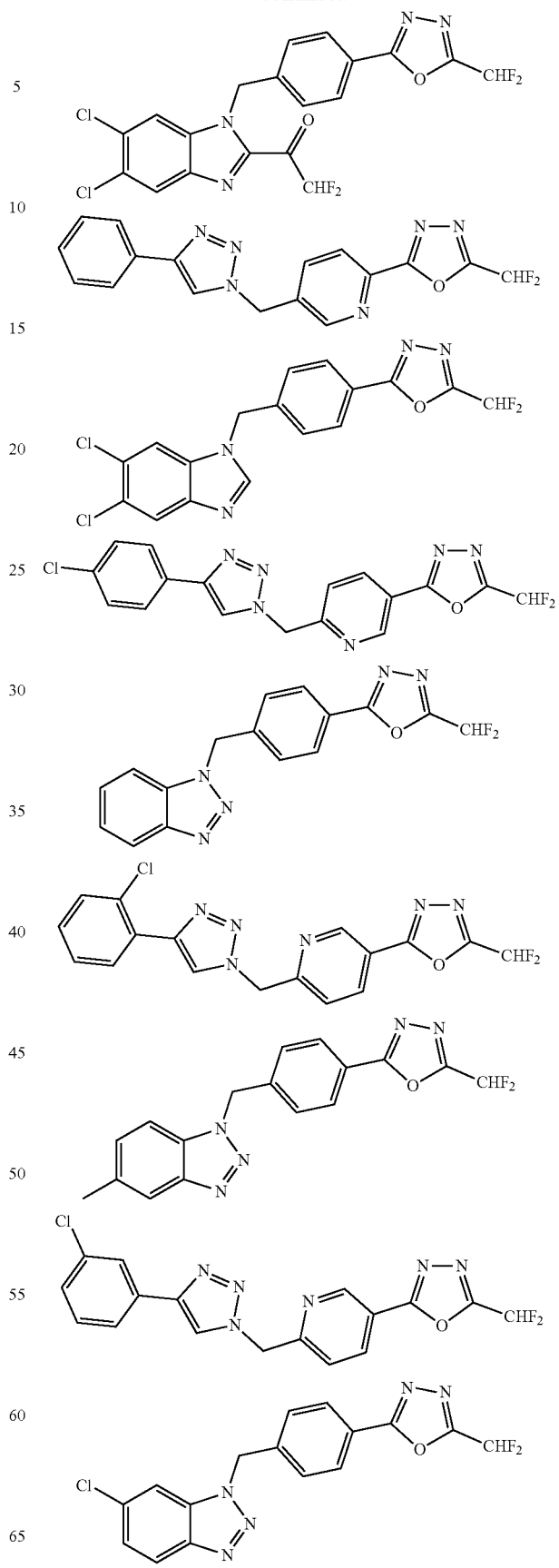

75
-continued
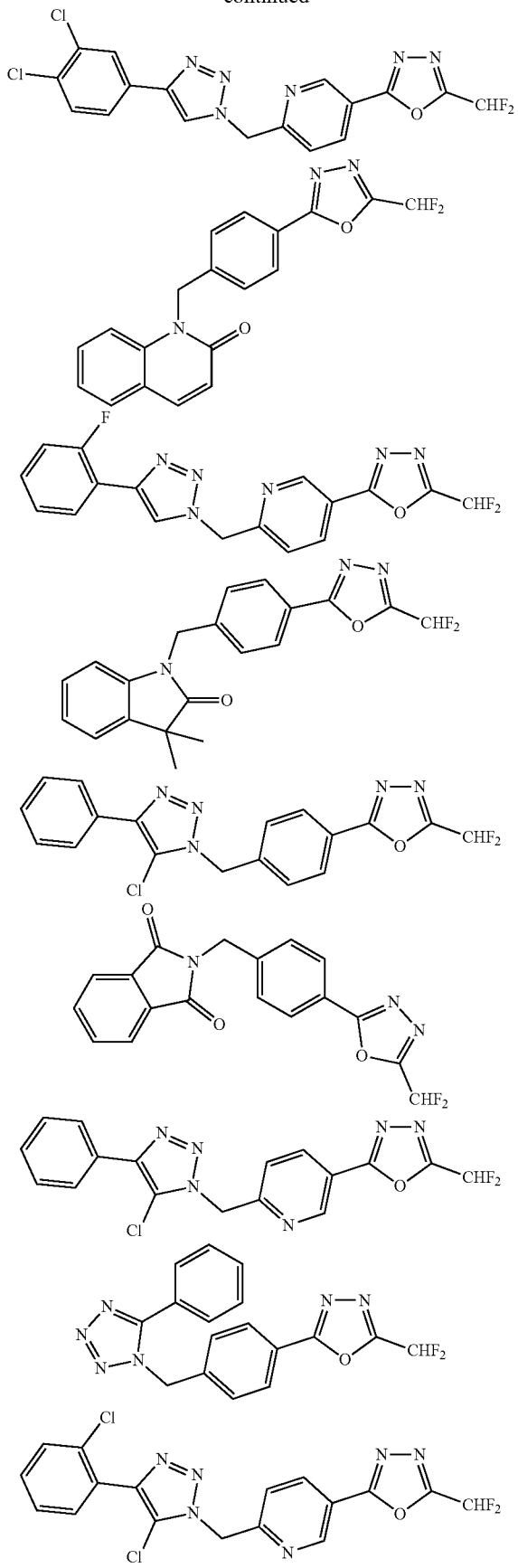
76
-continued
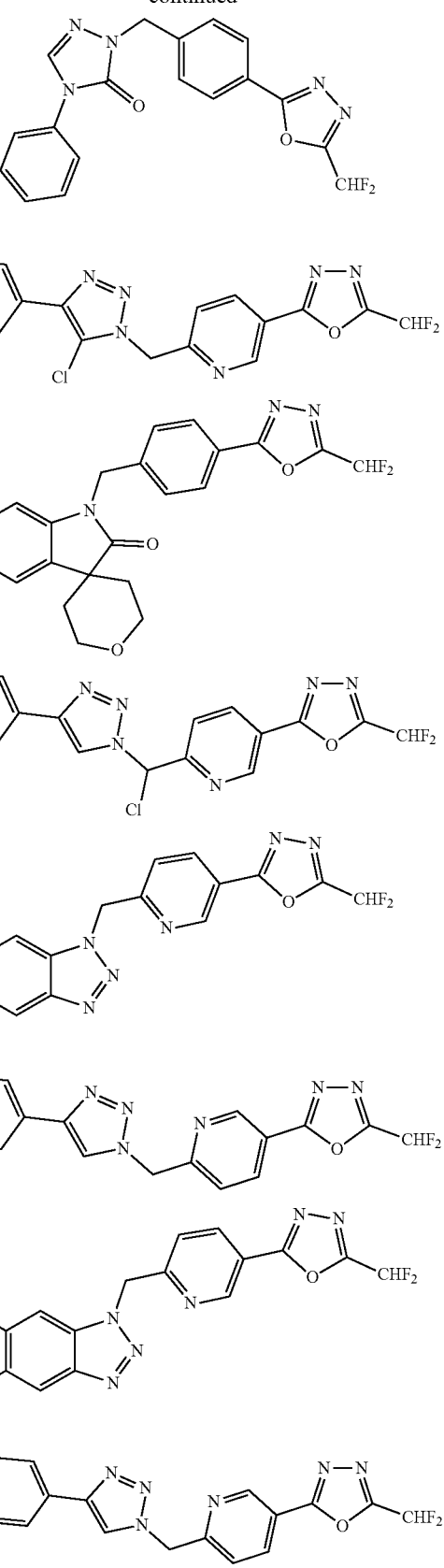

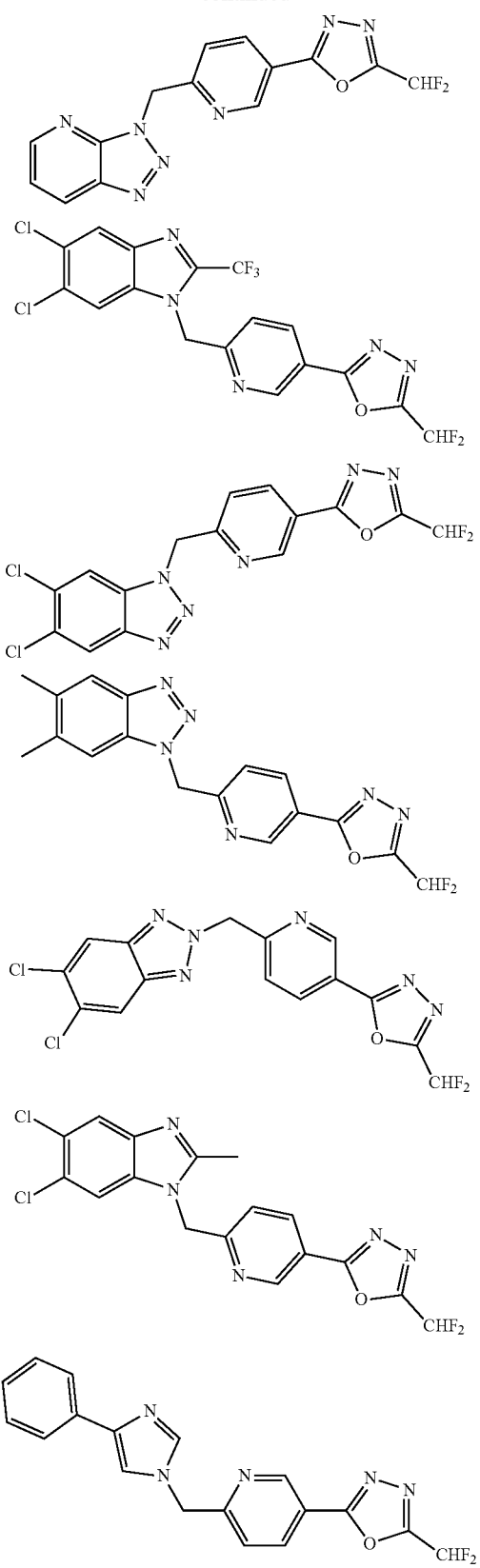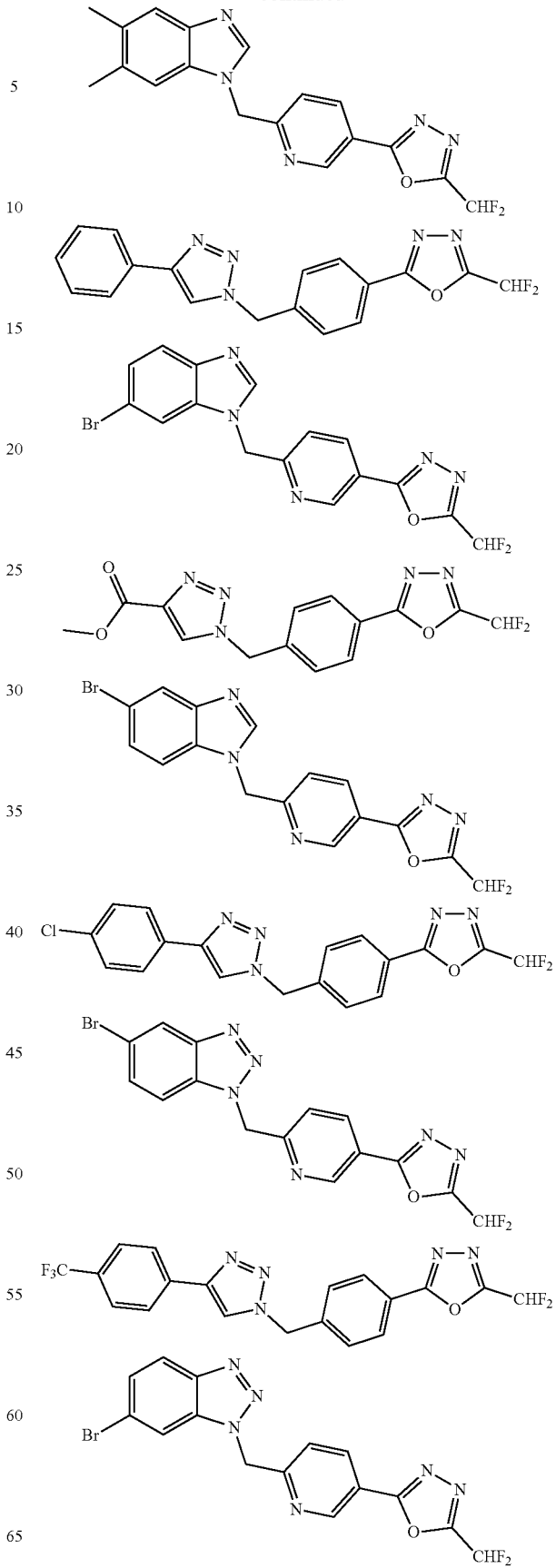

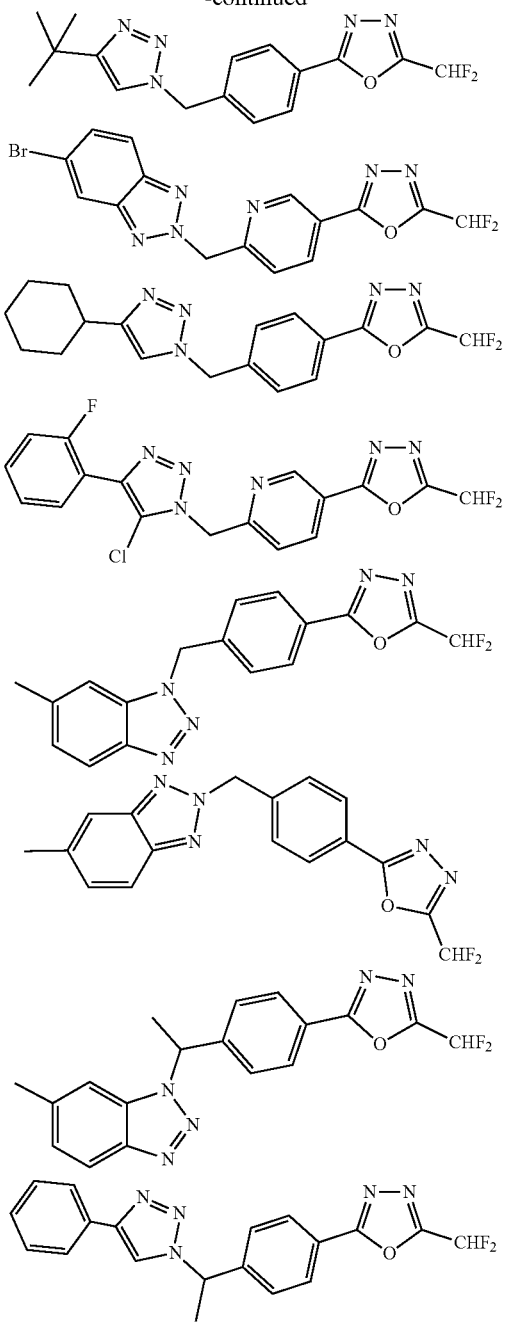

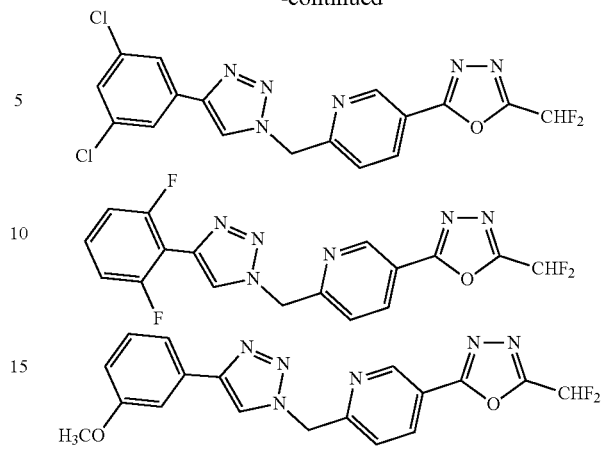

or a salt, solvate, stereoisomer or prodrug thereof.

11. A process for the preparation of a compound of formula (I) as defined in claim 1, comprising reacting a tetrazole of formula (II)

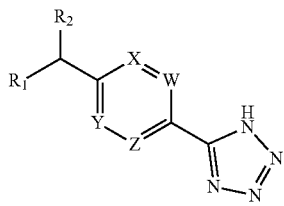

wherein W, X, Y, Z, $R_1$, $R_2$ are as defined in claim 1, with difluoroacetic anhydride.

12. A pharmaceutical composition comprising a compound of formula (I) as defined in claim 1, or a salt, solvate, stereoisomer or prodrug thereof, and at least one pharmaceutically acceptable excipient.

13. A method for the inhibition of histone deacetylase (HDAC) activity, said method comprising administering to a patient in need of such inhibition a therapeutically effective amount of a compound of formula (I) as defined in claim 1.

14. The method according to claim 13, wherein the HDAC inhibited is HDAC6.

15. The method according to claim 14, wherein HDAC6 is selectively inhibited relative to HDAC1-5 and HDAC7-10.

* * * * *

UNITED STATES PATENT AND TRADEMARK OFFICE
CERTIFICATE OF CORRECTION

PATENT NO. : 12,202,823 B2
APPLICATION NO. : 17/604017
DATED : January 21, 2025
INVENTOR(S) : Yosu Ion Vara Salazar et al.

Page 1 of 1

It is certified that error appears in the above-identified patent and that said Letters Patent is hereby corrected as shown below:

In the Claims

Column 79, Claim 10, Lines 38-45 should read:

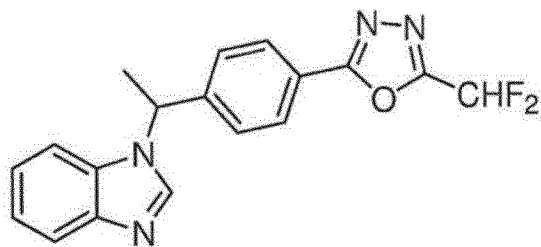

Signed and Sealed this
Eighteenth Day of March, 2025

Coke Morgan Stewart
*Acting Director of the United States Patent and Trademark Office*